(12) United States Patent
Claussen et al.

(10) Patent No.: US 6,241,916 B1
(45) Date of Patent: *Jun. 5, 2001

(54) ELECTROCHROMIC SYSTEM

(75) Inventors: Uwe Claussen; Horst Berneth, both of Leverkusen; Dietrich Haarer, Bayreuth; Jürgen Simmerer, Erlangen; Jochen Schaller, Schwarzenbach, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/125,198

(22) PCT Filed: Feb. 4, 1997

(86) PCT No.: PCT/EP97/00498

§ 371 Date: Jan. 12, 1999

§ 102(e) Date: Jan. 12, 1999

(87) PCT Pub. No.: WO97/30134

PCT Pub. Date: Aug. 21, 1997

(30) Foreign Application Priority Data

Feb. 15, 1996 (DE) .............................................. 196 05 451

(51) Int. Cl.[7] .................................. G02F 1/15; G09G 3/19
(52) U.S. Cl. ........................... 252/583; 345/49; 359/265; 359/267; 359/272; 359/276
(58) Field of Search ............................ 252/583; 359/265, 359/267, 272, 276; 345/49

(56) References Cited

U.S. PATENT DOCUMENTS

| | | | |
|---|---|---|---|
| 3,280,701 | 10/1966 | Donnelly et al. | 88/77 |
| 4,090,782 | * 5/1978 | Bredfeldt et al. | 359/265 |
| 4,093,358 | * 6/1978 | Shattuck et al. | 252/583 |
| 4,902,108 | * 2/1990 | Byker | 359/265 |
| 5,128,799 | * 7/1992 | Byker | 359/265 |
| 5,140,455 | 8/1992 | Varaprasad et al. | 359/275 |
| 5,336,448 | * 8/1994 | Byker | 252/583 |
| 5,340,503 | * 8/1994 | Varaprasad et al. | 252/583 |
| 5,611,966 | * 3/1997 | Varaprasad et al. | 252/583 |

FOREIGN PATENT DOCUMENTS

| | | |
|---|---|---|
| 39 17 323 | 11/1990 | (DE) . |
| 44 35 211 | 4/1995 | (DE) . |
| 240 226 | 10/1987 | (EP) . |
| 435 689 | 7/1991 | (EP) . |
| 613 039 | 8/1994 | (EP) . |

OTHER PUBLICATIONS

CA 117: 7438, 1992.*
CA 111: 96581, 1989.*
S Hünig et al., "Two Step Reversible Redox Systems of the Weitz Type", Topics in Current Chem., vol. 92, (1980), pp. 1–44.
K. Deuchert et al., "Multistage Organic Redox Systems—A General Structural Principle", Angew. Chemie, vol. 17, No. 12, 12/78, pp. 875–886.
S. Hünig et al., "DCNQIs—New Electron Acceptors for Charge–Transer . . . Anion Salts", Adv. Material vol. 3, No. 5, (1991), pp. 225–236.
G.V. Tormos et al., "Dithiadizafulvalenes—New Strong Electron Doners . . . and EPR Studies", J. Am. Chem. Soc., vol. 117, (1995), pp. 8528–8535.
M.R. Bryce et al., "Synthesis and Redox Behaviour of Highly . . . Model Systems for Organic Metals", J. Chem. Soc. Perkin Trans., 1990, pp. 1777–1783.

* cited by examiner

Primary Examiner—Shean C. Wu
(74) Attorney, Agent, or Firm—Foley & Lardner

(57) ABSTRACT

The novel electrochromic system comprises at least one reducible and at least one oxidizable substance $OX_2$ and $RED_1$ respectively, which are linked with one another via a bridge member, and is outstandingly suitable for use in an electrochromic device.

19 Claims, No Drawings

ELECTROCHROMIC SYSTEM

This application is a 371 of PCT/EP97/00498, filed Feb. 4, 1997.

The present invention relates to an electrochromic system, an electrochromic liquid compriesing this electrochromic system, an electrochromic device and novel electrochromic substances and processes for their preparation.

Electrochromic devices which comprise an electrochromic system are already known.

Such devices usually comprise, as the electrochromic system, pairs of redox substances dissolved in an inert solvent. They can additionally comprise conductive salts, light stabilizers and substances which influence the viscosity.

A reducible substance and an oxidizable substance are used as the pair of redox. substances. Both are colorless or only slightly colored. Under the influence of an electrical voltage, one of the substances is reduced and the other is oxidized, at least one becoming colored. When the voltage is switched off, the two original redox substances are formed again, decoloration or a lightening in color occurring.

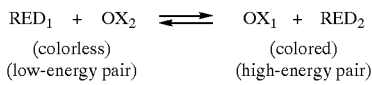

(colorless) (colored)
(low-energy pair) (high-energy pair)

It is known from U.S. Pat. No. 4,902,108 that those pairs of redox substances in which the reducible substance has at least two chemically reversible reduction waves in the cyclic voltammogram and the oxidizable substance correspondingly has at least two chemically reversible oxidation waves are suitable.

Electrochromic devices can be used in various ways. First, for example, they can be constructed as automobile rearview mirrors which can be darkened by applying a voltage during nighttime driving, so that blinding by headlamps of other vehicles is prevented (cf, for example, U.S. Pat. No. 3,280,701, U.S. Pat. No. 4,902,108, EP-A-0.435.689). Such devices can furthermore also be employed in window panes or automobile sunroofs, where they dim sunlight when a voltage is applied. Finally, a matrix display for graphic illustration of information such as letters, numbers and symbols can also be built up with such devices.

Electrochromic devices usually comprise a pair of panes of glass or plastic, one of which is metallized in the case of an automobile mirror. One side of these panes is coated with a transparent, electrically conductive layer, for example indium tin oxide (ITO). A cell is now built up from these panes by joining them, preferably gluing them, by means of an annular or rectangular sealing ring with their sides with the electrically conductive coating facing one another. The sealing ring produces a uniform distance between the panes, for example 0.1 to 0.5 mm. This cell is now filled with an electrochromic solution via an opening, and the cell is closed tight. The two panes can be contacted separately via the ITO layer.

The electrochromic systems known from the prior art comprise those pairs of redox substances which, after reduction or oxidation, form colored free radicals, cationic radicals or ionic radicals which are chemically reactive. As is known, for example, from Topics in Current Chemistry, Volume 92, pages 1–44 (1980), such free radicals (radical ions) may be sensitive to electrophiles or nucleophiles or else free radicals. To achieve a high stability of an electrochromic device which comprises such an electrochromic system and which should withstand several thousand switching cycles, it must therefore be ensured that the solvent used is absolutely free from electrophiles, for example protons, nucleophiles and oxygen. It must furthermore be ensured that such reactive species do not form due to electrochemical processes at the electrodes during operation of the electrochromic device.

The reverse reaction formulated according to the above equation to give $RED_1$ and $OX_2$ also takes place continuously away from the electrodes within the solution volume during operation of the electrochromic device. Because of the risks of degradation reactions of the free radicals (radical ions) due to electrophiles, nucleophiles or free radicals, it is important for the long-term stability of the display that the reverse reaction according to the above equation can take place as quickly as possible and without side reactions.

It has been found that, by coupling $RED_1$ and $OX_2$ via a covalent chemical bond, electron transfer is facilitated and the reverse reaction according to the above equation can thus be accelerated and side reactions avoided.

The present invention accordingly relates to an electrochromic system comprising at least one oxidizable substance $RED_1$ and at least one reducible substance $OX_2$ which, by electron donation of the former at an anode and by electron acceptance of the latter at a cathode, in each case with an increase in the extinction in the visible range of the spectrum, are converted from a slightly colored or colorless form into a colored form $OX_1$ and $RED_2$ respectively, in each case the slightly colored or colorless form being reformed after charge compensation, wherein at least one of the substances $RED_1$ and $OX_2$ contained therein are linked together covalently via a bridge.

The reduction and oxidation processes in the electrochemical system according to the invention are in general effected by electron acceptance or donation at a cathode or anode, a potential difference of 0.3 to 3 V preferably prevailing between the electrodes. When the electrical potential is switched off, a charge compensation generally takes place spontaneously between the substances $RED_2$ and $OX_1$, decoloration or a lightening in color occurring. Such a charge compensation also already takes place during the flow of current inside the electrolyte volume.

The electrochromic system according to the invention preferably comprises at least one electrochromic substance of the formula (I)

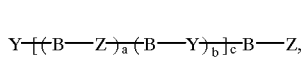

(I)

in which
Y and Z independently of one another represent a radical $OX_2$ or $RED_1$, but in which at least one Y represents $OX_2$ and at least one Z represents $RED_1$,
in which
$OX_2$ represents the radical of a reversibly electrochemically reducible redox system and
$RED_2$ represents the radical of a reversibly electrochemically oxidizable redox system,
B represents a bridge member,
c represents an integer from 0 to 5 and
a and b independently of one another represent an integer from 0 to 5, and preferably represent an integer from 0 to 3.

The electrochromic system preferably comprises at least one electrochromic substance of the formula (I) in which
Y represents $OX_2$ and Z represents $RED_1$ and Y and Z alternate in their sequence.

The electrochromic system according to the invention particularly preferably comprises at least one electrochromic substance of the formulae $$OX_2\text{—}B\text{—}RED_1, \quad (Ia)$$

$$OX_2\text{—}B\text{—}RED_1\text{—}B\text{—}OX_2, \quad (Ib)$$

$$RED_1\text{—}B\text{—}OX_2\text{—}B\text{—}RED_1, \quad \text{or} \quad (Ic)$$

$$OX_2\text{—}(B\text{—}RED_1\text{—}B\text{—}OX_2)_d\text{—}B\text{—}RED_1, \quad (Id)$$

in which $OX_2$, $RED_1$ and B have the abovementioned meaning and d represents an integer from 1 to 5.

The electrochromic system according to the invention especially preferably comprises at least one electrochromic substance of the formulae (Ia)–(Id)

in which $OX_2$ represents the radical of a cathodically reducible substance which, in the cyclic voltammogram recorded in an inert solvent at room temperature, shows at least two chemically reversible reduction waves, the first of these reduction waves leading to an increase in the extinction at not less than one wavelength in the visible range of the electromagnetic spectrum, $RED_1$ represents the radical of the anodically reversibly oxidizable substance which, in the cyclic voltammogram recorded in an inert solvent at room temperature, shows at least two chemically reversible oxidation waves, the first of these oxidation waves leading to an increase in the extinction at not less than one wavelength in the visible range of the electromagnetic spectrum and B represents a bridge member.

An electrochromic system according to the invention which is particularly preferred is one which comprises at least one substance of the formula (Ia)–(Id), in which $OX_2$ represents a radical of the formulae

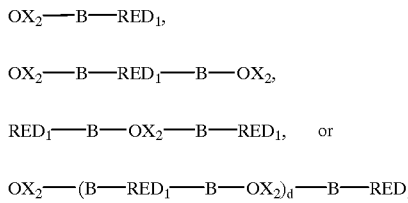

(II)

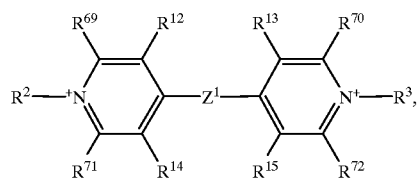

(III)

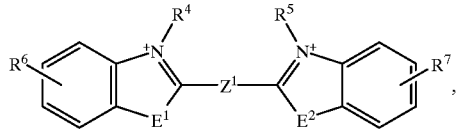

(IV)

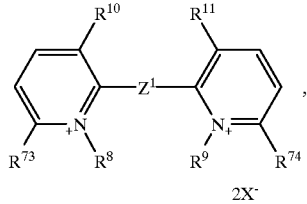

(V)

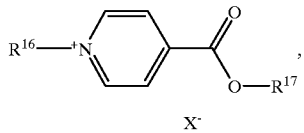

(VI)

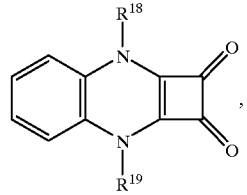

(VII)

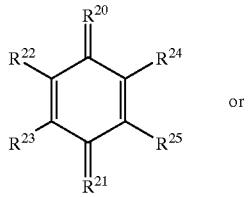

(VIII)

or

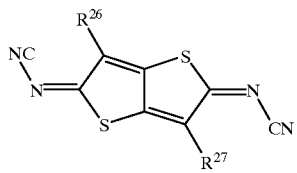

(IX)

in which $R^2$ to $R^5$, $R^8$, $R^9$ and $R^{16}$ to $R^{19}$ independently of one another denote $C_1$- to $C_{18}$-alkyl, $C_2$- to $C_{12}$-alkenyl, $C_3$- to $C_7$-cycloalkyl, $C_7$- to $C_{15}$-aralkyl or $C_6$- to $C_{10}$-aryl or $R^4$ and $R^5$ or $R^8$ and $R^9$ together form a —$(CH_2)_2$— or —$(CH_3)$— bridge, $R^6$, $R^7$ and $R^{22}$ to $R^{25}$ independently of one another denote hydrogen, $C_1$- to $C_4$-alkyl, $C_1$- to $C_4$-alkoxy, halogen, cyano, nitro or $C_1$- to $C_4$-alkoxycarbonyl or $R^{22}$ and $R^{23}$ and/or $R^{24}$ and $R^{25}$ form a —CH=CH— bridge, $R^{10}$ and $R^{11}$; $R^{12}$ and $R^{13}$; and $R^{14}$ and $R^{15}$ independently of one another denote hydrogen or, in pairs, a —$(CH_2)_2$—, —$(CH_2)_3$— or —CH=CH— bridge, $R^{20}$ and $R^{21}$ independently of one another denote O, N—CN, $C(CN)_2$ or N—$C_6$— to $C_{10}$-aryl, $R^{26}$ denotes hydrogen, $C_1$- to $C_4$-alkyl, $C_1$- to $C_4$-alkoxy, halogen, cyano, nitro, $C_1$- to $C_4$-alkoxycarbonyl or $C_6$- to $C_{10}$-aryl, $R^{69}$ to $R^{74}$ independently of one another denote hydrogen or $C_1$–$C_6$-alkyl, or $R^{69}$; $R^{12}$ and/or $R^{70}$; and $R^{13}$ form a —CH=CH—CH=CH— bridge, $E^1$ and $E^2$ independently of one another denote O, S, $NR^1$ or $C(CH_3)_2$ or $E^1$ and $E^2$ together form a —N—$(CH_2)_2$—N— bridge, $R^1$ denotes $C_1$- to $C_{18}$-alkyl, $C_2$- to $C_{12}$-alkenyl, $C_4$- to $C_7$-cycloalkyl, $C_7$- to $C_{15}$-aralkyl or $C_6$- to $C_{10}$-aryl, $Z^1$ denotes a direct bond —CH=CH—, —C(CH$_3$)=CH—, —C(CN)=CH—, —CCl=CCl—, —C(OH)=CH—, —CCl=CH—, —C≡C—, —CH=N—N=CH—, —C(CH$_3$)=N—N=C(CH$_3$)— or —CCl=N—N=CCl—, $Z^2$ denotes —$(CH_2)_r$— or —$CH_2$—$C_6H_4$—$CH_2$—, r denotes an integer from 1 to 10, $X^-$ denotes an anion which is redox-inert under the conditions, wherein bonding to the bridge member B is effected via one of the radicals $R^2$–$R^{19}$, $R^{22}$–$R^{27}$ or, in the case where $E^1$ or $E^2$ represents $NR^1$, via $R^1$ and the radicals mentioned then represent a direct bond, $RED_1$ represents one of the following radicals

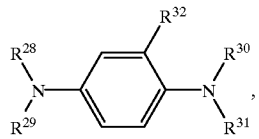 (X)

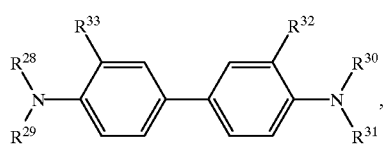 (XI)

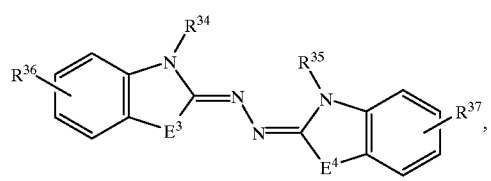 (XII)

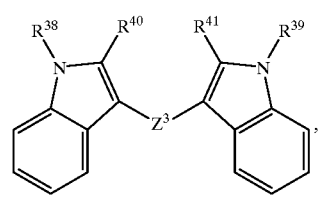 (XIII)

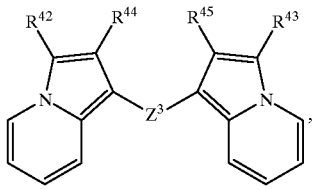 (XIV)

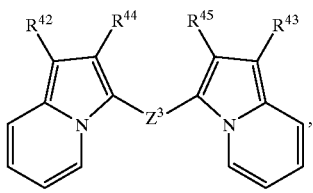 (XV)

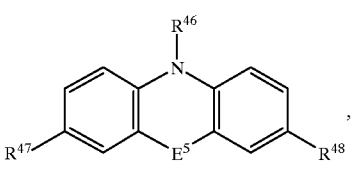 (XVI)

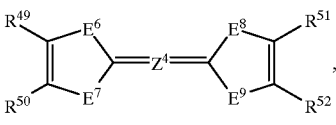 (XVII)

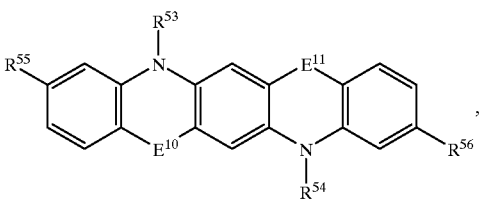 (XVIII)

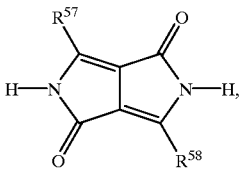 (XIX)

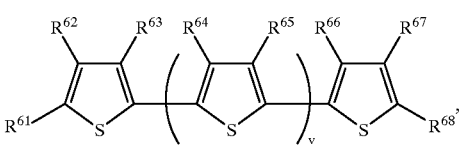 (XX)

wherein $R^{28}$ to $R^{31}$, $R^{34}$, $R^{35}$, $R^{38}$, $R^{39}$, $R^{46}$, $R^{53}$ and $R^{54}$ independently of one another denote $C_1$- to $C_{18}$-alkyl, $C_2$- to $C_{12}$-alkenyl, $C_3$- to $C_7$-cycloalkyl, $C_7$- to $C_{15}$-aralkyl or $C_6$- to $C_{10}$-aryl, and $R^{46}$, $R^{53}$ and $R^{54}$ additionally denote hydrogen, $R^{32}$, $R^{33}$, $R^{36}$, $R^{37}$, $R^{40}$, $R^{41}$, $R^{42}$ to $R^{45}$, $R^{47}$, $R^{48}$, $R^{49}$ to $R^{52}$ and $R^{55}$ to $R^{57}$ independently of one another denote hydrogen, $C_1$- to $C_4$-alkyl, $C_1$- to $C_4$-alkoxy, halogen, cyano, nitro, $C_1$- to $C_4$-alkoxycarbonyl or $C_6$- to $C_{10}$-aryl and $R^{57}$ and $R^{58}$ additionally denote an optionally benzo-fused aromatic or quasiaromatic five- or six-membered heterocyclic ring and $R^{48}$ additionally denotes $NR^{75}R^{76}$, $R^{49}$ and $R^{50}$ and/or $R^{51}$ and $R^{52}$ form a —$(CH_2)_3$—, —$(CH_2)_4$—, —$(CH_2)_5$— or —CH=CH—CH=CH— bridge, $Z^3$ denotes a direct bond or a —CH=CH— or —N=N— bridge, =$Z^4$= denotes a direct double bond or a =CH—CH= or =N—N= bridge $E^3$ to $E^5$, $E^{10}$ and $E^{11}$ independently of one another denote O, S, $NR^{59}$ or $C(CH_3)_2$ and $E^5$ additionally denotes C=O or $SO_2$, or $E^3$ and $E^4$ independently of one another denote —CH=CH—, $E^6$ to $E^9$ independently of one another denote S, Se or $NR^{59}$, $R^{59}$, $R^{75}$ and $R^{76}$ independently of one another denote $C_1$- to $C_{12}$-alkyl, $C_2$- to $C_8$-alkenyl, $C_3$ to $C_7$-cycloalkyl, $C_7$- to $C_{15}$-aralkyl or $C_6$- to $C_{10}$-aryl and $R^{73}$ additionally denotes hydrogen, or $R^{73}$ and $R^{74}$ in the meaning of $NR^{73}R^{74}$, together with the N atom to which they are bonded, form a five- or six-membered saturated ring which can contain further heteroatoms, $R^{61}$ to $R^{68}$ independently of one another denote hydrogen, $C_1$- to $C_6$-alkyl, $C_1$- to $C_4$-alkoxy, cyano, $C_1$- to $C_4$-alkoxycarbonyl or $C_6$- to $C_{10}$-aryl, or $R^{61}$; $R^{62}$ and $R^{67}$; and $R^{68}$ independently of one another together form a —$(CH_2)_3$—, —$(CH_2)_4$— or —CH=CH—CH=CH— bridge, v denotes an integer between 0 and 10, wherein bonding to the bridge member B is effected by one of the radicals $R^{28}$–$R^{58}$, $R^{61}$, $R^{62}$, $R^{67}$, $R^{68}$ or, in the case where one of the radicals $E^3$–$E^{11}$ represents $NR^{59}$, via $R^{59}$ and the radicals mentioned then represent a direct bond, and B represents a bridge member of the formula —$(CH_2)_n$— or —[$Y^1_s(CH_2)_m$—$Y^2$]$_o$—$(CH_2)_p$—$Y^3_q$—, each of which is optionally substituted by $C_1$- to $C_4$-alkoxy, halogen or phenyl, $Y^1$ to $Y^3$ independently of one another represents O, S, $NR^{60}$, COO, CONH, NHCONH, cyclopentanediyl, cyclohexanediyl, phenylene or naphthylene, $R^{60}$ denotes $C_1$- to $C_6$-alkyl, $C_2$- to $C_6$-alkenyl, $C_4$- to $C_7$-cycloalkyl, $C_7$- to $C_{15}$-aralkyl or $C_6$- to $C_{10}$-aryl, n denotes an integer from 1 to 12, m and p independently of one another denote an integer-from 0 to 8, o denotes an integer from 0 to 6 and q and s independently of one another denote 0 or 1.

An electrochromic system according to the invention which is especially preferred is one which comprises at least one substance of the formula (Ia)–(Id)

in which $OX_2$ represents a radical of the formulae (II), (III), (IV) or (V), in which $R^2$, $R^3$, $R^4$, $R^5$, $R^8$ and $R^9$ independently of one another represent $C_1$- to $C_{12}$-alkyl, $C_2$- to $C_8$-alkenyl, $C_5$- to $C_7$-cycloalkyl, $C_7$- to $C_{15}$-aralkyl or $C_6$- to $C_{10}$-aryl, $R^6$ and $R^7$ independently of one another represent hydrogen, methyl, ethyl, methoxy, ethoxy, fluorine, chlorine, bromine, cyano, nitro, methoxycarbonyl or ethoxycarbonyl, $R^{10}$, $R^{11}$; $R^{12}$, $R^{13}$ and $R^{14}$, $R^{15}$ independently of one another represent hydrogen or, if $Z^1$ denotes a direct bond, in each case together represent a —$(CH_2)_2$—, —$(CH_2)_3$- or —CH=CH— bridge, or $R^4$, $R^5$ and $R^8$, $R^9$ independently of one another in pairs together represent a —$(CH_2)_2$— or —$(CH_3)_3$— bridge, if $Z^1$ denotes a direct bond, $R^{69}$ to $R^{74}$ independently of one another denote hydrogen or $C_1$–$C_4$-alkyl, $E^1$ and $E^2$ are identical and represent O, S, $NR^1$ or $C(CH_3)_2$ or together form a —N—$(CH_2)_2$—N— bridge, $R^1$ represents $C_1$- to $C_{12}$-alkyl, $C_2$- to $C_4$-alkenyl, $C_5$- to $C_7$-cycloalkyl, $C_7$- to $C_{15}$-aralkyl or $C_6$- to $C_{10}$-aryl, $Z^1$ represents a direct bond, —CH=CH—, —$C(CH_3)$=CH—, —C(CN)=CH—, —C≡C— or —CH=N—N=CH—, $Z^2$ represents —(CH)$_r$— or —$CH_2$—$C_6H_4$—$CH_2$—, r represents an integer between 1 and 6, $X^-$ represents a colorless anion which is redox-inert under the conditions, wherein bonding to the bridge member B is effected by one of the radicals $R^2$–$R^{11}$ or, in the case where $E^1$ or $E^2$ represents $NR^1$, via $R^1$ and the radicals mentioned then represent a direct bond, $RED_1$ represents a radical of the formulae (X), (XI), (XII), (XIII), (XVI), (XVII), (XVIII) or (XX), in which $R^{28}$ to $R^{31}$, $R^{34}$, $R^{35}$, $R^{38}$, $R^{39}$, $R^{46}$, $R^{53}$ and $R^{54}$ independently of one another denote $C_1$- to $C_{12}$-alkyl, $C_2$- to $C_8$-alkenyl, $C_5$- to $C_7$-cycloalkyl, $C_7$- to $C_{15}$-aralkyl or $C_6$- to $C_{10}$-aryl and $R^{46}$, $R^{53}$ and $R^{54}$ additionally denote hydrogen, $R^{32}$, $R^{33}$, $R^{36}$, $R^{37}$, $R^{40}$, $R^{41}$, $R^{47}$ to $R^{52}$, $R^{55}$ and $R^{56}$ independently of one another denote hydrogen, methyl, ethyl, methoxy, ethoxy, fluorine, chlorine, bromine, cyano, nitro, methoxycarbonyl, ethoxycarbonyl or phenyl and $R^{57}$ and $R^{58}$ additionally denote 2- or 4-pyridyl and $R^{48}$ additionally denotes $NR^{75}R^{76}$, $Z^3$ denotes a direct bond or a —CH=CH— or —N=N— bridge, =$Z^4$= denotes a direct bond or a =CH—CH= or =N—N= bridge, $E^3$ to $E^5$, $E^{10}$ and $E^{11}$ independently of one another denote O, S, $NR^{59}$ or $C(CH_3)_2$, but $E^3$ and $E^4$ have the same meaning, $E^6$ to $E^9$ are identical to one another and denote S, Se or $NR^{59}$ and $E^5$ additionally denotes C=O, $E^6$ represents $NR^{59}$, in which $R^{59}$ denotes a direct bond to the bridge B and $E^7$ to $E^9$ have the abovementioned meaning but must not be identical to one another, $R^{59}$, $R^{75}$ and $R^{76}$ independently of one another denote $C_1$- to $C_{12}$-alkyl, $C_2$- to $C_8$-alkenyl, $C_5$- to $C_7$-cycloalkyl, $C_7$- to $C_{15}$-aralkyl or $C_6$- to $C_{10}$-aryl, and $R^{73}$ additionally denotes hydrogen or $R^{73}$ and $R^{74}$ in the meaning $NR^{73}R^{74}$, together with the N atom to which they are bonded, denote pyrrolidino, piperidino or morpholino, $R^{61}$, $R^{62}$ and $R^{67}$, $R^{68}$ independently of one another represent hydrogen, $C_1$- to $C_4$- allyl, methoxycarbonyl, ethoxycarbonyl or phenyl or in pairs together represent a —$(CH_2)_3$— or —$(CH_2)_4$— bridge, $R^{63}$ to $R^{66}$ represents hydrogen and v represents an integer from 1 to 6, wherein bonding to the bridge member B is effected by one of the radicals $R^{28}$–$R^{41}$, $R^{46}$–$R^{56}$, $R^{61}$, $R^{62}$, $R^{67}$, $R^{68}$ or, in the case where one of the radicals $E^3$–$E^{11}$ represents $NR^{59}$, via $R^{59}$ and the radicals mentioned then represent a direct bond, B represents a bridge member of the formulae —$(CH_2)_n$—, —$(CH_2)_m$—O—$(CH_2)_p$—, —$(CH)_m$—$NR^{60}$—$(CH_2)_p$—, —$(CH_2)_m$—$C_6H_4$—$(CH_2)_p$—, —[O—$(CH_2)_p]_o$—O—, —[$NR^{60}$—$(CH_2)_p]_o$—$NR^{60}$—, —[$C_6H_4$—$(CH_2)_p]_o$—$C_6H_4$—, —$(CH_2)_m$OCO—$C_6H_4$—COO—$(CH_2)_p$—, —$(CH_2)_m$NHCO—$C_6H_4$—CONH—$(CH_2)_p$—, —$(CH_2)_m$—NHCONH—$C_6H_4$—NHCONH—$(CH_2)_p$—, —$(CH_2)_m$—OCO—$(CH_2)_t$—COO—$(CH_2)$—, —$(CH_2)_m$—NHCO—$(CH_2)_t$ CONH—$(CH)_p$—, —$(CH_2)_m$—NHCONH—$(CH_2)_t$—NHCONH—$(CH_2)_p$—, $R_{60}$ represents methyl, ethyl, benzyl or phenyl, n represents an integer from 1 to 10, m and p independently of one another represent an integer from 0 to 4, o represents an integer from 0 to 2 and t represents an integer from 1 to 6.

An electrochromic system according to the invention which is particularly preferred is one which comprises at least one substance of the formula (Ia)–(Id), in which $OX_2$ represents a radical of the formulae (II), (IV) or (V), in which $R^2$, $R^4$ and $R^8$ represent a direct bond to the bridge member B, $R^3$, $R^5$ and $R^9$ independently of one another represent methyl, ethyl, propyl, butyl, pentyl, hexyl, heptyl, octyl, benzyl or phenyl, or in the case of the formulae Ic or Id, also represent a direct bond to the bridge member B, $R^6$ and $R^7$ are identical or different and represent hydrogen, methyl, methody, chlorine, cyano or methoxycarbonyl, $R^{10}$, $R^{11}$; $R^{12}$, $R^{13}$ and $R^{14}$, $R^{15}$ independently of one another represent hydrogen or, if $Z^1$ denotes a direct bond, in each case in pairs together represent a —CH=CH— bridge, $R^{69}$ to $R^{72}$ are identical and denote hydrogen, methyl or ethyl, $R^{73}$ and $R^{74}$ denote hydrogen, $E^1$ and $E^2$ are identical and represent O or S, $Z^1$ represents a direct bond or —CH=CH—, $X^-$ represents a colorless anion which is redox-inert under the conditions, $RED_1$ represents a radical of the formulae (X), (XII), (XIII), (XVI) or (XVII), $R^{28}$, $R^{34}$, $R^{38}$, $R^{46}$ and $R^{49}$ represent a direct bond to the bridge member B, $R^{29}$ to $R^{31}$, $R^{35}$ and $R^{39}$ independently of one another represent methyl, ethyl, propyl, butyl, pentyl, hexyl, heptyl, octyl, benzyl or phenyl, or in the case of the formulae Ib or Id, $R^{30}$, $R^{35}$ and $R^{39}$ likewise represent the direct bond to the bridge member B, $R^{32}$, $R^{47}$ and $R^{48}$ represent hydrogen, $R^{36}$, $R^{37}$, $R^{40}$, $R^{41}$ and $R^{50}$ to $R^{52}$ independently of one another represent hydrogen, methyl, methoxy, chlorine, cyano, methoxycarbonyl or phenyl, or, in the case of the formulae Ib or Id, $R^{51}$ likewise represents a direct bond to the bridge member B, $Z^3$ represents a direct bond or a —CH=CH— or —N=N— bridge, =$Z^4$= represents a direct double bond or a =CH—CH= or =N—N= bridge, $E^3$ to $E^5$ independently of one another represent O, S or $NR^{59}$, but $E^3$ and $E^4$ have the same meaning, $E^6$ to $E^9$ are identical to one another and represent S, Se or $NR^{59}$, $R^{59}$ represents methyl, ethyl, propyl, butyl, pentyl, hexyl, heptyl, octyl, benzyl or phenyl, or in the case of the formula XVI in Ib or Id, likewise represents a direct bond to the bridge member B, B represents a bridge member of the formulae —$(CH_2)_n$—, —$(CH_2)_m$—O—$(CH_2)_p$—, —$(CH_2)_m$—$NR^{60}$—$(CH_2)_p$—, —$(CH_2)_m$—$C_6H_4$—$(CH_2)_p$—, —O—$(CH_2)_p$—O—, —$NR^{60}$—$(CH_2)_p$—$NR^{60}$—, —$(CH_2)_m$—OCO—$C_6H_4$—COO—$(CH_2)_p$—, —$(CH_2)_m$—NHCO—$C_6H_4$—CONH—$(CH_2)_p$—, —$(CH_2)_m$—NHCONH—$C_6H_4$—NHCONH—$(CH_2)_p$—, —$(CH_2)_m$—OCO—$(CH_2)_t$—COO—$(CH_2)_p$—, —$(CH_2)_m$—NHCO—$(CH_2)_t$—CONH—$(CH_2)_p$—, —$(CH_2)_m$—NHCONH—$(CH_2)_t$—NHCONH—$(CH_2)_p$—, $R^{60}$ represents methyl, n represents an integer from 1 to 10, m and p are identical and represent an integer from 0 to 2 and t represents an integer from 1 to 6.

An electrochromic system according to the invention which is especially preferred is one which comprises at least one substance of the formula (Ia) corresponding to one of the formulae

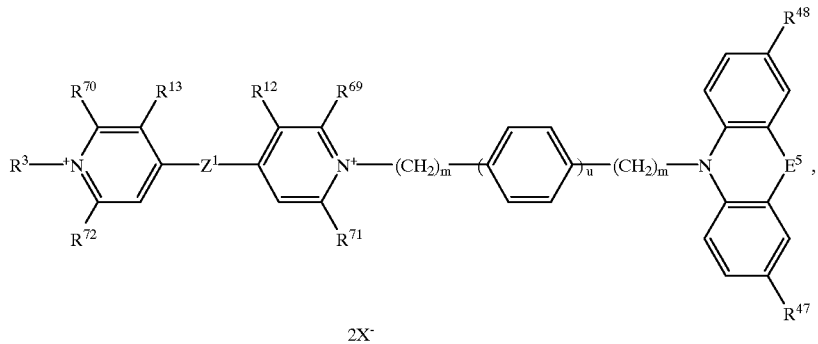
(XXI)
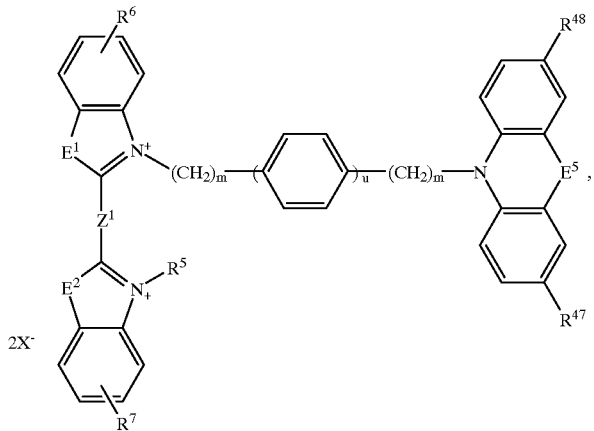
(XXII)
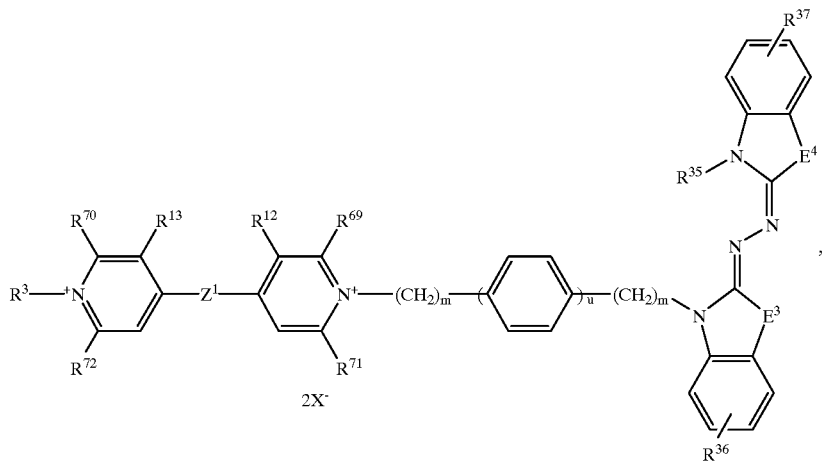
(XXIII)

-continued
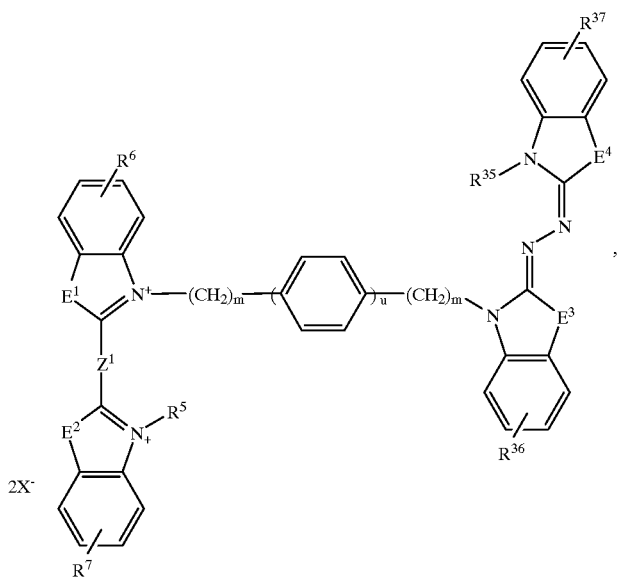
(XXIV)
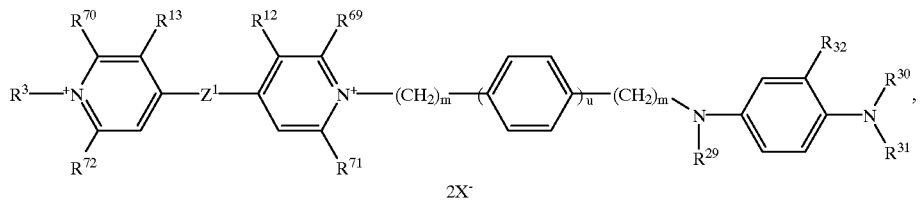
(XXV)
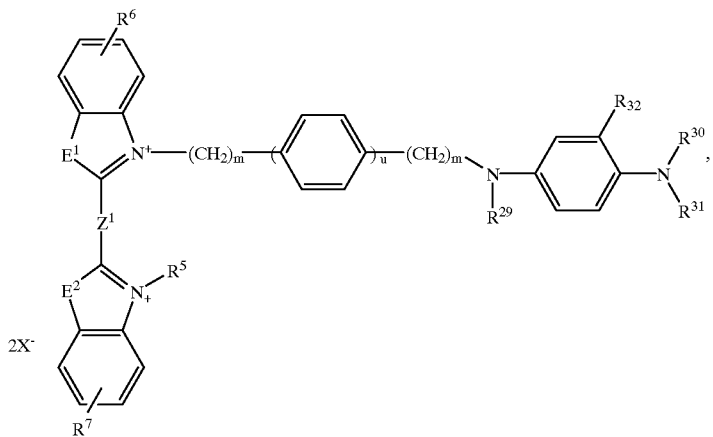
(XXVI)
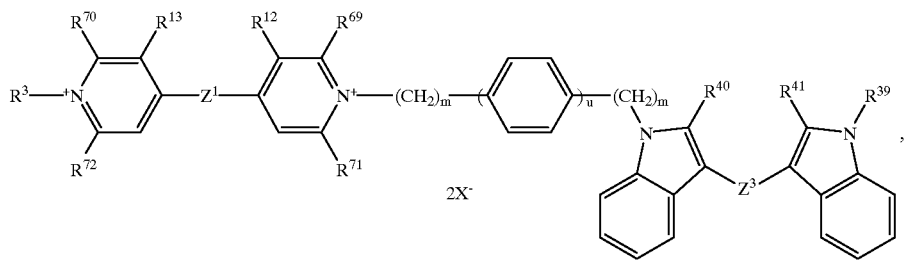
(XXVII)

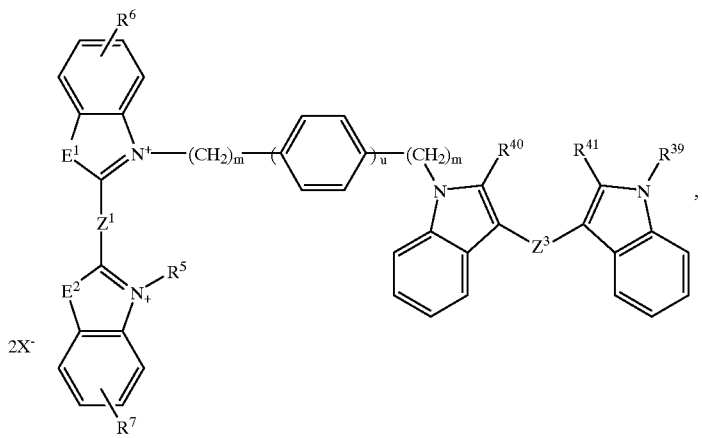
(XXVIII)
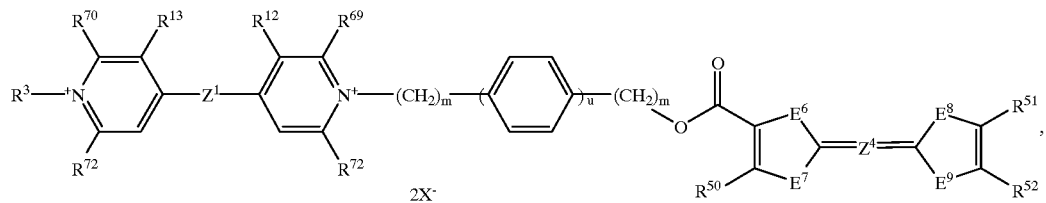
(XXIX)
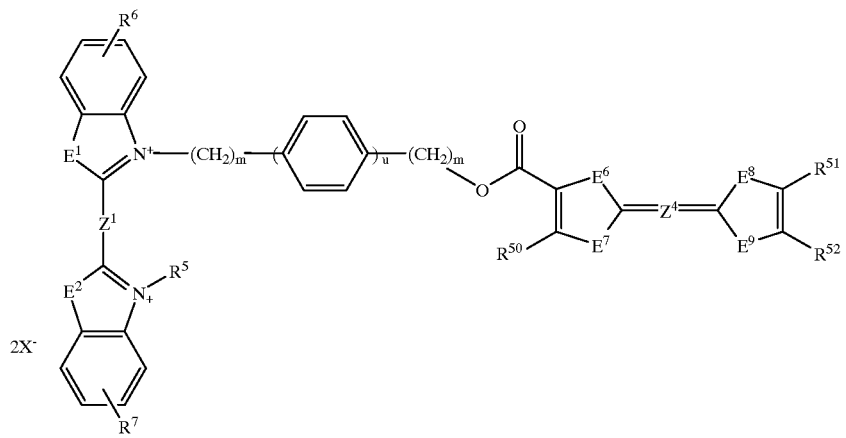
(XXX)
or at least one substance of the formula (Ib) corresponding to one of the formulae
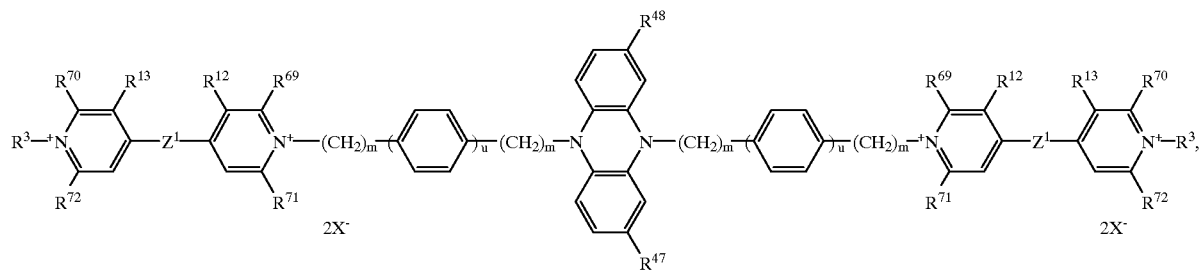
(XXXI)

-continued
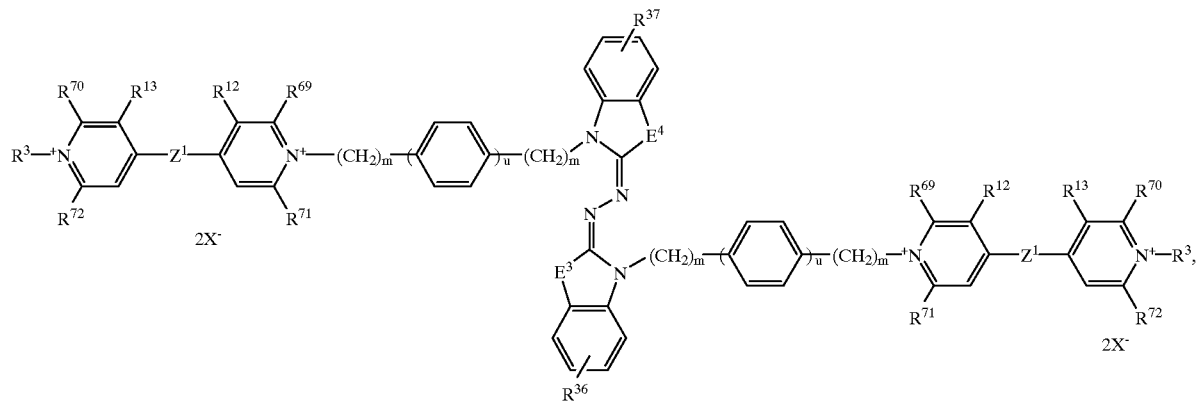
(XXXII)
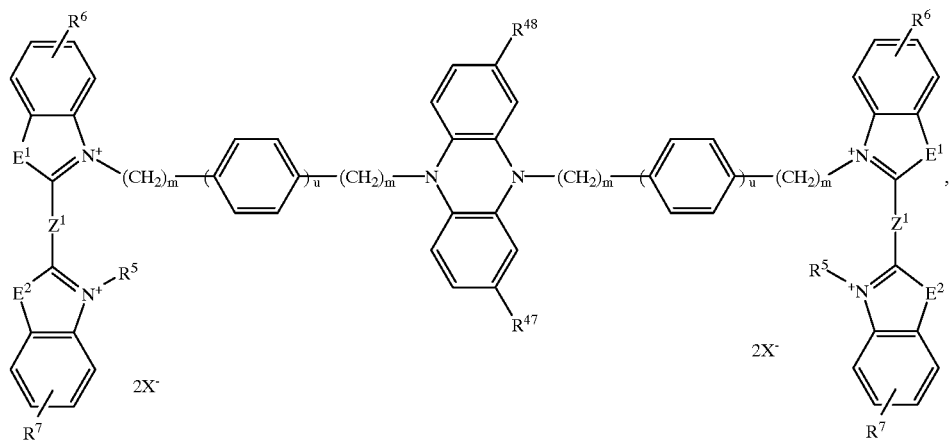
(XXXIII)
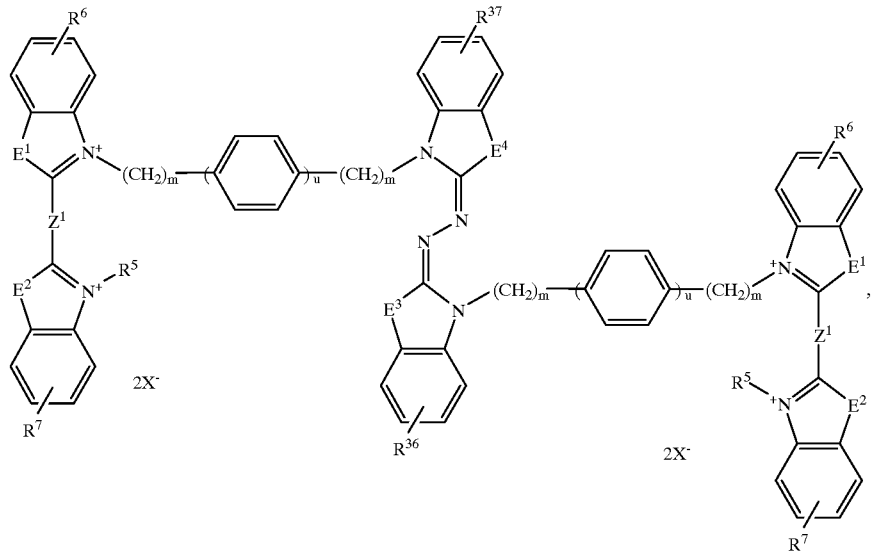
(XXXIV)

(XXXV)
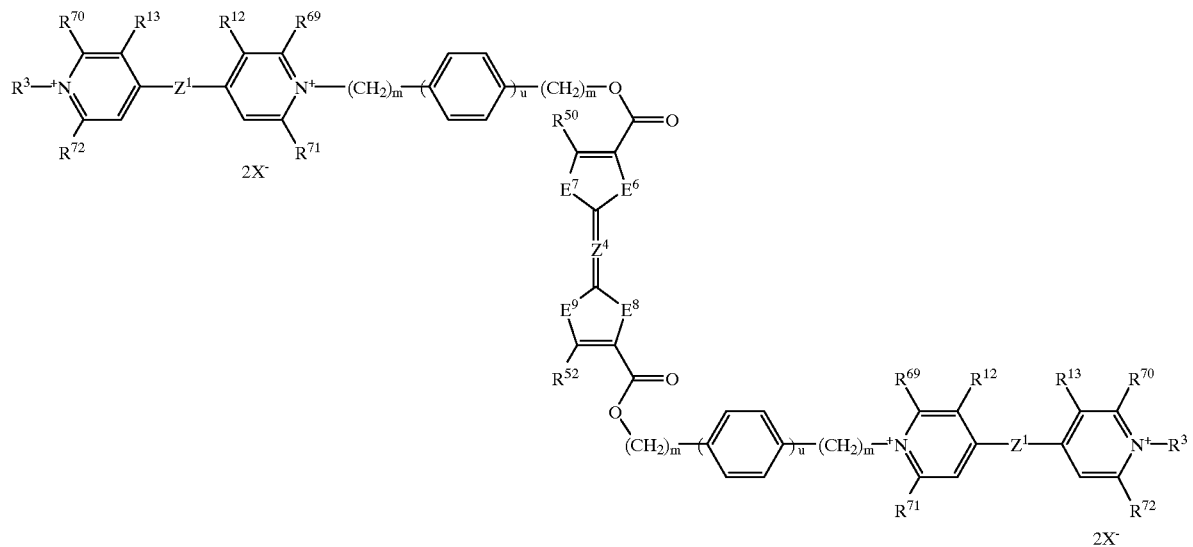
(XXXVI)
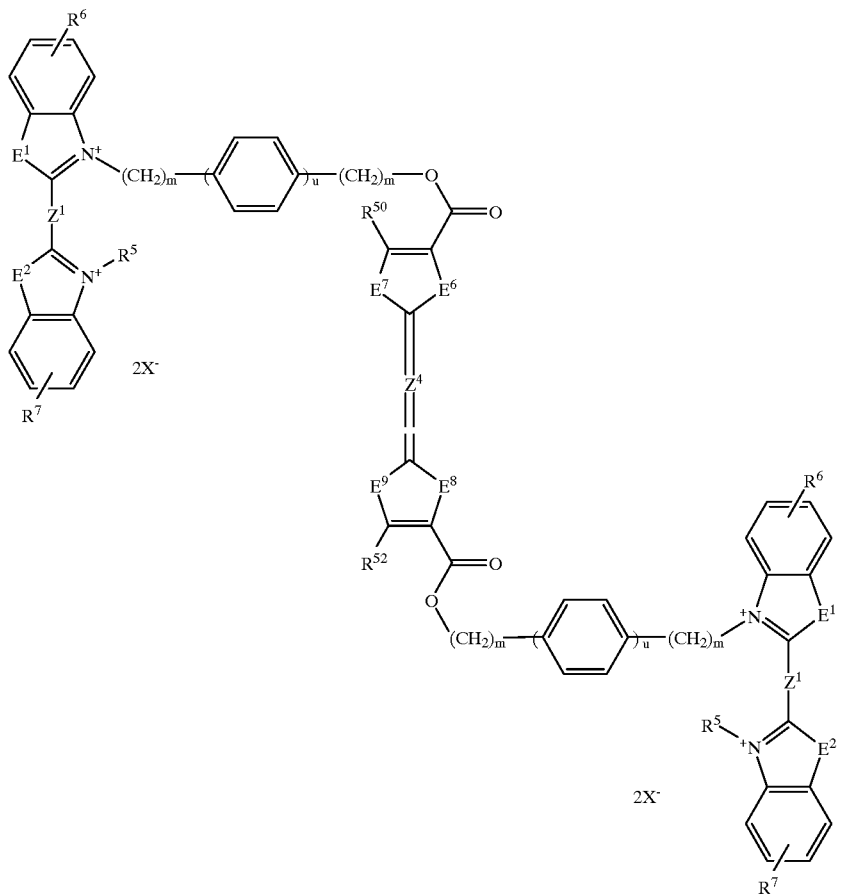

or at least one substance of the formula (Ic) corresponding to one of the formulae
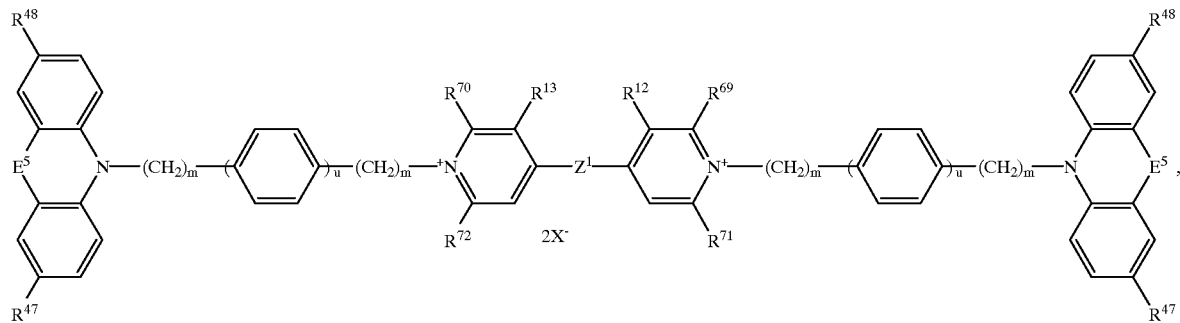
(XXXVII)
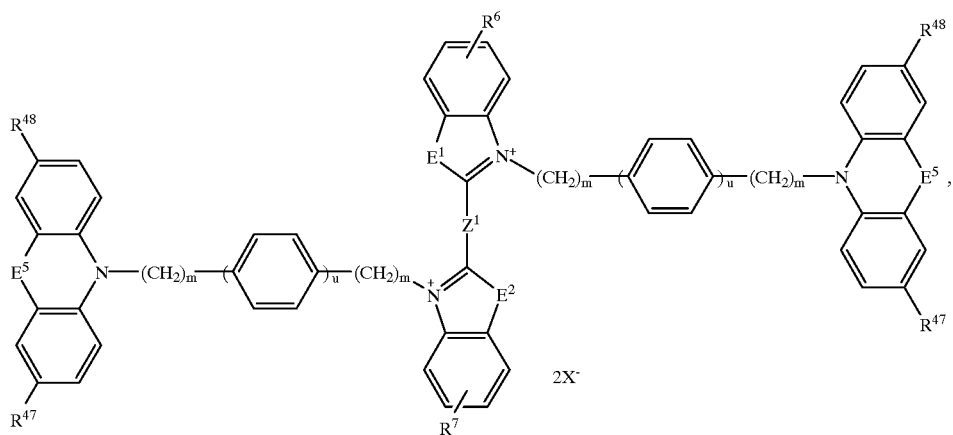
(XXXVIII)
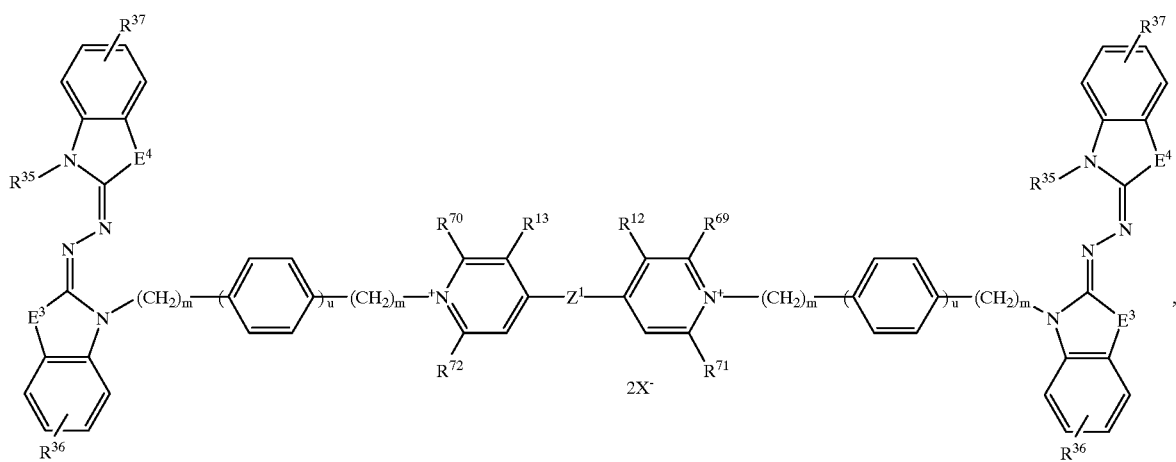
(XXXIX)

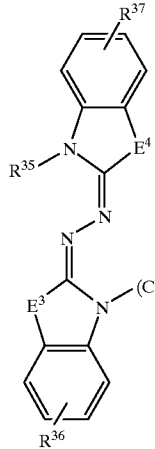
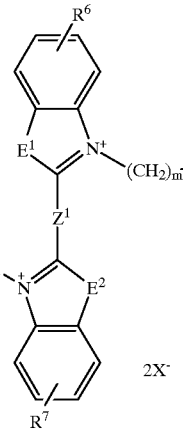
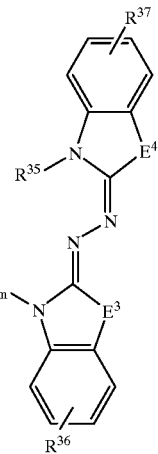
(XL)
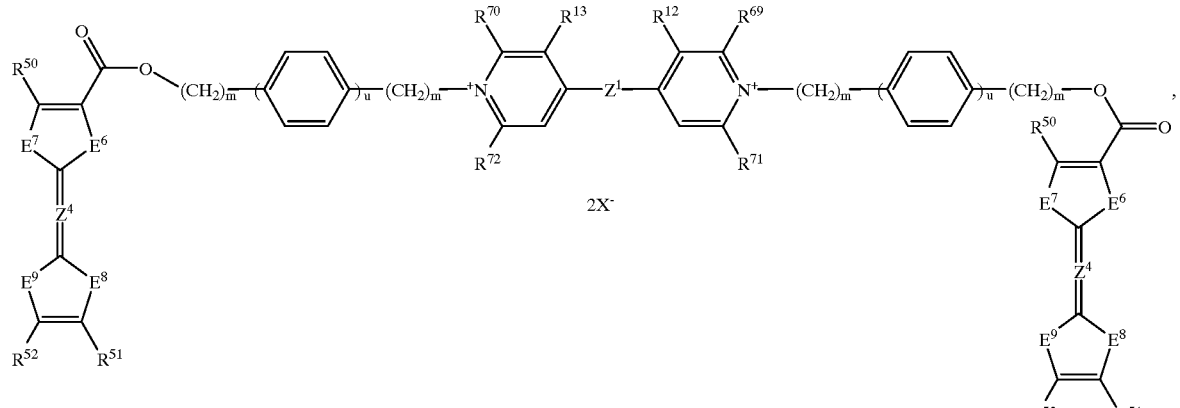
(XLI)
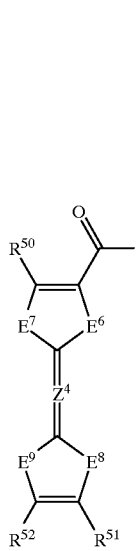
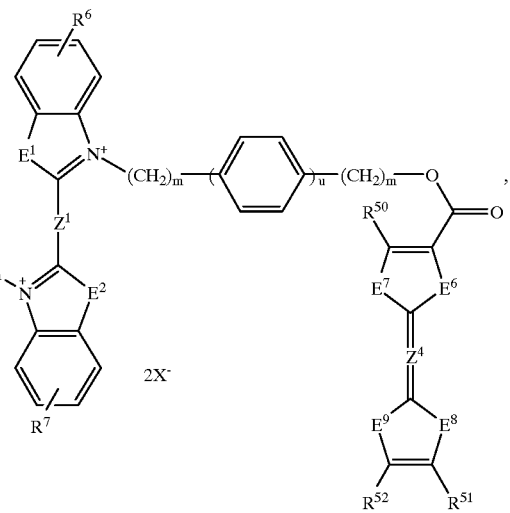
(XLII)

in which $R^3$, $R^5$, $R^{35}$ and $R^{39}$ independently of one another represent mnethyl, ethyl, propyl, butyl, pentyl, hexyl or benzyl, $R^6$, $R^7$ and $R^{36}$, $R^{37}$ in pairs are identical and represent hydrogen, methyl, methoxy, chlorine, cyano or methoxycarbonyl, $R^{12}$ and $R^{13}$ represent hydrogen or, if $Z^1$ denotes a direct bond, together represent a CH=CH bridge, $R^{69}$ to $R^{72}$ are identical and represent hydrogen or methyl, $E^1$ and $R^2$ are identical and represent O or S, $Z^1$ represents a direct bond or —CH=CH—, $R^{32}$, $R^{47}$ and $R^{48}$ represent hydrogen, $E^3$ to $E^5$ independently of one another represent O, S or $NR^{59}$, but where $E^3$ and $E^4$ are identical, $R^{29}$ to $R^{31}$ and $R^{59}$ independently of one another represent methyl, ethyl, propyl, butyl, pentyl, hexyl or benzyl, where $R^{29}$ to $R^{31}$ are preferably identical, $R^{40}$ and $R^{41}$ are identical and represent hydrogen, methyl, ethyl, propyl, butyl or phenyl, $Z^3$ represents a direct bond, —CH=CH— or —N=N—, $R^{50}$ to $R^{52}$ independently of one another represent hydrogen, methyl, methoxy, chlorine, cyano, methoxycarbonyl, ethoxycarbonyl or phenyl, but are preferably identical, $E^6$ to $E^9$ are identical to one another and represent S, Se or $NR^{59}$, $Z^4$ represents a direct double bond or a =CH—CH= or =N—N= bridge, m represents an integer from 1 to 5, u represents 0 or 1 and $X^-$ represents a colorless anion which is redox-inert under the conditions.

Electrochromic substances of the formula (I)

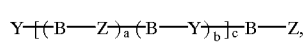  (I)

in which

Y and Z independently of one another represent a radical $OX_2$ or $RED_1$, but in which at least one Y represents $OX_2$ and at least one Z represents $RED_1$, in which $OX_2$ represents the radical of a reversibly electrochemically reducible redox system and $RED_1$ represents the radical of a reversibly electrochemically oxidizable redox system, but not a radical of the formula (XX), B represents a bridge member, c represents an integer from 0 to 5 and a and b independently of one another represent an integer from 0 to 5, and preferably represent an integer from 0 to 3, with the exception of compounds of the formula

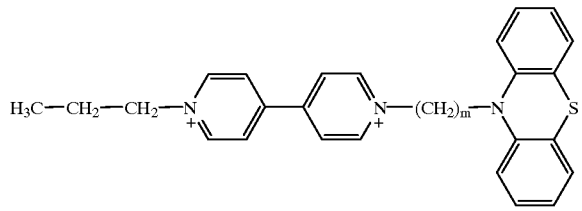

in which m represents an integer from 2 to 16 and $X^-$ has the abovementioned meaning, are novel and the present invention likewise relates to them.

Preferred electrochromic substances of the formula (I) are those which correspond to the formulae (Ia) to (Id)

 (Ia),

 (Ib),

 (Ic), or

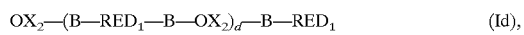 (Id), in which $OX_2$, $RED_1$ and B have the abovementioned general and preferred meanings and d represents an integer from 1 to 5.

Electrochromic substances of the formula (Ia) corresponding to the formulae

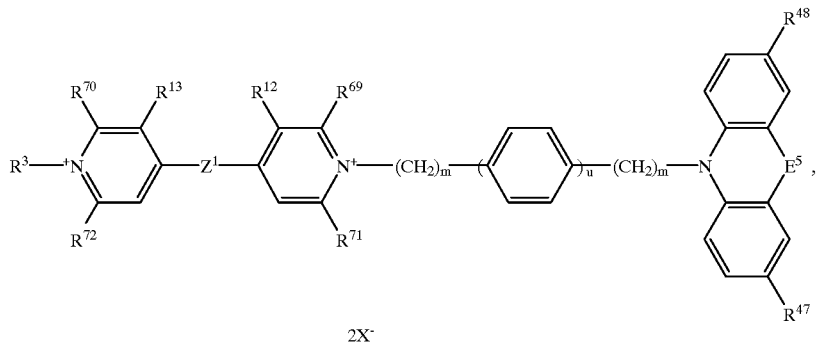

(XXI)

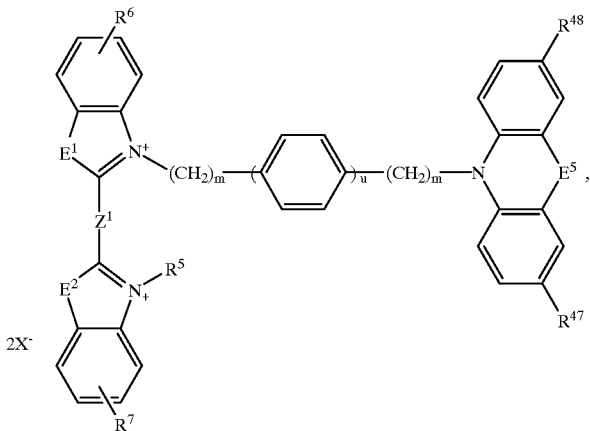
(XXII)
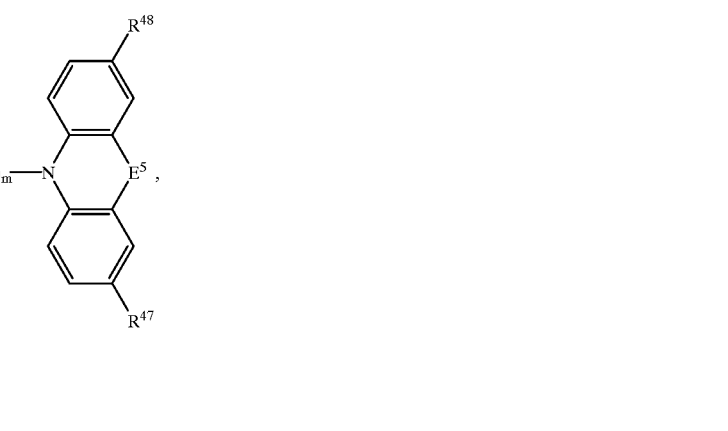
(XXIII)
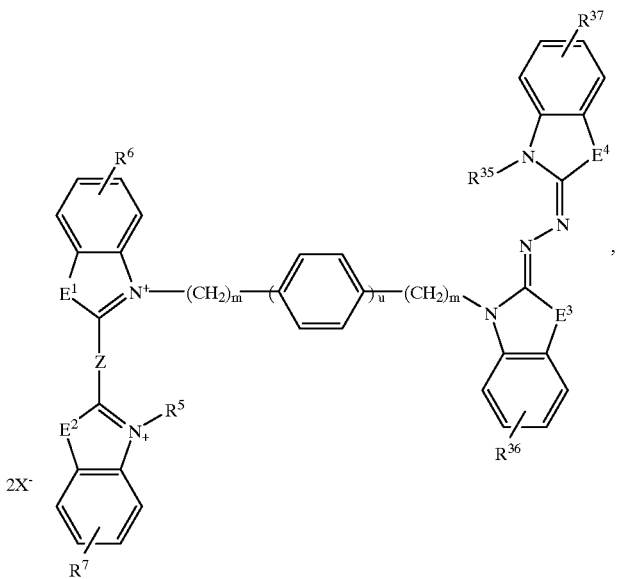
(XXIV)

-continued
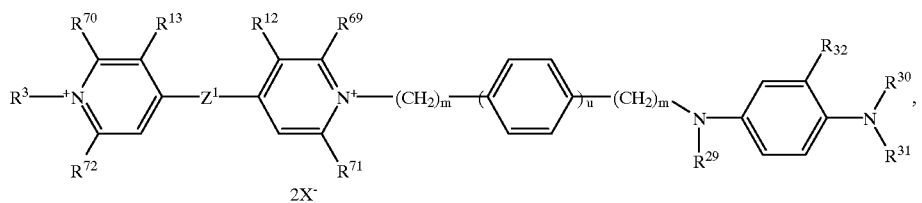
(XXV)
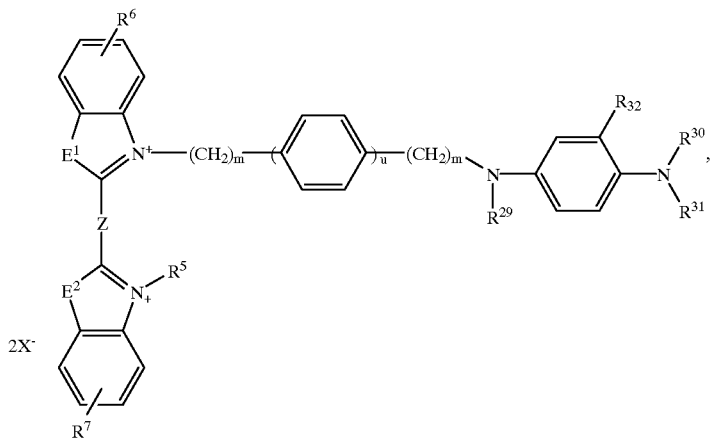
(XXVI)
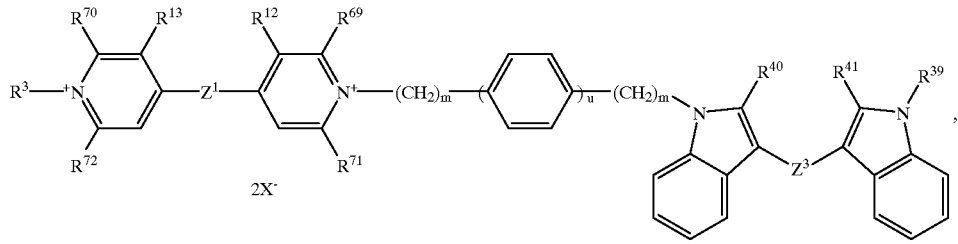
(XXVII)
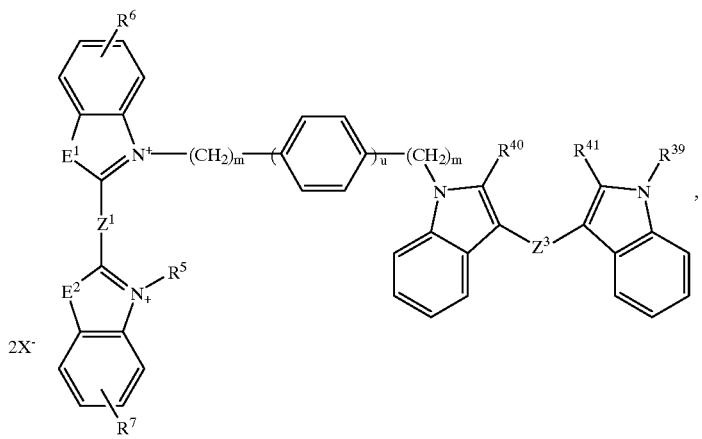
(XXVIII)
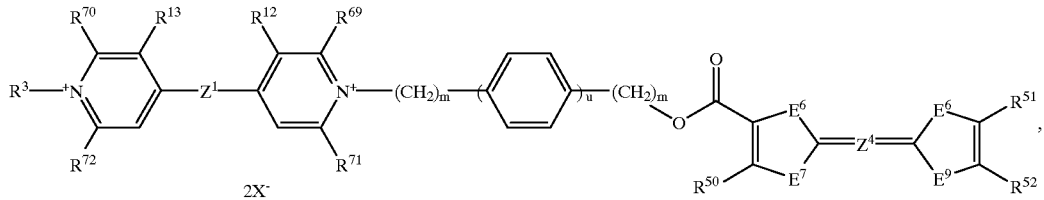
(XXIX)

(XXX)
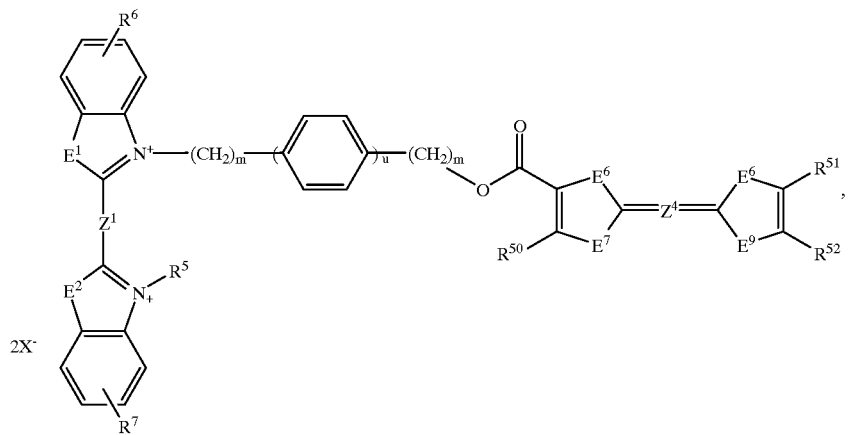
or electrochromic substances of the formula (Ib)
(XXXI)
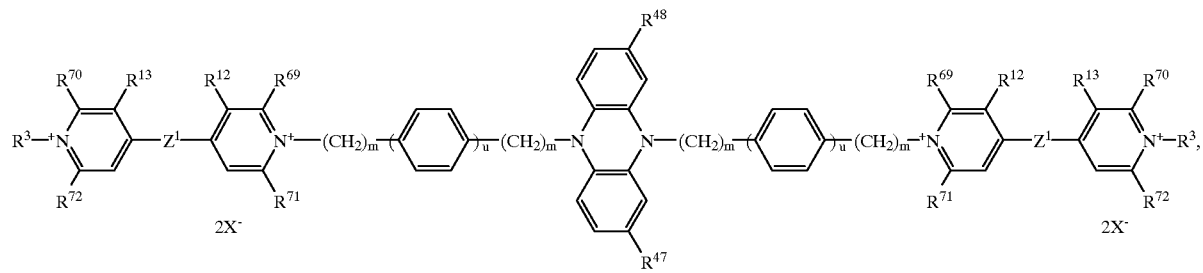
(XXXII)
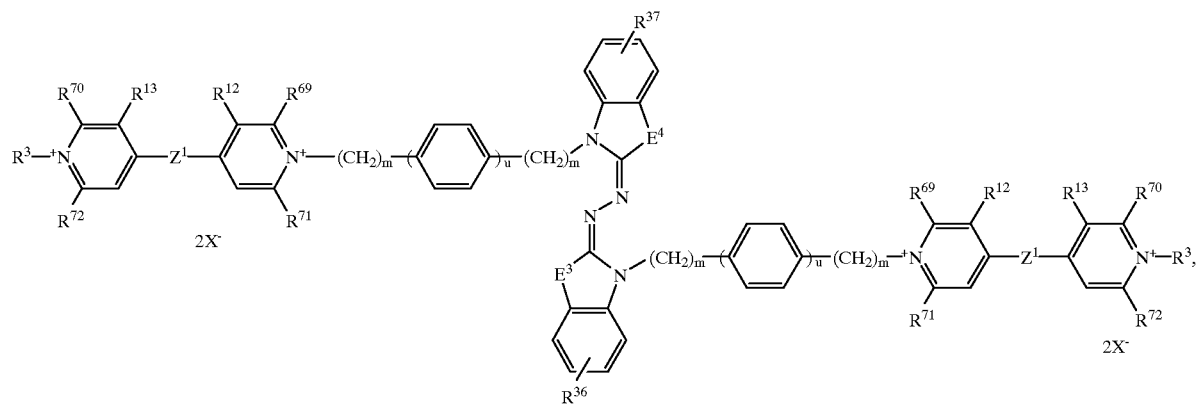

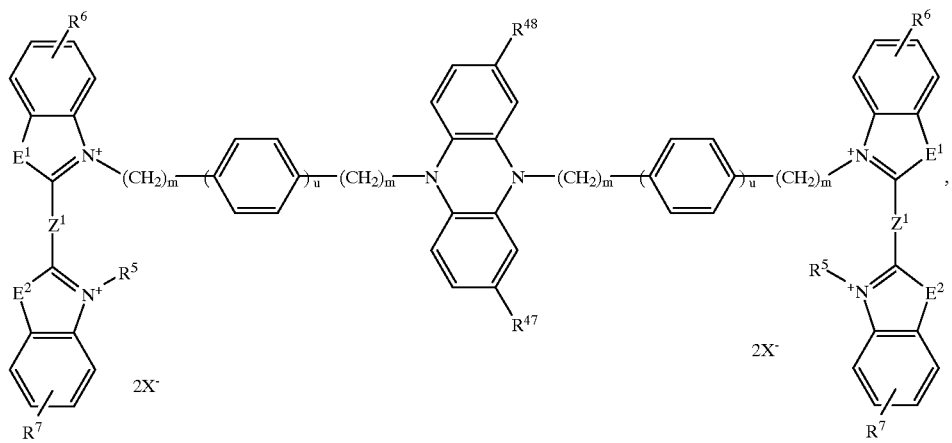
(XXXIII)
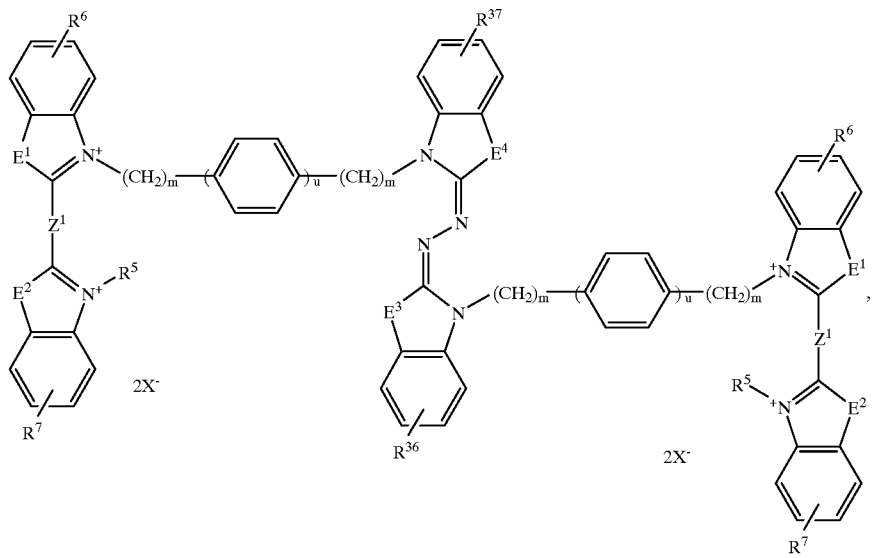
(XXXIV)
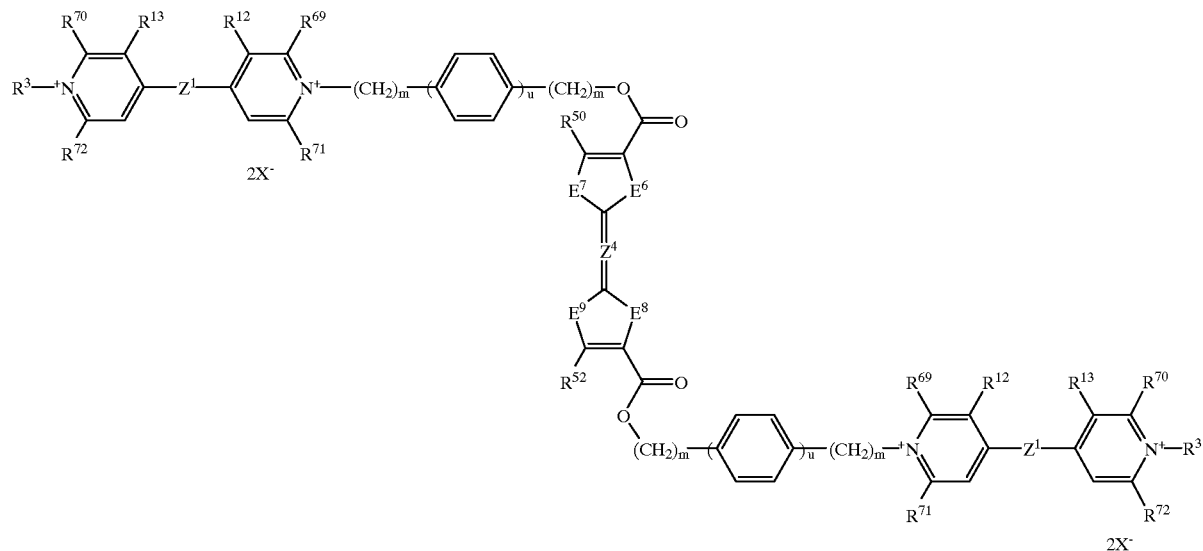
(XXXV)

(XXXVI)
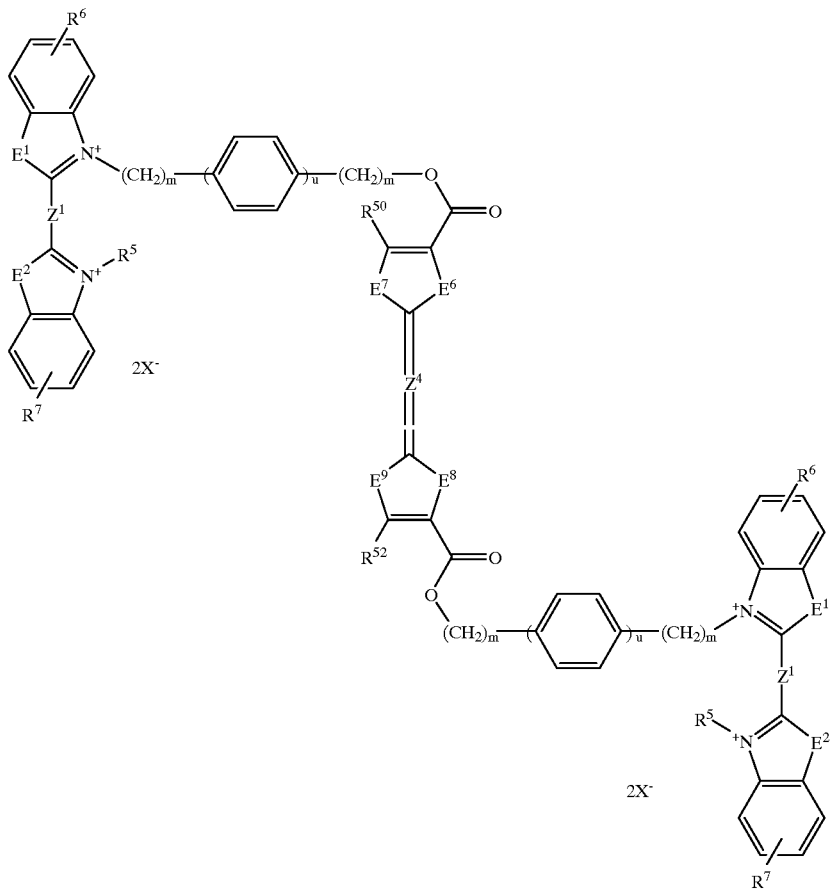
or electrochromic substances of the formula (Ic)
(XXXVII)
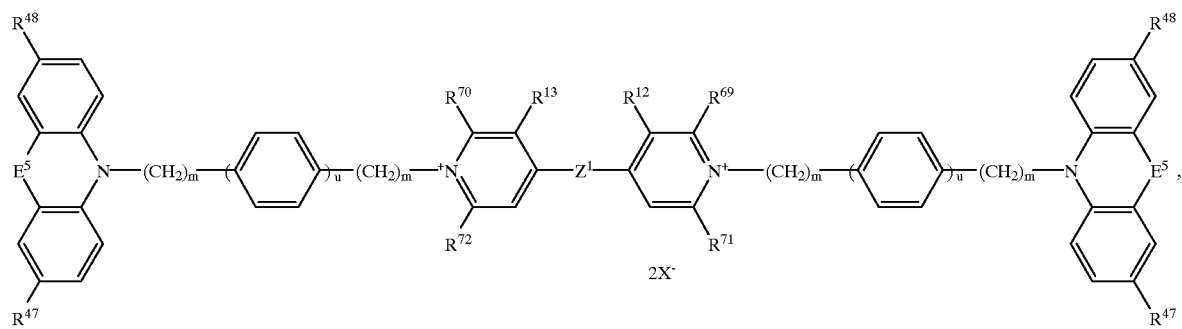

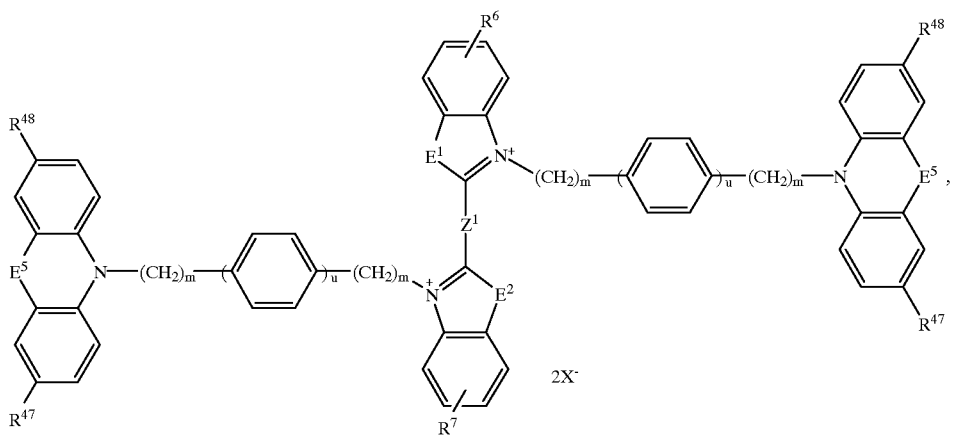
(XXXVIII)
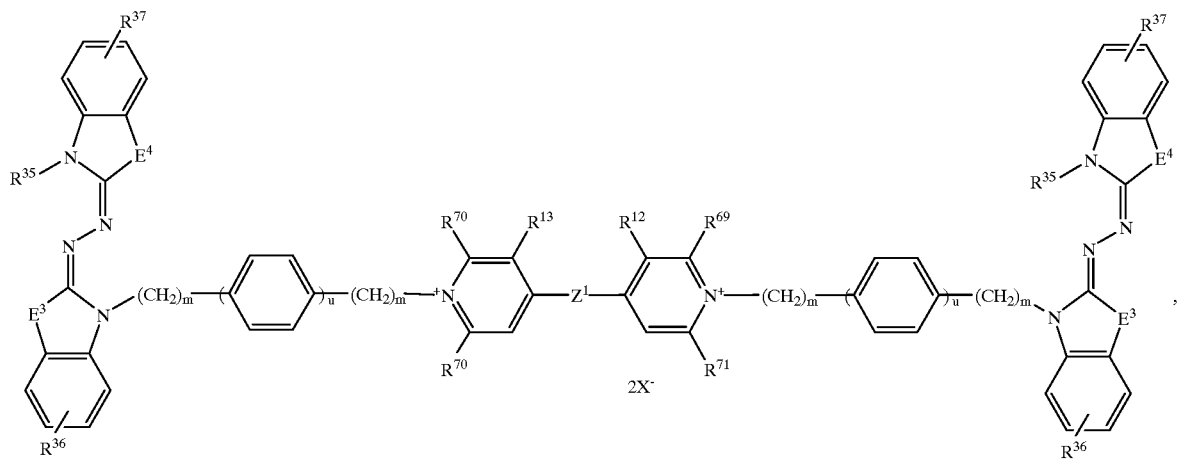
(XXXIX)
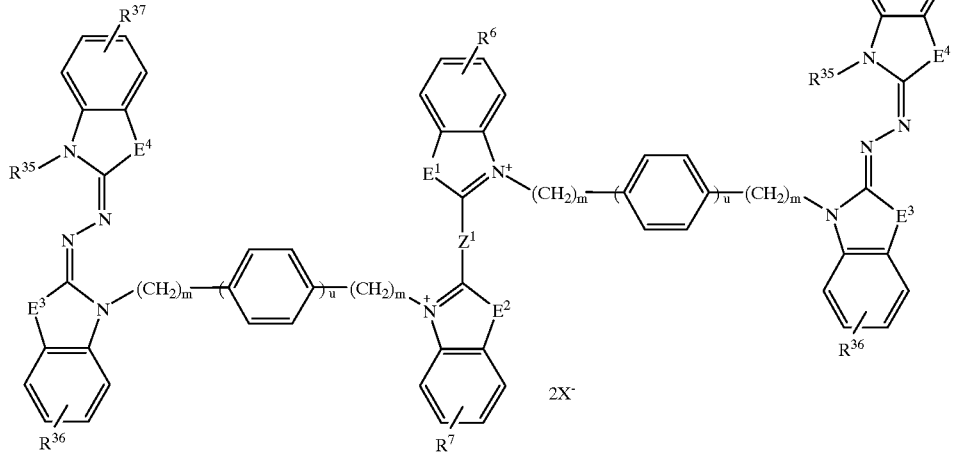
(XL)

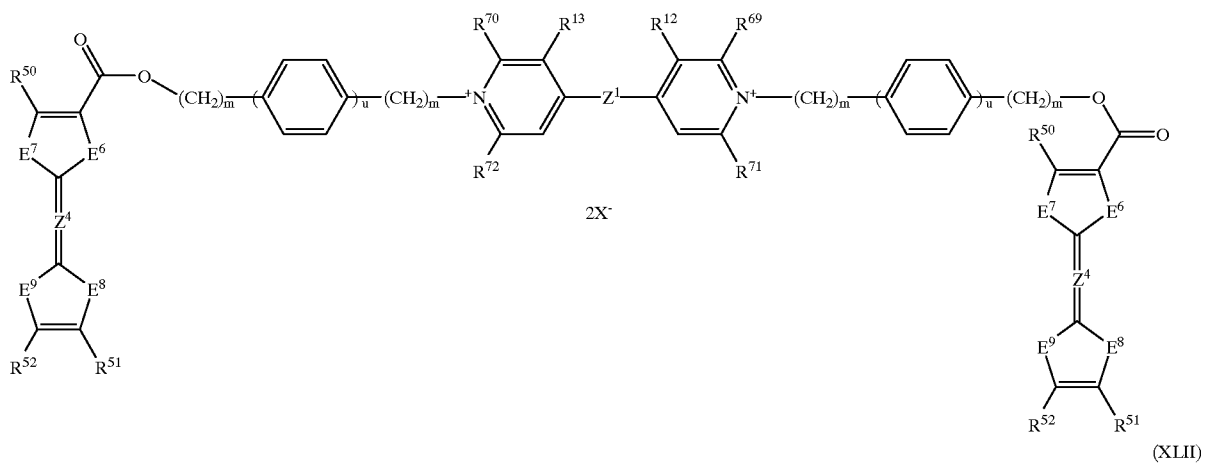

(XLI)

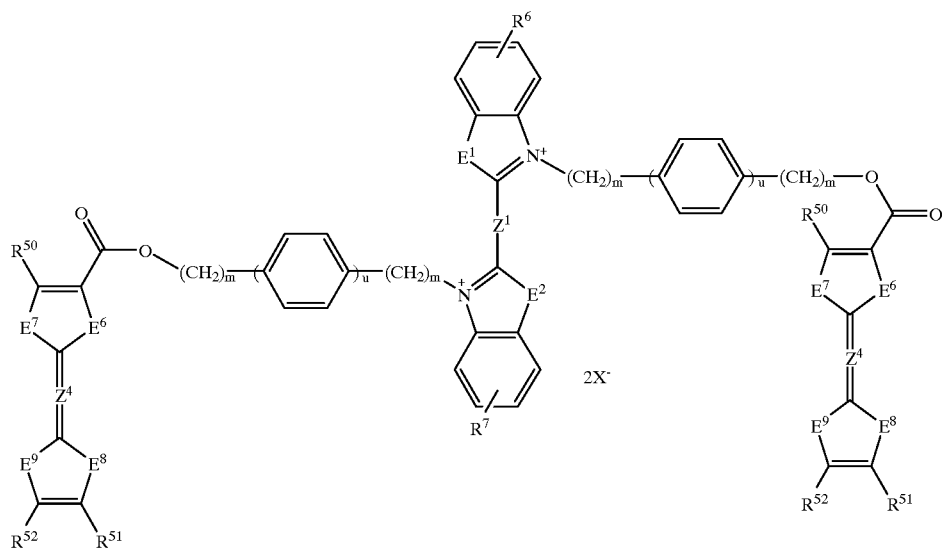

(XLII)

in which

R³, R⁵, R³⁵ and R³⁹ independently of one another represent methyl, ethyl, propyl, butyl, pentyl, hexyl or benzyl, R⁶, R⁷ and R³⁶, R³⁷ in pairs are identical and represent hydrogen, methyl, methoxy, chlorine, cyano or methoxycarbonyl, $R^{12}$ and $R^{13}$ represent hydrogen or, if $Z^1$ denotes a direct bond, together represent a CH=CH bridge, $R^{69}$ to $R^{72}$ are identical and represent hydrogen or methyl, $E^1$ and $R^2$ are identical and represent O or S, $Z^1$ represents a direct bond or —CH=CH—, $R^{32}$, $R^{47}$ and $R^{48}$ represent hydrogen, $E^3$ to $E^5$ independently of one another represent O, S or $NR^{59}$, but where $E^3$ and $E^4$ are identical, $R^{29}$ to $R^{31}$ and $R^{59}$ independently of one another represent methyl, ethyl, propyl, butyl, pentyl, hexyl or benzyl, where $R^{29}$ to $R^{31}$ are preferably identical, $R^{40}$ and $R^{14}$ are identical and represent hydrogen, methyl, ethyl, propyl, butyl or phenyl, $Z^3$ represents a direct bond, —CH=CH— or —N=N—, $R^{50}$ to $R^{52}$ independently of one another represent hydrogen, methyl, methoxy, chlorine, cyano, methoxycarbonyl, ethoxycarbonyl or phenyl, but are preferably identical, $E^6$ to $E^9$ are identical to one another and represent S, Se or $NR^{59}$, $Z^4$ represents a direct double bond or a =CH—CH= or =N—N= bridge, m represents an integer from 1 to 5, u represents 0 or 1 and X⁻ represents a colorless anion which is redox-inert under the conditions, are particularly preferred.

The novel substances of the formula (Ia), $$OX_2—B—RED_1 \qquad (Ia),$$

preferably those substances which correspond to the formulae (XX) to (XXX), can be prepared by reacting compounds of the formula $$OX_2—B—A \qquad (XLIII)$$

with compounds of the formula $$RED_1 \qquad (XLIV),$$

or by reacting compounds of the formula

OX$_2$ (XLV)

with compounds of the formula

A—B—RED$_1$ (XLVI), in which

A denotes a leaving group, such as chlorine, bromine, iodine, OSO$_2$-alkyl, OSO$_2$-perfluoroalkyl or OSO$_2$-aryl and OX$_2$, RED$_1$ and B have the abovementioned general and preferred meaning.

OX$_2$—B—A means, in particular, one of the following compounds:

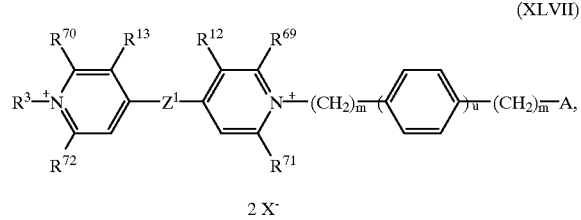
(XLVII)

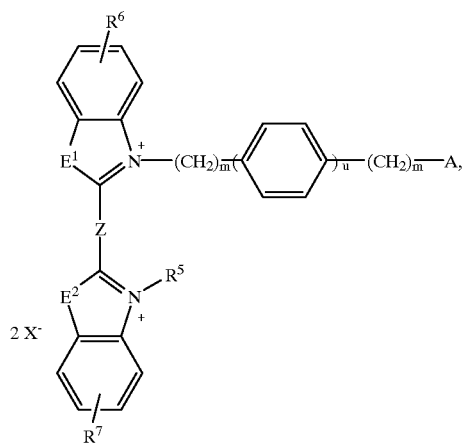
(XLVIII)

in which

A has the abovementioned meaning, in particular represents bromine, and the other radicals have the meaning given above under the definition of the formulae (XXI) and (XXII).

RED$_1$—B—A in particular means one of the following compounds:

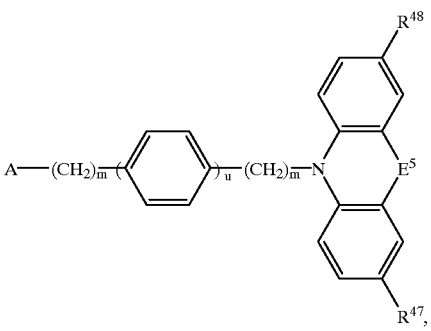
(IL)

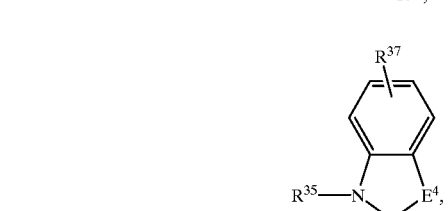
(L)

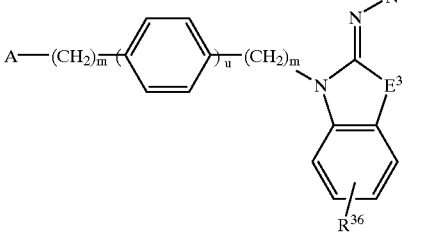
(LI)

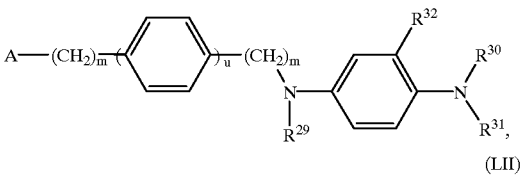
(LII)

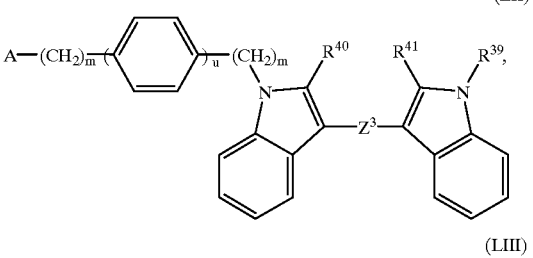
(LIII)

in which

A has the abovementioned meaning, in particular represents bromine, and the other radicals have the meaning given above in the definition of the formulae (XXI), (XXIII), (XXV), (XXVII) and (XXIX).

RED$_1$ then means, in particular, one of the following compounds:

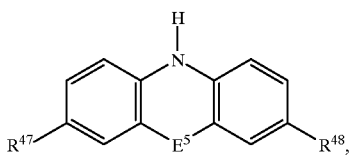
(LIV)

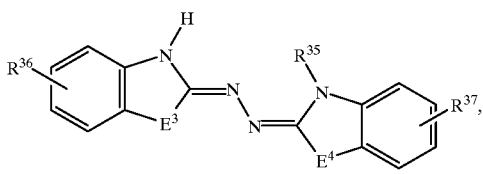
(LV)

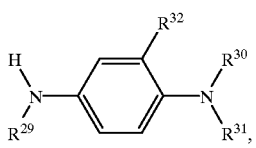
(LVI)

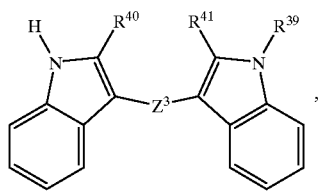
(LVII)

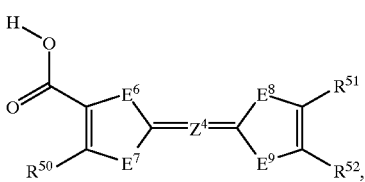
(LVIII)

in which the radicals have the abovementioned meanings. OX₂ then means, in particular, one of the following compounds:

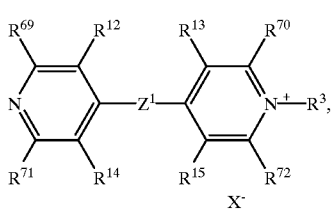
(LIX)

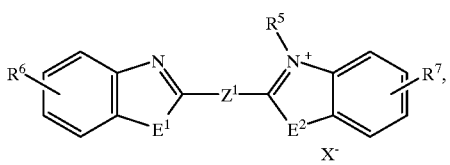
(LX)

in which the radicals have the abovementioned meaning.

The reaction of components (XLIII) and (XLIV) with one another is preferably carried out in polar solvents, such as alcohols—for example methanol, ethanol, propanol or tert-butanol—, nitrites—for example acetonitrile or propionitrile—, amides—for example dimethylformamide or N-methylpyrrolidone—, dimethyl sulfoxide or sulfolane, in the presence of basic compounds, such as hydroxide—for example sodium or potassium hydroxide—, oxides, for example magnesium oxide—, alcoholates—for example sodium methylate or potassium tert-butylate—, amides—for example sodium amide—or basic ion exchangers, at temperatures between 0° C. and the boiling point of the medium, preferably at 5 to 70° C. Depending on the nature of the anion X⁻, the products of the formula (I) are either precipitated directly out of the medium or can be precipitated by addition of, for example, water or alcohols, or the solvent is distilled off in vacuo.

The reaction of components (XLV) and (XLVI) is carried out under the abovementioned conditions, but in the absence of a basic compound.

In both cases, it may be necessary to exchange the anions of the electrochromic substances of the formula (I) thus obtained. This can be effected by means of ion exchangers or by reprecipitation by means of sodium, potassium or tetraalkylammonium salts of the corresponding desired redox-inert anions. Suitable solvents for this operation are the alcohols and nitrites described above and water. Suitable salts are, for example, sodium tetrafluoroborate, sodium perchlorate, sodium hexafluorosilicate, sodium hexafluorophosphate and tetrabutylammonium tetrafluoroborate.

The parent substances $OX_2$ and $RED_1$ are known, for example the substances of the formulae (II) to (IX) from Topics in Current Chemistry, Volume 92, pages 1–44 (1980), Angew. Chem. 90, 927 (1978), Adv. Mater. 3, 225 (1991), DE-OS (German Published Specification) 3,917,323 and, for example, the substances of the formulae (X) to (XIX) from Topics in Current Chemistry, Volume 92, pages 1–44 (1980), Angew. Chem. 90, 927 (1978), J. Am. Chem. Soc. 117, 8528 (1995), J.C.S. Perkin II, 1990, 1777 and DE-OS (German Published Specification) 4,435,211 or from the literature cited therein in each case, or can be prepared analogously.

The components $OX_2$—B—A (XLIII), specifically (XLVII) and (XLVIII) and A—B—$RED_1$ (XLVI), specifically (IL) to (LIII), can be prepared from $OX_2$ and $RED_1$ in a simple manner by reaction with, for example, $$A—B—A \quad (LXI)$$

in one of the abovementioned solvents, in the case of $RED_1$ in the presence and in the case of $OX_2$ in the absence of one of the abovementioned basic compounds under the abovementioned reaction conditions.

The novel substances of the formulae (Ib) to (Id) can be prepared completely analogously.

The substances of the formula (Ib)

$$OX_2—B—RED_1—B—OX_2 \quad (Ib),$$

preferably those substances which correspond to the formulae (XXXI) to (XXXVI), can be prepared by reacting 2 equivalents of compounds of the formula $$OX_2—B—A \quad (XLIII)$$

with one equivalent of compounds of the formula $$RED_1 \quad (XLIV)$$

in which $OX_2$, $RED_1$, A and B have the abovementioned meaning.

$OX_2$—B—A means, in particular, the abovementioned compounds of the formulae (XLVII) and (XLVIII). $RED_1$ means, in particular, the abovementioned compounds of the formulae (LIV), (LV) and (LVIII), in which $E^5$ represents NH, $R^{35}$ represents hydrogen, $R^{51}$ represents —COOH and the other radicals have the abovementioned meaning.

The substances of the formula (Ic)

$$RED_1—B—OX_2—B—RED_1 \quad (Ic)$$

preferably those substances which correspond to the formulae (XXXVII) to (XLII), can be prepared by reacting 2 equivalents of compounds of the formula

$$A—B—RED_1 \quad (XLVI)$$

with one equivalent of compounds of the formula

$$OX_2 \quad (XLV)$$

in which $OX_2$, $RED_1$, A and B have the abovementioned meaning.

A—B—$RED_1$ means, in particular, the abovementioned compounds of the formulae (IL), (L) and (LIII). $OX_2$ means, in particular, one of the following compounds

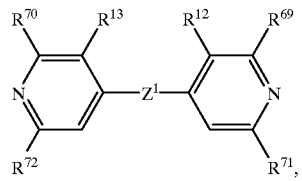

(LXII)

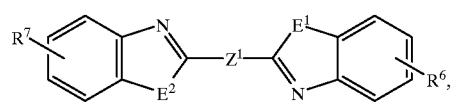

(LXIII)

in which the radicals have the mentioned meaning.

The reaction conditions are then completely analogous to those mentioned above.

In the abovementioned substituent meanings, alkyl radicals, including modified alkyl radicals, such as, for example, alkoxy or aralkyl radicals, are preferably those having 1 to 12 C atoms, in particular 1 to 8 C atoms, unless stated otherwise. They can be straight-chain or branched and can optionally carry further substituents, such as, for example, $C_1$- to $C_4$-alkoxy, fluorine, chlorine, hydroxyl, cyano, $C_1$- to $C_4$-alkoxycarbonyl or COOH.

Cycloalkyl radicals are preferably understood as meaning those having 3 to 7 C atoms, in particular 5 or 6 C atoms.

Alkenyl radicals are preferably those having 2 to 8 C atoms, in particular 2 to 4 C atoms.

Aryl radicals, including those in aralkyl radicals, are preferably phenyl or naphthyl radicals, in particular phenyl radicals. They can be substituted by 1 to 3 of the following radicals: $C_1$- to $C_6$-alkyl, $C_1$- to $C_6$-alkoxy, fluorine, chlorine, bromine, cyano, hydroxyl, $C_1$- to $C_6$-alkoxycarbonyl or nitro. Two adjacent radicals can also form a ring.

The electrochromic system according to the invention preferably comprises at least one solvent, thereby forming an electrochromic liquid, to which the present invention likewise relates.

Suitable solvents are all the solvents which are redox-inert under the voltages chosen and cannot give off electrophiles or nucleophiles or react themselves as sufficiently strong electrophiles or nucleophiles and could thus react with the colored free radical ions. Examples are propylene carbonate, γ-butyrolactone, acetonitrile, propionitrile, glutaronitrile, methylglutaronitrile, 3,3'-oxydipropionitrile, hydroxypropionitrile, dimethylformamide, N-methylpyrrolidone, sulfolane, 3-methylsulfolane or mixtures thereof. Propylene carbonate and mixtures thereof with glutaronitrile or 3-methylsulfolane are preferred.

The electrochromic liquid according to the invention can comprise at least one inert conductive salt.

Suitable inert conductive salts are lithium, sodium and tetraalkylammonium salts, in particular the latter. The alkyl groups can contain between 1 and 18 C atoms and be identical or different. Tetrabutylammonium is preferred. Possible anions to these salts, and also possible anions $X^-$ in the formulae (I), (II), (IV), (VI) and (VII) are all the redox-inert colorless anions. Examples are tetrafluoroborate, perchlorate, methanesulfonate, trifluoromethanesulfonate, perfluorobutanesulfonate, benzenesulfonate, hexafluorophosphate, hexafluoroarsenate and hexafluorosilicate. In the latter case, $X^-$ represents ½ $SiF_6^{2-}$.

The conductive salts are preferably employed in the 0 to 1 molar range.

Thickeners can be employed as further additives to the electrochromic liquid in order to control the viscosity of the liquid. This may be of importance to avoid segregation, i.e. the development of streaky or spotted color formation during relatively long operation of an electrochromic device, in the switched-on state, comprising the electrochromic liquid according to the invention and to control the rate of fading after the current is switched off.

Suitable thickeners are all the compounds customary for this purpose, such as, for example, polyacrylate, polymethacrylate (Luctite L®), polycarbonate and polyurethane.

The electrochromic liquid can also be in the form of a gel.

Possible further additives for the electrochromic liquid are UV absorbers for improving the fastness to light. Examples are Uvinul® 3000 (2,4-hydroxybenzophenone, BASF), SANDUVOR® 3035 (2-hydroxy-4-n-octyloxybenzophenone, Clariant), Tinuvin® 571 (2-(2H-benzotriazol-2-yl)-6-dodecyl-4-methylphenol, Ciba), Cyasorb 24™ (2,2'-dihydroxy-4-methoxybenzophenone, American Cyanamid Company), UVINUL® 3035 (ethyl 2-cyano-3,3-diphenylacrylate, BASF), Uvinul® 3039 (2-ethylhexyl 2-cyano-3,3-diphenylacrylate, BASF) and UVINUL® 3088 (2-ethylhexyl p-methoxycinnamate, BASF).

The UV absorbers are employed in the range from 0.01 to 2 mol/l, preferably 0.04 to 1 mol/l.

The electrochromic liquid according to the invention comprises the substances of the formula (I), in particular of the formulae (Ia) to (Id), in each case in a concentration of at least $10^{-4}$ mol/l, preferably 0.001 to 1 mol/l. Mixtures of several electrochromic substances of the formula (I) can also be employed.

The electrochromic liquids according to the invention are most suitable as a constituent of an electrochromic device. The present invention accordingly relates also to electrochromic devices comprising an electrochromic liquid according to the invention. The build-up of an electrochromic device, which can be constructed, for example, as a window pane, automobile sunroof, automobile rearview mirror or display, is known in principle. The electrochromic device according to the invention comprises two transparent panes of glass or plastic facing one another, one of which is metallized, if appropriate, their sides facing one another being coated with an electrically conductive coating, for example with indium tin oxide (ITO), the electrochromic liquid according to the invention being between these two panes. Suitable conductive materials are also: antimony-doped tin oxide, fluorine-doped tin oxide, antimony-doped zinc oxide, aluminum-doped zinc oxide and tin oxide; and also conductive organic polymers, such as optionally substituted polythienyls, polypyrroles, polyanilines and polyacetylene. In the case where one of the panes is metallized, this can also be used as the conductive layer. The distance between the two panes is in general 0.005–2 mm, preferably 0.02–0.5 mm. The desired distance between the panes is in general produced by a sealing ring.

The self-extinguishing one-cell electrochromic device according to the invention can also comprise, in addition to the electrochromic substances of the formulae (I) described above, in particular the formulae (Ia) to (Id), others such as are described, for example, in U.S. Pat. No. 4,902,108, Topics in Current Chemistry, Volume 92, pages 1–44 (1980) and Angew. Chem. 90, 927 (1978). Such electrochromic substances originate, for example, from the groups mentioned above under the formulae (II) to (XX), where none of the radicals mentioned can then have the meaning of "direct bond to the bridge B". The admixing of such redox systems may be advantageous, for example, in order to correct or intensify the color shade, for example, of the display, in the electrochromic device according to the invention in the switched-on state.

EXAMPLES

Example 1

Preparation of an Electrochromic Substance of the Formula (I)

a) 5.0 g of 4,4'-dipyridyl were dissolved in 30 ml of anhydrous acetonitrile at 50° C. 2.7 g of benzyl bromide were added dropwise at this temperature in the course of 50 minutes. After 3 hours at 50° C., the mixture was cooled and the pale yellow precipitate was filtered off with suction. This was washed with 60 ml of toluene and dried in vacuo. 3.9 g (75% of theory) of the product of the formula

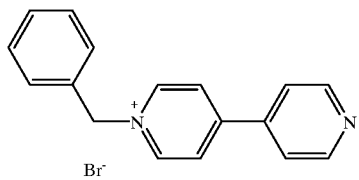

(LXIV)

were obtained.

b) 10.1 g of phenothiazine were dissolved in 60 ml of anhydrous N-methylpyrrolidone at room temperature under an $N_2$ atmoshere. 5.9 g of potassium tert-butylate were added. While heating at 30° C., an orange suspension was formed, which was stirred at 30° C. for 30 minutes. 54 g of 1,4-dibromobutane were then added all at once. During this addition, the temperature rose to 53° C. The mixture was heated to 70° C. in the course of 45 minutes, kept at this temperature for 15 minutes and then cooled. The pale brown suspension was introduced into 1 l of water. The mixture was extracted with 3 times 200 ml of toluene and the extract was washed with 5 times 200 ml of water, dried over sodium sulfate and concentrated on a rotary evaporator. The oily residue was dissolved in 400 ml of hexane, the soluble material was filtered off and the filtrate was concentrated again. The excess 1,4dibromobutane was then distilled off under 0.1 to 0.5 mbar. 9.6 g (57% of theory) of a reddish-yellow, viscous oil of the formula

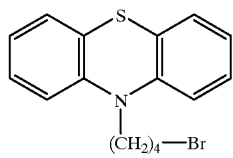

(LXV)

were obtained.

c) 3.7 g of phenothiazine of the formula (LXV) were dissolved in 10 ml of anhydrous N-methylpyrrolidone at room temperature under an $N_2$ atmosphere. 1.8 g of the dipyridinium salt of the formula (LXIV) were added. The suspension was heated to 80° C. in the course of 1 hour and kept at this temperature for a total of 13 hours. During this procedure, the suspension became thicker and thicker. After cooling to room temperature, it was filtered with suction and the residue was washed with 5 ml of N-methylpyrrolidone. The hygroscopic crude product of the formula

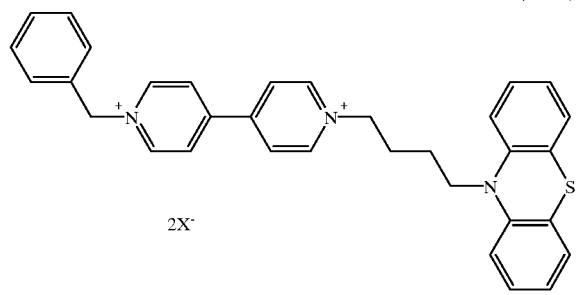

(LXVI)

where $X^-=Br^-$ was dissolved in 7 ml of methanol and the solution was filtered. 3.0 g of tetrabutylammonium tetrafluoroborate were sprinkled into the filtrate in the course of 2 hours. A precipitate slowly formed, precipitation being brought to completion by stirring at room temperature for 18 hours. Finally, the precipitate was filtered off with suction, washed with methanol until the runnings were colorless and dried in vacuo. 0.5 g (13% of theory) of a pale bluish powder of the formula (LXVI) where $X^-=BF_4^-$ was obtained.

In an electrochromic device according to Example 29–30, a violet blue coloration with $\lambda_{max}=517$ and 606 mm was achieved.

Example 2 a) 9.2 g of phenazine were suspended in 60 ml of anhydrous tetrahydrofuran under a nitrogen atmosphere. 30.8 ml of 20% strength by weight phenyllithium solution in cyclohexane/diethyl ether 7:3 were added dropwise in the course of 15 minutes, during which the temperature was kept at not more than 35° C. The solution was subsequently stirred at room temperature for 30 minutes.

30.2 ml of 1,4-dibromobutane were added in one portion at 15° C. During this addition, the temperature rose to 38°

C. After 6 hours at room temperature, 200 ml of water were added and the pH was brought to 7.0. The organic phase was separated off; washed three times with 100 ml of water each time and concentrated in vacuo. Finally, excess 1,4-dibromobutane was distilled off under a pressure of 0.2 mbar. The oily residue was dissolved hot in 400 ml of ethanol. The product which had precipitated out after cooling was filtered off with suction, washed with ethanol and hexane and dried. 8.0 g (41% of theory) of a pale yellow powder of the 9,10-dihydrophenazine of the formula

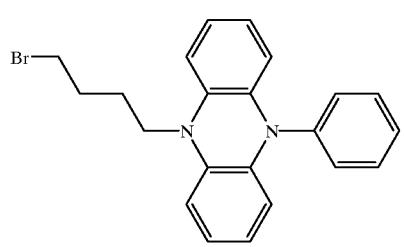

(LXVII)

were obtained.

b) 7.5 g of the 9,10-dihydrophenazine of the formula (LXVII) from a) and 6.1 g of 4,4'-dipyridyl were stirred in 100 ml of acetonitrile at 70° C. under a nitrogen atmosphere for 24 hours. After cooling, the solid was filtered off with suction and washed with 50 ml of acetone. After drying, 6.3 g (60% of theory) of the salt of the formula

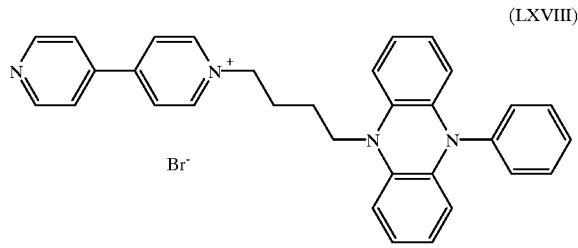

(LXVIII)

were obtained.

c) 6.1 g of the salt obtained under b) were stirred in 70 ml of N-methyl-2-pyrrolidone together with 2.7 ml of benzyl bromide at 70° C. under a nitrogen atmosphere for 7 hours. After cooling, the mixture was diluted with 150 ml of toluene and the product which had precipitated out was filtered off with suction. It was washed thoroughly with 150 ml of toluene and 500 ml of hexane and dried. 5.5 g (69% of theory) of the dipyridinium salt of the formula

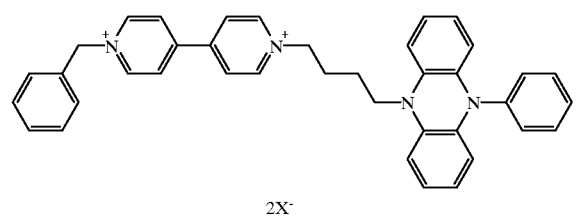

(LXIX)

where X⁻=Br⁻, were obtained.

d) 4.0 g of this product from c) were dissolved in 100 ml of methanol at 65° C. under a nitrogen atmosphere. 7.4 g of tetrabutylammonium tetrafluoroborate were sprinkled in over a period of 5 minutes. Precipitation occurred. After 5 minutes at 65° C., the mixture was cooled and the solid was filtered off with suction, washed with 200 ml of methanol and 50 ml of hexane and was dried in vacuo. 3.4 g (83% of theory) of a pale beige powder of the formula (LXIX) where X⁻=BF₄⁻ were obtained.

In an electrochromic device according to Example 29–30, a greenish-blue coloration with $\lambda_{max}$=466 and 407 nm was achieved.

Example 3 a) 45.3 g of 2-methylthiobenzothiazole were dissolved in 75 ml of toluene. 151 ml of 1,4-dibromobutane and a spatula-tip of potassium iodide were added. The mixture was boiled for 4 hours and then cooled. It was filtered and the residue was washed with 50 ml of toluene. The filtrate was heated to 50° C. and 35.9 ml of dimethyl sulfate were added. The mixture was stirred at 50° C. for 8 hours and cooled and the solid was filtered off with suction and washed with 250 ml of toluene. The product was stirred up in 100 ml of acetone, filtered off with suction again and washed with 300 ml of acetone. After drying in vacuo, 53.1 g (50% of theory) of the salt of the formula

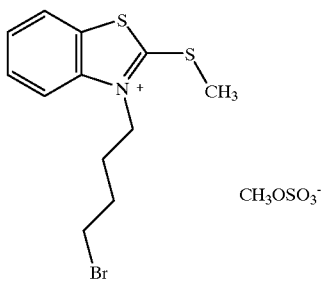

(LXX)

were obtained.

b) 6.95 g of the benzothiazolium salt of the formula (LXX) from a) and 2.9 g of the hydrazone of the formula

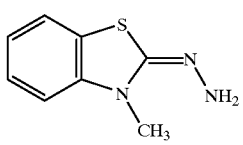

(LXXI)

(from Aldrich Chemical Company Ltd., England) were suspended in 60 ml of acetonitrile under a nitrogen atmosphere. 2.3 ml of triethylamine were added at room temperature. A solution formed in the short term, and a precipitate then formed. After 5 hours at room temperature, the mixture was finally filtered with suction and the residue was washed with 50 ml of methanol, 100 ml of water and a further 50 ml of methanol, until the runnings were colorless, and dried in vacuo. 6.0 g (83% of theory) of the azine of the formula (LXXII)

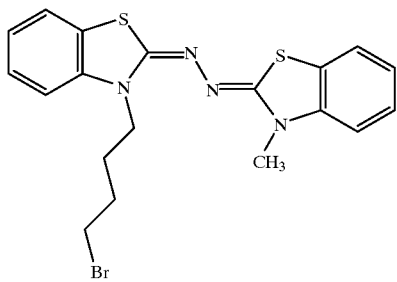

were obtained.

c) If the procedure was analogous to Example 1a), but 6.8 ml of butyl bromide were employed instead of benzyl bromide, 5.2 g (57% of theory) of the pyridinium salt of the formula (LXXIII)

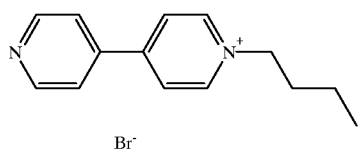

were obtained.

d) 2.0 g of the azine of the formula (LXXII) from b) and 1.3 g of the pyridinium salt of the formula (LXXIII) from c) were stirred in 20 ml of N-methyl-2-pyrrolidone at 80° C. under a nitrogen atmosphere for 102 hours. After cooling, a greenish crystalline product was filtered off with suction and washed with 50 ml of acetone. After drying, 0.25 g (7.6% of theory) of the dipyridinium salt of the formula (LXXIV)

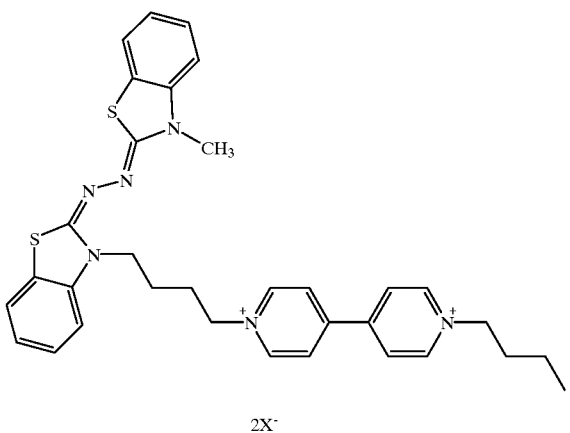

where $X^- = Br^-$, was obtained.

e) 0.25 g of the product from c) was dissolved almost completely in 5 ml of methanol. 0.45 g of tetrabutylammonium tetrafluoroborate was added. The mixture was stirred at room temperature for 17 hours, during which the product gradually became crystalline. It was filtered off with suction and washed with 25 ml of methanol, 25 ml of water and with 25 ml of methanol again. After drying, 0.15 g (59% of theory) of a pale gray powder of the formula (LXXIV) where $X^- = BF_4^-$ was obtained.

In an electrochromic device according to Example 29–30, a green coloration with $\lambda_{max}$=402; 606; and 734 nm was achieved.

Example 4 a) 4.0 g of the phenothiazine of the formula (LXV) from Example 1b) and 0.95 g of 4,4'-dipyridyl were stirred in 10 ml of acetonitrile at 70° C. under a nitrogen atmosphere for 9 hours. The suspension was then diluted with 10 ml of N-methyl-2-pyrrolidone and stirred at 70° C. for 25 hours and at 80° C. for 7 hours. After cooling, the solid was filtered off with suction, washed with 50 ml of methanol and dried in vacuo. 1.6 g (32% of theory) of the dipyridinium salt of the formula (LXXV)

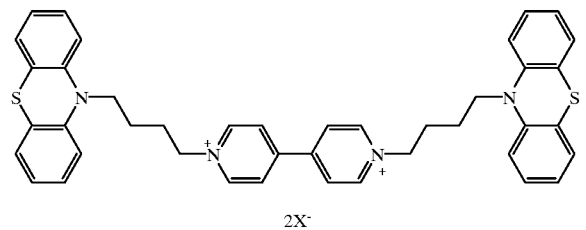

where $X^- = Br^-$, were obtained.

b) 1,4 g of the salt of the formula (LXXV) from a) were partly dissolved in 20 ml of methanol under reflux. 2.3 g of tetrabutylammonium tetrafluoroborate were added. The mixture was boiled for a further 5 minutes and then stirred until cold. The product which had precipitated out was filtered off with suction, washed with 50 ml of methanol, 50 ml of water and with 50 ml of methanol again and dried in vacuo. 1.1 g (77% of theory) of the dipyridinium salt of the formula (LXXV) where $X^- = BF_4^-$ were obtained.

In an electrochromic device according to Example 29–30, a violet blue coloration with $\lambda_{max}$=517 and 606 nm was achieved.

The following Examples were prepared completely analogously.

| Example | OX$_2$-B-RED$_1$ | Color |
|---|---|---|
| 6 | | violet blue |
| 7 | | greenish blue |
| 8 | | green |
| 9 | | green |
| 10 | | blue |

-continued

| Example | OX₂-B-RED₁ | Color |
|---|---|---|
| 11 | | violet |
| 12 | | blue |
| 13 | | reddish-tinged blue |
| 14 | | green |
| 15 | | violet |

-continued
| Example | OX₂-B-RED₁ | Color |
|---|---|---|
| 16 | 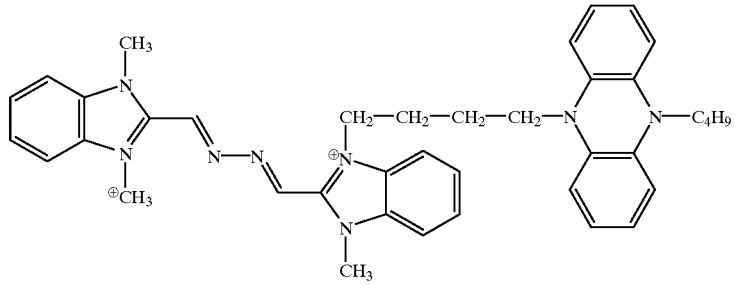 | green |
| 17 | 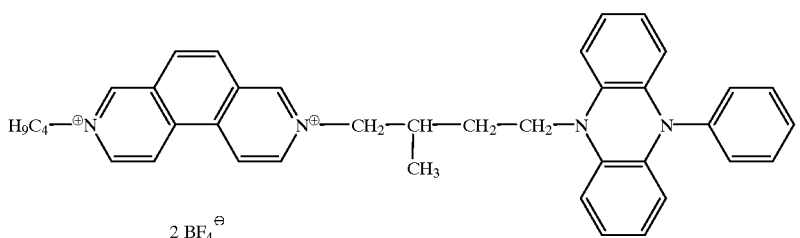 | green |
| 18 | 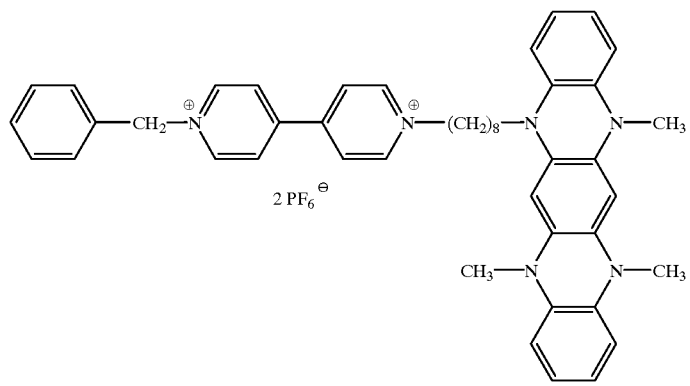 | blue |
| 19 | 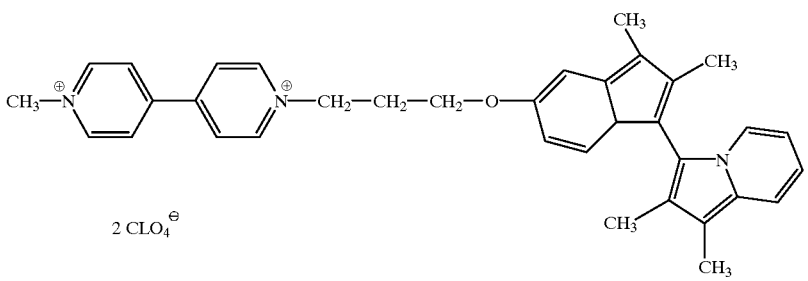 | reddish-tinged blue |
| 20 | 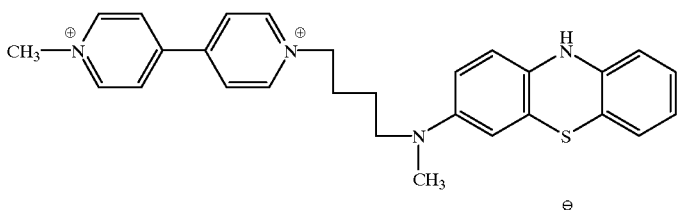 | violet |

| Example | RED₁-B-OX₂-B-RED₁ | Color |
|---------|-------------------|-------|
| 21 | | greenish-tinged blue |
| 22 | | blue |
| 23 | | green |

-continued

| Example | RED$_1$-B-OX$_2$-B-RED$_1$ | Color |
|---------|---------------------------|-------|
| 24 | | greenish blue |
| 25 | | violet |

-continued
| Example | RED₁-B-OX₂-B-RED₁ | Color |
|---|---|---|
| 26 | 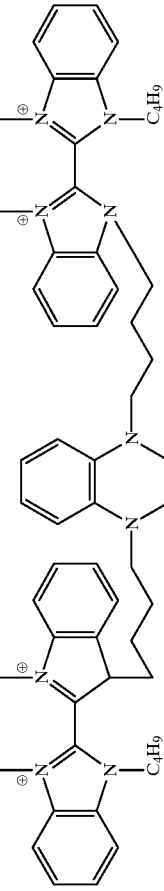 | green |
| 27 | 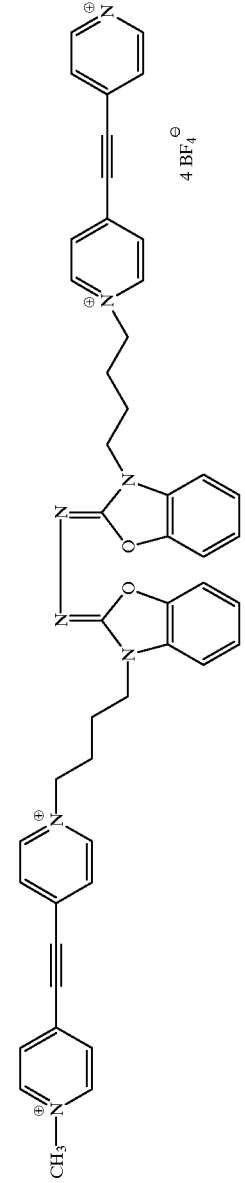 | greenish blue |
| 28 | 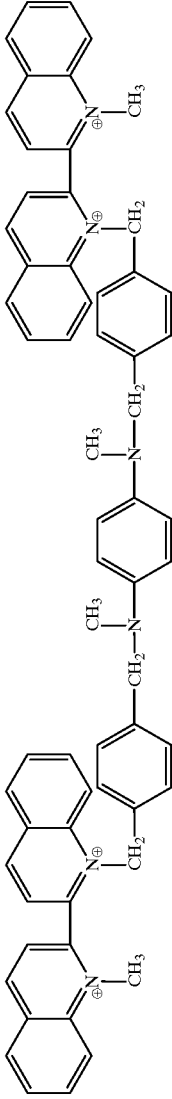 | blue-green |

Example 29

A cell was constructed from two glass plates coated with indium tin oxide (ITO) and a sealing ring, such as is described in U.S. Pat. No. 4,902,108. It was filled under a nitrogen atmosphere, via an opening in the sealing ring, with a solution which was 0.03 molar with respect to the electrochromic substance of the formula (LXXIV) where $X^{63}=BF_4^{63}$) according to Example 3 in anhydrous glutaric acid dinitrile. The cell was closed airtight. The solution in the cell was pale yellow. When a voltage of 1.5 V was applied, the solution rapidly became intense green in color, and when the voltage was switched off, the contents of the cell decolorized again completely in the course of 1 minute. The decoloration took place more rapidly by short-circuiting the cell.

After 9000 coloring/decoloring cycles, the cell still operated without problems.

Example 30

A cell was constructed as in Example 4. However, one of the glass plates was metallized on the side facing away from the ITO layer.

It was filled under an $N_2$ atmosphere with a solution which was 0.03 molar with respect to the electrochromic substance of the formula (LXIX) where $X^\ominus=BF_4^\ominus$ according to Example 2 in anhydrous propylene carbonate. The color of the solution in the cell was pale yellow. When a voltage of 0.9 V was applied, the solution rapidly became deep greenish-blue in color, and when the current supply was switched off and the cell was short-circuited, the content of the cell decolorized again within about 10 seconds and resulted in the original pale yellow. It survived more than 30,000 such switching cycles without any changes.

Electrochromic cells were built up completely analogously to Examples 29–30 using the electrochromic substances mentioned in Examples 1–28, similarly good results being achieved.

What is claimed is:

1. An electrochromic system comprising at least one oxidizable substance $RED_1$ and at least one reducible substance $OX_2$ which, by electron donation of the former at an anode and by electron acceptance of the latter at a cathode, in each case with an increase in the extinction in the visible range of the spectrum, are converted from a slightly colored or colorless form into a colored form $OX_1$ and $RED_2$ respectively, in each case the slightly colored or colorless form being reformed after charge compensation, wherein at least one of the substances $RED_1$ and $OX_2$ contained therein are linked together covalently via a bridge.

2. An electrochromic system as claimed in claim 1, which comprises at least one electrochromic substance of the formula (I)

$$Y\text{---}(B\text{---}Z)_a\text{---}(B\text{---}Y)_b]_c B\text{---}Z, \quad (I)$$

in which

Y and Z independently of one another represent a radical $OX_2$ or $RED_1$, but in which at least one Y represents $OX_2$ and at least one Z represents $RED_1$, in which $OX_2$ represents the radical of a reversibly electrochemically reducible redox system and $RED_1$ represents the radical of a reversibly electrochemically oxidizable redox system, B represents a bridge member, c represents an integer from 0 to 5 and a and b independently of one another represent an integer from 0 to 5.

3. An electrochromic system as claimed in claim 2, which comprises at least one electrochromic substance of the formula (I) in which Y represents $OX_2$ and Z represents $RED_1$ and Y and Z alternate in their sequence.

4. An electrochromic system as claimed in claim 1, which comprises at least one electrochromic substance of the formulae $$OX_2\text{---}B\text{---}RED_1, \quad (Ia)$$

$$OX_2\text{---}B\text{---}RED_1\text{---}B\text{---}OX_2, \quad (Ib)$$

$$RED_1\text{---}B\text{---}OX_2\text{---}B\text{---}RED_1, \text{ or} \quad (Ic)$$

$$OX_X\text{---}(B\text{---}RED_1\text{---}B\text{---}OX_2)_d\text{---}B\text{---}RED_1, \quad (Id)$$

in which

B represents a bridge member, and d represents an integer from 1 to 5.

5. An electrochromic system as claimed in claim 4, which comprises at least one electrochromic substance of the formulae (Ia)–(Id), in which $OX_2$ represents the radical of a cathodically reducible substance which, in the cyclic voltammogram recorded in an inert solvent at room temperature, shows at least two chemically reversible reduction waves, the first of these reduction waves leading to an increase in the extinction at not less than one wavelength in the visible range of the electromagnetic spectrum, $RED_1$ represents the radical of the anodically reversibly oxidizable substance which, in the cyclic voltammogram recorded in an inert solvent at room temperature, shows at least two chemically reversible oxidation waves, the first of these oxidation waves leading to an increase in the extinction at not less than one wavelength in the visible range of the electromagnetic spectrum and B represents a bridge member.

6. An electrochromic system as claimed in claim 4, which comprises at least one substance of the formula (Ia)–(Id), in which $OX_2$ represents a radical of the formulae (II)

$$R^2\text{---}\overset{+}{N}\underset{R^{71}}{\overset{R^{69}}{\diagdown}}\underset{R^{14}}{\overset{R^{12}}{\diagup}}\text{---}Z^1\text{---}\underset{R^{15}}{\overset{R^{13}}{\diagdown}}\underset{R^{72}}{\overset{R^{70}}{\diagup}}\overset{+}{N}\text{---}R^3,$$

$$2X^-$$

-continued (III)
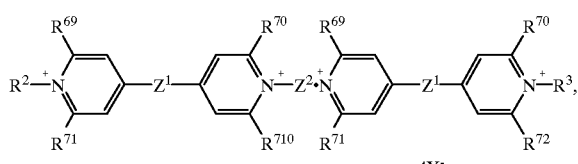
4X⁻

(IV)
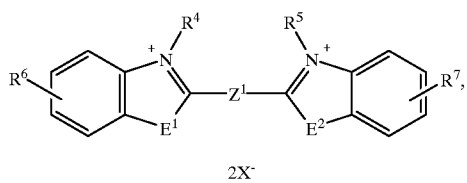
2X⁻

(V)
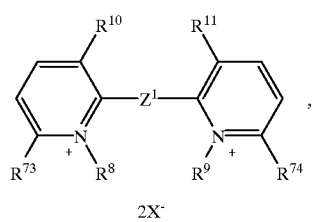
2X⁻

(VI)
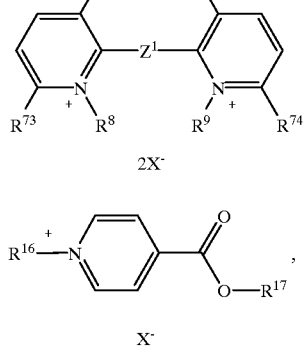
X⁻

(VII)
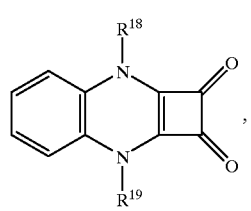

(VIII)
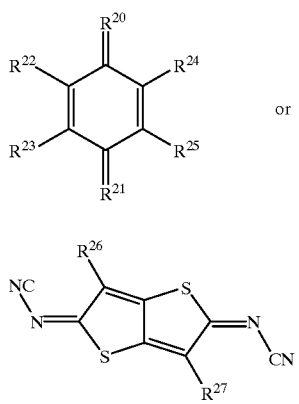
or (IX)
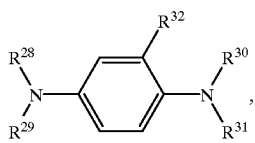

in which $R^2$ to $R^5$, $R^8$, $R^9$ and $R^{16}$ to $R^{19}$ independently of one another denote $C_1$- to $C_{18}$-alkyl, $C_2$- to $C_{12}$-alkenyl, $C_3$- to $C_7$-cycloalkyl, $C_7$- to $C_{15}$-aralkyl or $C_6$- to $C_{10}$-aryl or $R^4$ and $R^5$ or $R^8$ and $R^9$ together form a —(CH$_2$)$_2$— or —(CH$_3$)— bridge, $R^6$, $R^7$ and $R^{22}$ to $R^{25}$ independently of one another denote hydrogen, $C_1$- to $C_4$-alkyl, $C_1$- to $C_4$-alkoxy, halogen, cyano, nitro or $C_1$- to $C_4$-alkoxycarbonyl or $R^{22}$ and $R^{23}$ and/or $R^{24}$ and $R^{25}$ form a —CH=CH—CH=CH— bridge, $R^{10}$ and $R^{11}$; $R^{12}$ and $R^{13}$; and $R^{14}$ and $R^{15}$ independently of one another denote hydrogen or, in pairs, a —(CH$_2$)$_2$—, —(CH$_2$)$_3$— or —CH=CH— bridge, $R^{69}$ to $R^{74}$ independently of one another denote hydrogen or $C_1$–$C_6$-alkyl, or $R^{69}$; $R^{12}$ and/or $R^{70}$; and $R^{13}$ form a —CH=CH—CH=CH— bridge, $R^{20}$ and $R^{21}$ independently of one another denote O, N—CN, C(CN)$_2$ or N—$C_6$- to $C_{10}$-aryl, $R^{26}$ denotes hydrogen, $C_1$- to $C_4$-alkyl, $C_1$- to $C_4$-alkoxy, halogen, cyano, nitro, $C_1$- to $C_4$-alkoxycarbonyl or $C_6$- to $C_{10}$-aryl, $E^1$ and $E^2$ independently of one another denote O, S, NR$^1$ or C(CH$_3$)$_2$ or $E^1$ and $E^2$ together form a —N—(CH$_2$)$_2$—N— bridge, $R^1$ denotes $C_1$- to $C_{18}$-alkyl, $C_2$- to $C_{12}$-alkenyl, $C_4$- to $C_7$-cycloalkyl, $C_7$- to $C_{15}$-aralkyl or $C_6$- to $C_{10}$-aryl, $Z^1$ denotes a direct bond —CH=CH—, —C(CH$_3$)=CH—, —C(CN)=CH—, —CCl=CCl—, —C(OH)=CH—, —CCl=CH—, —C≡C—, —CH=N—N=CH—, —C(CH$_3$)=N—N=C(CH$_3$)— or —CCl=N—N=CCl—, $Z^2$ denotes —(CH$_2$)$_r$— or —CH$_2$—C$_6$H$_4$—CH$_2$—, r denotes an integer from 1 to 10, X⁻ denotes an anion which is redox-inert under the conditions, wherein bonding to the bridge member B is effected via one of the radicals $R^2$–$R^{19}$, $R^2$–$R^{27}$ or, in the case where $E^1$ or $E^2$ represents NR$^1$, via R$^1$ and the radicals mentioned then represent a direct bond, RED$_1$ represents one of the following radicals (X)
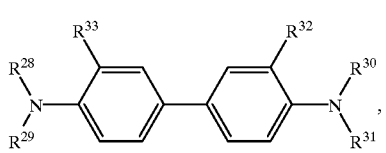

(XI)
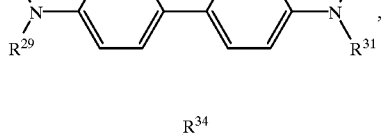

(XII)
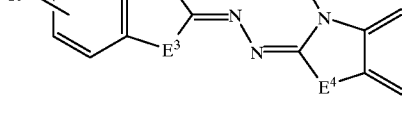

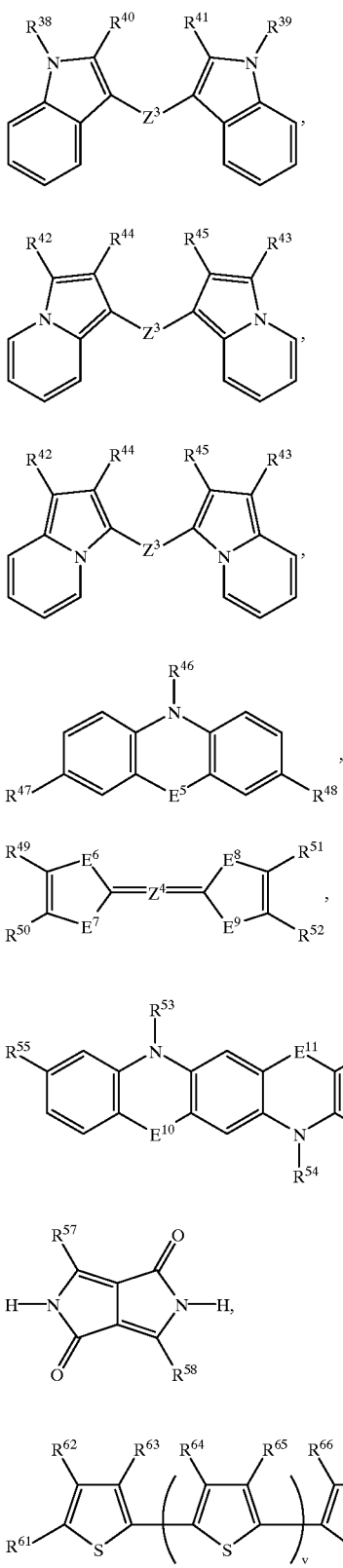

wherein
R$^{28}$ to R$^{31}$, R$^{34}$, R$^{35}$, R$^{38}$, R$^{39}$, R$^{46}$, R$^{53}$ and R$^{54}$ independently of one another denote C$_1$- to C$_{18}$-alkyl, C$_2$- to C$_{12}$-alkenyl, C$_3$- to C$_7$-cycloalkyl, C$_7$- to C$_{15}$-aralkyl or C$_6$- to C$_{10}$-aryl, and R$^{46}$, R$^{53}$ and R$^{54}$ additionally denote hydrogen, R$^{32}$, R$^{33}$, R$^{36}$, R$^{37}$, R$^{40}$, R$^{41}$, R$^{42}$ to R$^{45}$, R$^{47}$, R$^{48}$, R$^{49}$ to R$^{52}$ and R$^{55}$ to R$^{57}$ independently of one another denote hydrogen, C$_1$- to C$_4$-alkyl, C$_1$- to C$_4$-alkoxy, halogen, cyano, nitro, C$_1$- to C$_4$-alkoxycarbonyl or C$_6$- to C$_{10}$-aryl and R$^{57}$ and R$^{58}$ additionally denote an optionally benzo-fused aromatic or quasiaromatic five- or six-membered heterocyclic ring and R$^{48}$ additionally denotes NR$^{75}$R$^{76}$, R$^{49}$ and R$^{50}$ and/or R$^{51}$ and R$^{52}$ form a —(CH$_2$)$_3$—, —(CH$_2$)$_4$—, —(CH$_2$)$_5$— or —CH=CH—CH=CH— bridge, Z$^3$ denotes a direct bond or a —CH=CH— or —N=N— bridge, =Z$^4$= denotes a direct double bond or a =CH—CH= or =N—N= bridge E$^3$ to E$^5$, E$^{10}$ and E$^{11}$ independently of one another denote O, S, NR$^{59}$ or C(CH$_3$)$_2$ and E$^5$ additionally denotes C=O or SO$_2$, or E$^3$ and E$^4$ independently of one another denote —CH=CH—, E$^6$ to E$^9$ independently of one another denote S, Se or NR$^{59}$, R$^{59}$, R$^{75}$ and R$^{76}$ independently of one another denote C$_1$- to C$_{12}$-alkyl, C$_2$- to C$_8$-alkenyl, C$_3$ to C$_7$-cycloalkyl, C$_7$- to C$_{15}$-aralkyl or C$_6$- to C$_{10}$-aryl and R$^{73}$ additionally denotes hydrogen, or R$^{73}$ and R$^{75}$ in the meaning of NR$^{73}$R$^{74}$, together with the N atom to which they are bonded, form a five- or six-membered saturated ring which can contain further heteroatoms, R$^{61}$ to R$^{68}$ independently of one another denote hydrogen, C$_1$- to C$_6$-alkyl, C$_1$- to C$_4$-alkoxy, cyano, C$_1$- to C$_4$-alkoxycarbonyl or C$_6$- to C$_{10}$-aryl, or R$^{61}$; R$^{62}$ and R$^{67}$; and R$^{68}$ independently of one another together form a —(CH$_2$)$_3$—, —(CH$_2$)$_4$— or —CH=CH—CH=CH— bridge, v denotes an integer between 0 and 10, wherein bonding to the bridge member B is effected by one of the radicals R$^2$–R$^{58}$, R$^{61}$, R$^{62}$, R$^{67}$, R$^{68}$ or, in the case where one of the radicals E$^3$–E$^{11}$ represents NR$^{59}$, via R$^{59}$ and the radicals mentioned then represent a direct bond, and B represents a bridge member of the formula —(CH$_2$)$_n$— or —[Y$^1{}_s$(CH$_2$)$_m$—Y$^2$]$_o$—(CH$_2$)$_p$—Y$^3{}_q$—, each of which is optionally substituted by C$_1$- to C$_4$-alkoxy, halogen or phenyl, Y$^1$ to Y$^3$ independently of one another represent O, S, NR$^{60}$, COO, CONH, NHCONH, cyclopentanediyl, cyclohexanediyl, phenylene or naphthylene, R$^{60}$ denotes C$_1$- to C$_6$-alkyl, C$_2$- to C$_6$-alkenyl, C$_4$- to C$_7$-cycloalkyl, C$_7$- to C$_{15}$-aralkyl or C$_6$- to C$_{10}$-aryl, n denotes an integer from 1 to 12, m and p independently of one another denote an integer from 0 to 8, o denotes an integer from 0 to 6 and q and s independently of one another denote 0 or 1.

7. An electrochromic system as claimed in claim 6, which comprises at least one substance of the formula (Ia)–(Id) in which O X$_2$ represents a radical of the formulae (II), (III), (IV) or (V), in which $R^2$, $R^3$, $R^4$, $R^5$, $R^8$ and $R^9$ independently of one another represent $C_1$- to $C_{12}$-alkyl, $C_2$- to $C_8$-alkenyl, $C_5$- to $C_7$-cycloalllyl, $C_7$- to $C_{15}$-aralkyl or $C_6$- to $C_{10}$-aryl, $R^6$ and $R^7$ independently of one another represent hydrogen, methyl, ethyl, methoxy, ethoxy, fluorine, chlorine, bromine, cyano, nitro, methoxycarbonyl or ethoxycarbonyl, $R^{10}$, $R^{11}$; $R^{12}$, $R^{13}$ and $R^{14}$, $R^{15}$ independently of one another represent hydrogen or, if $Z^1$ denotes a direct bond, in each case together in pairs represent a —$(CH_2)_2$—, —$(CH_2)_3$— or —CH=CH— bridge, or $R^4$, $R^5$ and $R^8$, $R^9$ independently of one another in pairs together represent a —$(CH_2)_2$— or —$(CH_3)_3$— bridge, if $Z^1$ denotes a direct bond, $R^{69}$ to $R^{74}$ independently of one another denote hydrogen or $C_1$–$C_4$-alkyl, $E^1$ and $E^2$ are identical and represent O, S, $NR^1$ or $C(CH_3)_2$ or together form a —N—$(CH_2)_2$—N— bridge, $R^1$ represents $C_1$- to $C_{12}$-alkyl, $C_2$- to $C_4$-alkenyl, $C_5$- to $C_7$-cycloalkyl, $C_7$- to $C_{15}$-aralkyl or $C_6$- to $C_{10}$-aryl, $Z^1$ represents a direct bond, —CH=CH—, —C(CH_3)=CH—, —C(CN)=CH—, —C≡C— or —CH=N—N=CH—, $Z^2$ represents —(CH)_r— or —$CH_2$—$C_6H_4$—$CH_2$—, r represents an integer between 1 and 6, $X^-$ represents a colorless anion which is redox-inert under the conditions, wherein bonding to the bridge member B is effected by one of the radicals $R^2$–$R^{11}$ or, in the case where $E^1$ or $E^2$ represents $NR^1$, via $R^1$ and the radicals mentioned then represent a direct bond, $RED_1$ represents a radical of the formulae (X), (XI), (XII), (XIII), (XVI), (XVII), (XVIII) or (XX), in which $R^{28}$ to $R^{31}$, $R^{34}$, $R^{35}$, $R^{38}$, $R^{39}$, $R^{46}$, $R^{53}$ and $R^{54}$ independently of one another denote $C_1$- to $C_{12}$-alkyl, $C_2$- to $C_8$-alkenyl, $C_5$- to $C_7$-cycloalkyl, $C_7$- to $C_{15}$-aralkyl or $C_6$- to $C_{10}$-aryl and $R^{46}$, $R^{53}$ and $R^{54}$ additionally denote hydrogen, $R^{32}$, $R^{33}$, $R^{36}$, $R^{37}$, $R^{40}$, $R^{41}$, $R^{47}$ to $R^{52}$, $R^{55}$ and $R^{56}$ independently of one another denote hydrogen, methyl, ethyl, methoxy, ethoxy, fluorine, chlorine, bromine, cyano, nitro, methoxycarbonyl, ethoxycarbonyl or phenyl and $R^{57}$ and $R^{58}$ additionally denote 2- or 4-pyridyl and $R^{48}$ additionally denotes $NR^{75}R^{76}$, $Z^3$ denotes a direct bond or a —CH=CH— or 13 N=N— bridge, =$Z^4$= denotes a direct bond or a =CH—CH= or =N—N= bridge, $E^3$ to $E^5$, $E^{10}$ and $E^{11}$ independently of one another denote O, S, $NR^{59}$ or $C(CH_3)_2$, but $E^3$ and $E^4$ have the same meaning, $E^6$ to $E^9$ are identical to one another and denote S, Se or $NR^{59}$ and $E^5$ additionally denotes C=O, $E^6$ represents $NR^{59}$, in which $R^{59}$ denotes a direct bond to the bridge B and $E^7$ to $E^9$ have the abovementioned meaning but must not be identical to one another, $R^{59}$, $R^{75}$ and $R^{76}$ independently of one another denote $C_1$- to $C_{12}$-alkyl, $C_2$- to $C_8$-alkenyl, $C_5$- to $C_7$-cycloalkyl, $C_7$- to $C_{15}$-aralkyl or $C_6$- to $C_{10}$-aryl, and $R^{73}$ additionally denotes hydrogen or $R^{73}$ and $R^{74}$ in the meaning $NR^{73}R^{74}$, together with the N atom to which they are bonded, denote pyrrolidino, piperidino or morpholino, $R^{61}$, $R^{62}$ and $R^{67}$, $R^{68}$ independently of one another represent hydrogen, $C_1$- to $C_4$-alkyl, methoxycarbonyl, ethoxycarbonyl or phenyl or in pairs together represent a —$(CH_2)_3$— or —$(CH_2)_4$— bridge, $R^{63}$ to $R^{66}$ represents hydrogen and v represents an integer from 1 to 6, wherein bonding to the bridge member B is effected by one of the radicals $R^{28}$–$R^{41}$, $R^{46}$–$R^{56}$, $R^{61}$, $R^{62}$, $R^{67}$, $R^{68}$ or, in the case where one of the radicals $E^3$–$E^{11}$ represents $NR^{59}$, via $R^{59}$ and the radicals mentioned then represent a direct bond, B represents a bridge member of the formulae —$(CH_2)_n$—, —$(CH_2)_m$—O—$(CH_2)_p$—, —$(CH)_m$—$NR^{60}$—$(CH_2)_p$—, —$(CH_2)_m$—$C_6H_4$—$(CH_2)_p$—, —[O—$(CH_2)_p]_o$—O—, —[$NR^{60}$—$(CH_2)_p]_o$—$NR^{60}$—, —[$C_6H_4$—$(CH_2)_p]_o$—$C_6H_4$—, —$(CH_2)_m$—OCO—$C_6H_4$—COO—$(CH_2)_p$—, —$(CH_2)_m$—NHCO—$C_6H_4$—CONH—$(CH_2)_p$—, —$(CH_2)_m$—NHCONH—$C_6H_4$—NHCONH—$(CH_2)_p$—, —$(CH_2)_m$—OCO—$(CH_2)_t$—COO—$(CH_2)_p$—, —$(CH_2)_m$NHCO—$(CH_2)_t$—CONH—$(CH)_p$—, —$(CH_2)_m$—NHCONH—$(CH_2)_t$—NHCONH—$(CH_2)_p$—, $R^{60}$ represents methyl, ethyl, benzyl or phenyl, n represents an integer from 1 to 10, m and p independently of one another represent an integer from 0 to 4, represents an integer from 0 to 2 and t represents an integer from 1 to 6.

8. An electrochromic system as claimed in claim 6, which comprises at least one substance of the formula (Ia)–(Id)

in which $OX_2$ represents a radical of the formulae (II), (IV) or (V), in which $R^2$, $R^4$ and $R^8$ represent a direct bond to the bridge member B, $R^3$, $R^5$ and $R^9$ independently of one another represent methyl, ethyl, propyl, butyl, pentyl, hexyl, heptyl, octyl, benzyl or phenyl, or in the case of the formulae Ic or Id, also represent a direct bond to the bridge member B, $R^6$ and $R^7$ are identical or different and represent hydrogen, methyl, methoxy, chlorine, cyano or methoxycarbonyl, $R^{10}$, $R^{11}$; $R^{12}$, $R^{13}$ and $R^{14}$, $R^{15}$ independently of one another represent hydrogen or, if $Z^1$ denotes a direct bond, in each case in pairs together represent a —CH=CH— bridge, $R^{69}$ to $R^{72}$ are identical and denote hydrogen, methyl or ethyl, $R^{73}$ and $R^{74}$ denote hydrogen, $E^1$ and $E^2$ are identical and represent O or S, $Z^1$ represents a direct bond or —CH=CH—, $X^-$ represents a colorless anion which is redox-inert under the conditions, $RED_1$ represents a radical of the formulae (X), (XII), (XIII), (XVI) or (XVII), R$^{28}$, R$^{34}$, R$^{38}$, R$^{46}$ and R$^{49}$ represent a direct bond to the bridge member B, R$^{29}$ to R$^{31}$, R$^{35}$ and R$^{39}$ independently of one another represent methyl, ethyl, propyl, butyl, pentyl, hexyl, heptyl, octyl, benzyl or phenyl, or R$^{30}$, R$^{35}$ and R$^{39}$ in the case of the formulae Ib and Ic also represent a direct bond to the bridge member B, R$^{32}$, R$^{47}$ and R$^{48}$ represent hydrogen, R$^{36}$, R$^{37}$, R$^{40}$, R$^{41}$ and R$^{50}$ to R$^{52}$ independently of one another represent hydrogen, methyl, methoxy, chlorine, cyano, methoxycarbonyl or phenyl, or, R$^{51}$ in the case of the formulae Ib and Id also represent a direct bond to the bridge member B, Z$^3$ represents a direct bond or a —CH=CH— or —N=N— bridge, =Z$^4$= represents a direct double bond or a =CH—CH= or =N—N= bridge, E$^3$ to E$^5$ independently of one another represent O, S or NR$^{59}$, but E$^3$ and E$^4$ have the same meaning, E$^6$ to E$^9$ are identical to one another and represent S, Se or NR$^{59}$, R$^{59}$ represents methyl, ethyl, propyl, butyl, pentyl, hexyl, heptyl, octyl, benzyl or phenyl, or R$^{59}$ in the case of the formula XVI in formula Ib or Id also represents a direct bond to the bridge member B, B represents a bridge member of the formulae —(CH$_2$)$_n$—, —(CH$_2$)$_m$—O—(CH$_2$)$_p$—, —(CH$_2$)$_m$—NR$^{60}$—(CH$_2$)$_p$—, —(CH$_2$)$_m$—C$_6$H$_4$—(CH$_2$)$_p$—, —[O—(CH$_2$)$_p$]—O—, —NR$^{60}$—(CH$_2$)$_p$—NR$^{60}$—, —(CH$_2$)$_m$—OCO—C$_6$H$_4$—COO—(CH$_2$)$_p$—, —(CH$_2$)$_m$—NHCO—C$_6$H$_4$—CONH—(CH$_2$)$_p$—, —(CH$_2$)$_m$—NHCONH—C$_6$H$_4$—NHCONH—(CH$_2$)$_p$—, —(CH$_2$)$_m$—OCO—(CH$_2$)$_t$—COO—(CH$_2$)$_p$—, —(CH$_2$)$_m$—NHCO—(CH$_2$)$_t$—CONH—(CH$_2$)$_p$—, —(CH$_2$)$_m$—NHCONH—(CH$_2$)$_t$—NHCONH—(CH$_2$)$_p$—, R$^{60}$ represents methyl, n represents an integer from 1 to 10, m and p are identical and represent an integer from 0 to 2 and t represents an integer from 1 to 6.

9. An electrochromic system as claimed in claim 1, which comprises at least one electrochromic substance of the formula (Ia)

$$OX_2—B—RED_1 \tag{Ia}$$

corresponding to one of the formulae (XXI)

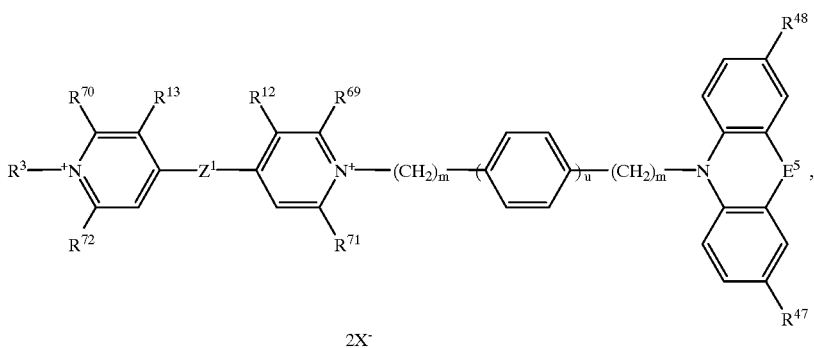

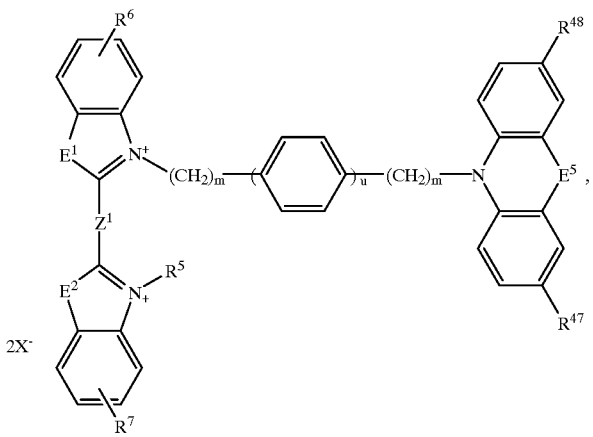

(XXII)

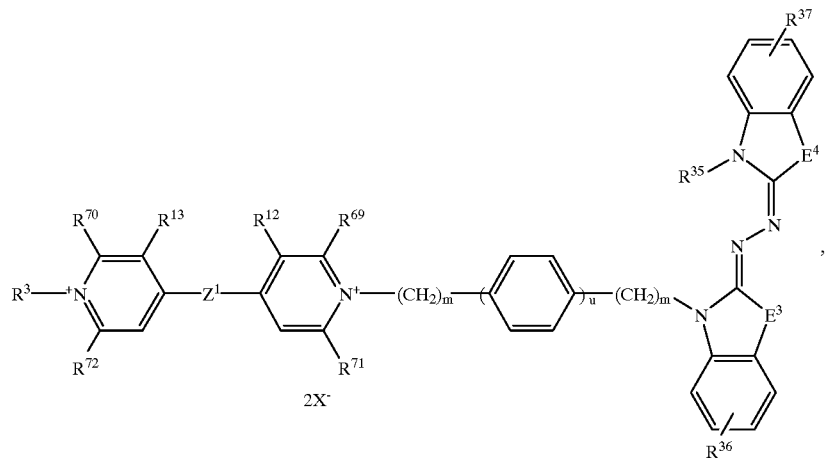
(XXIII)
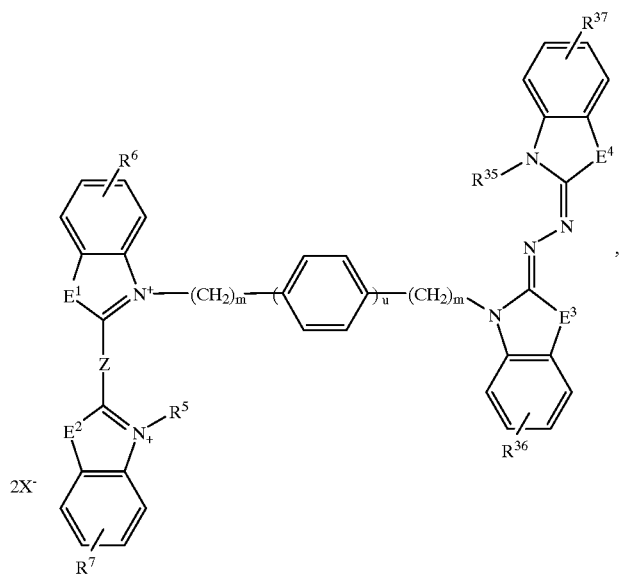
(XXIV)
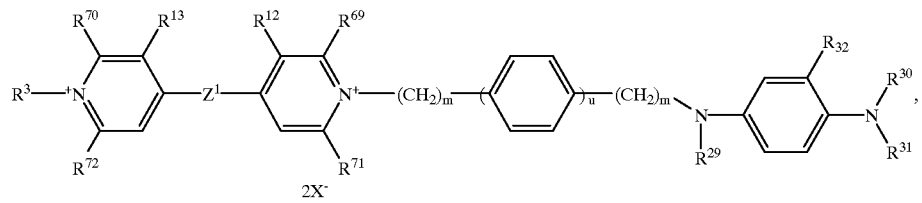
(XXV)

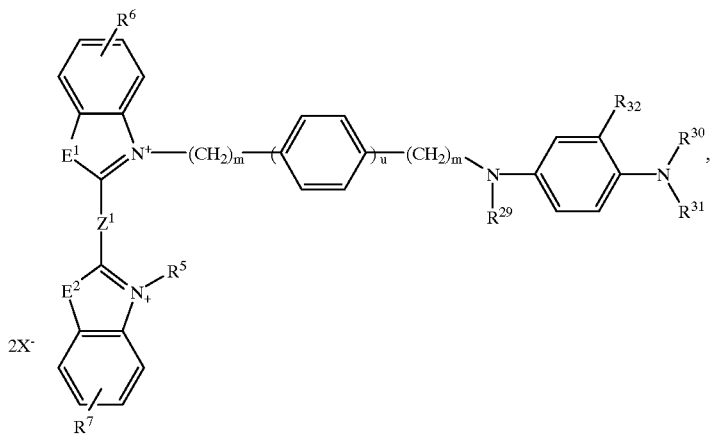
(XXVI)
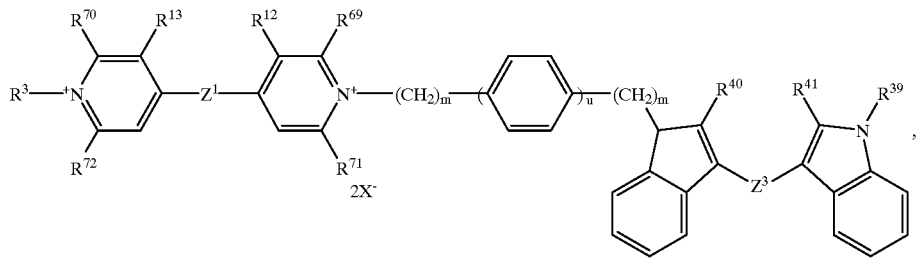
(XXVII)
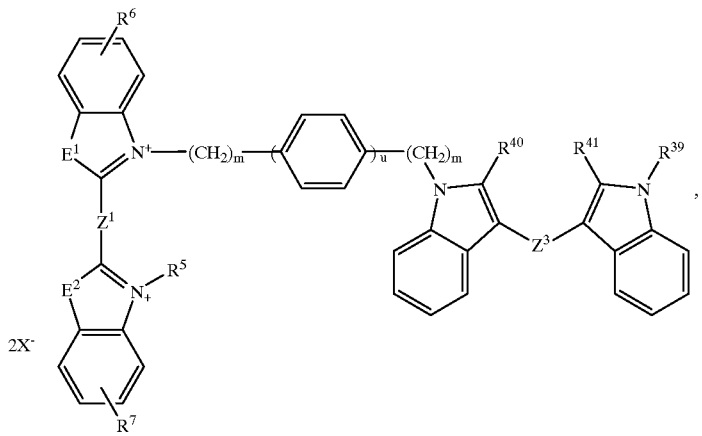
(XXVIII)
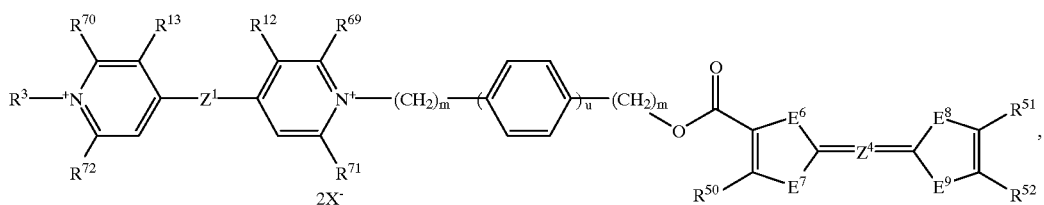
(XXIX)

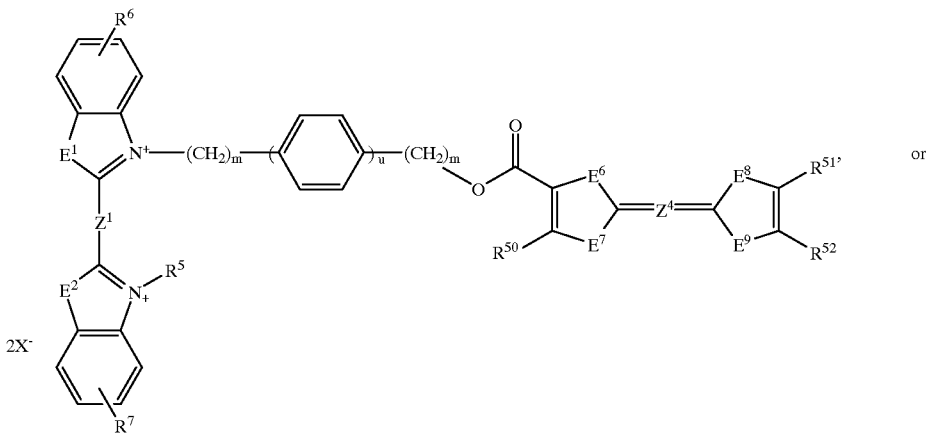
(XXX)
or
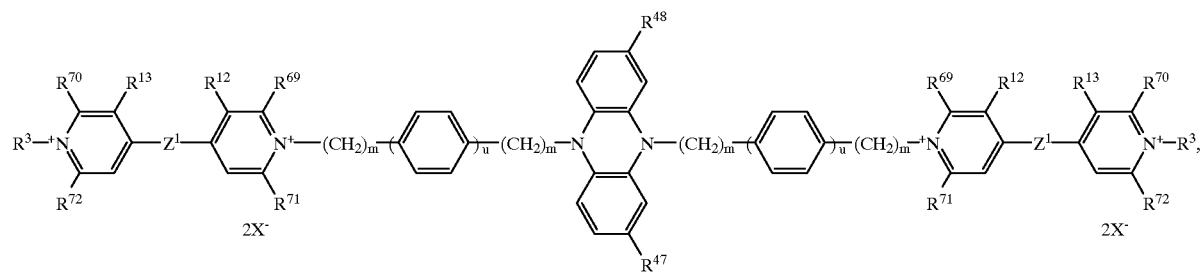
(XXXI)
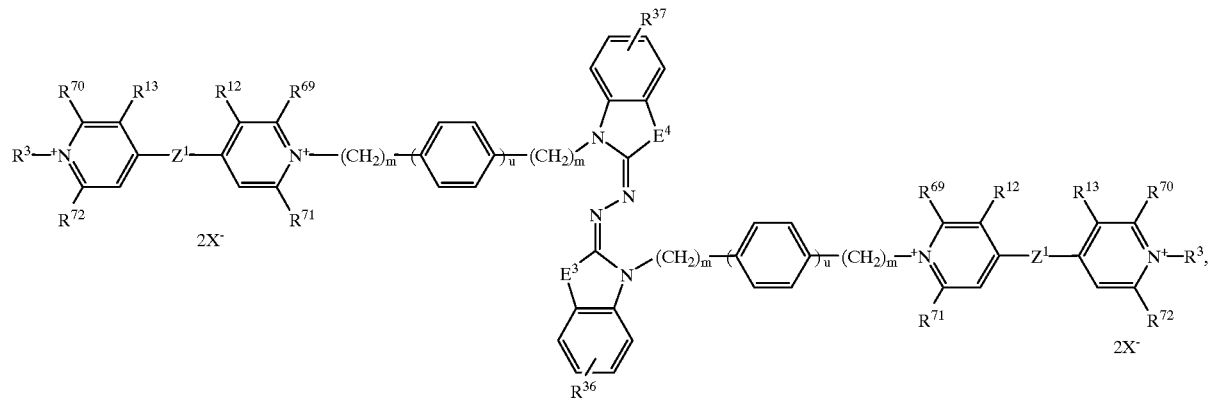
(XXXII)
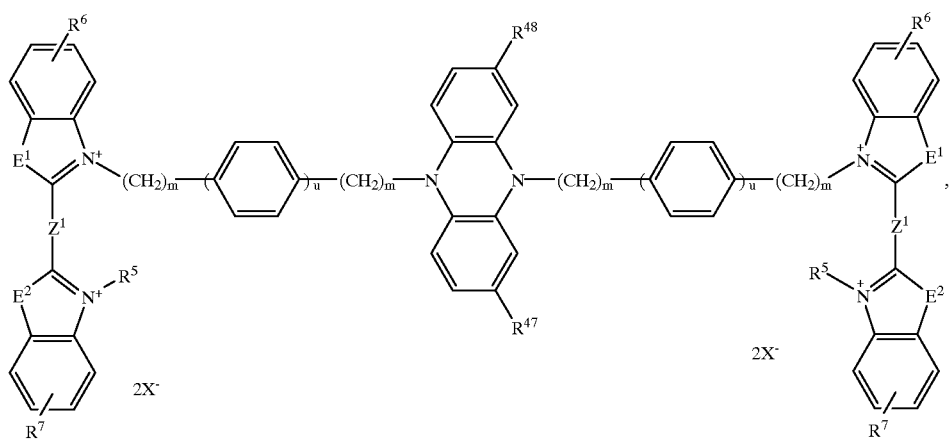
(XXXIII)

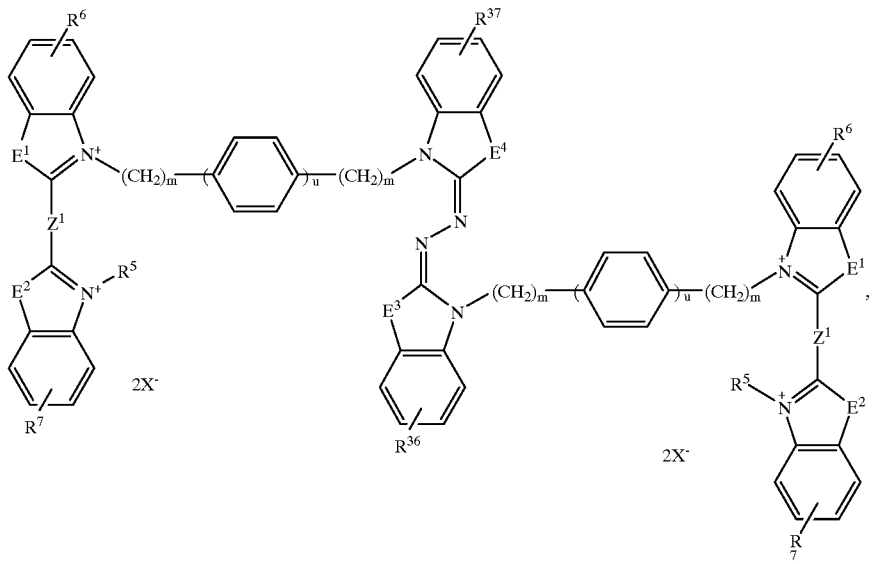
(XXXIV)
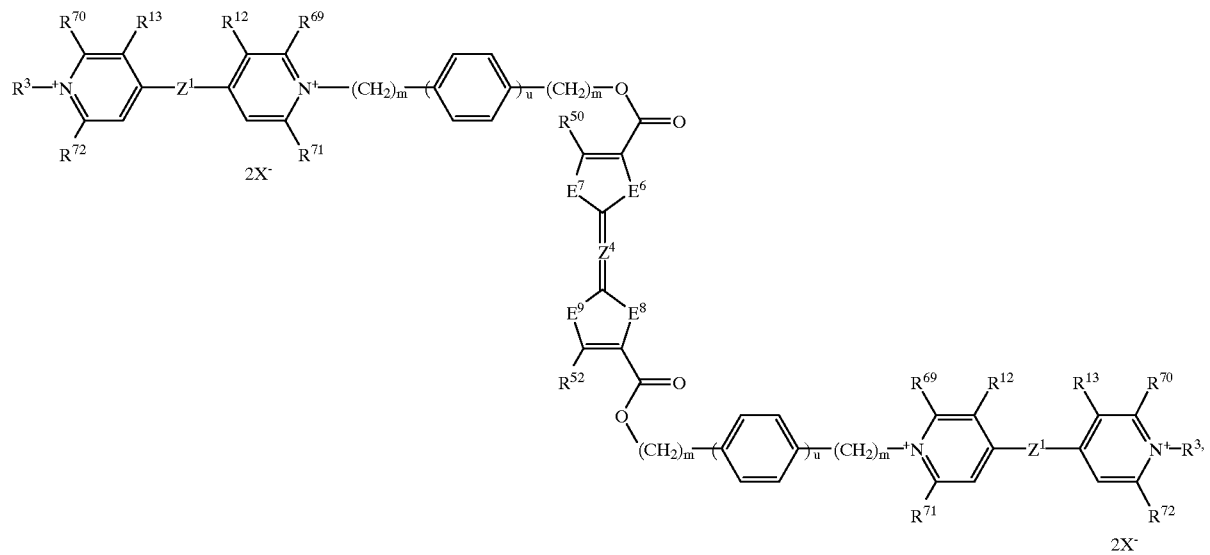
(XXXV)

-continued
(XXXVI)
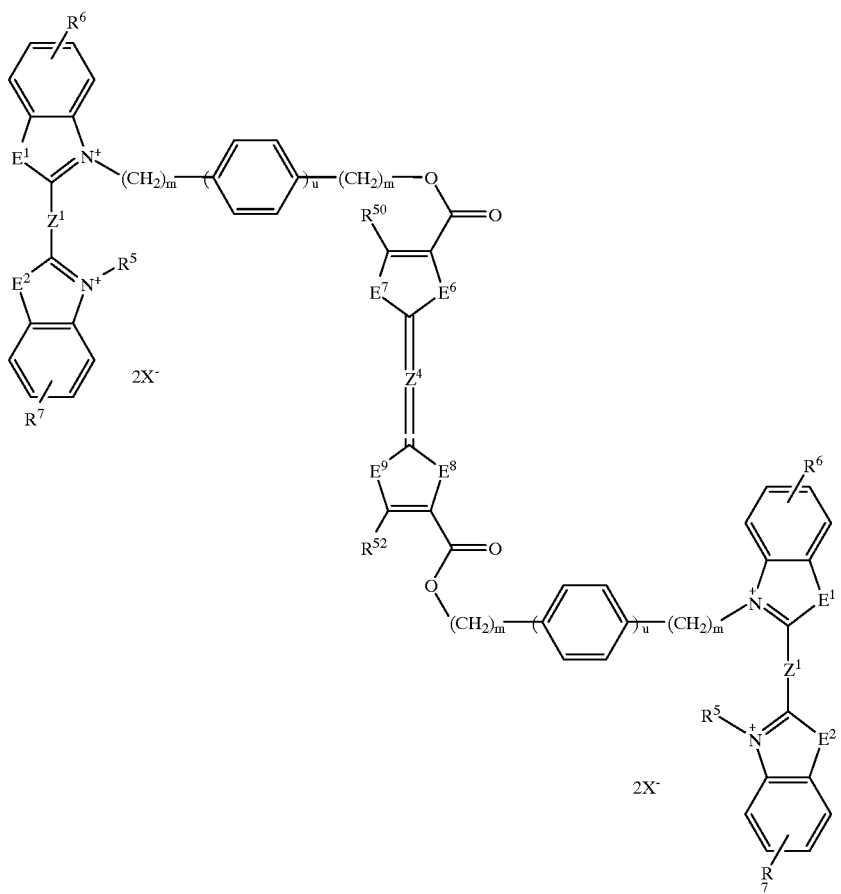
or at least one substance of the formula (Ic) corresponding to one of the formulae
$$RED_1-B-OX_2-B-RED_1 \quad (Ic)$$
(XXXVII)
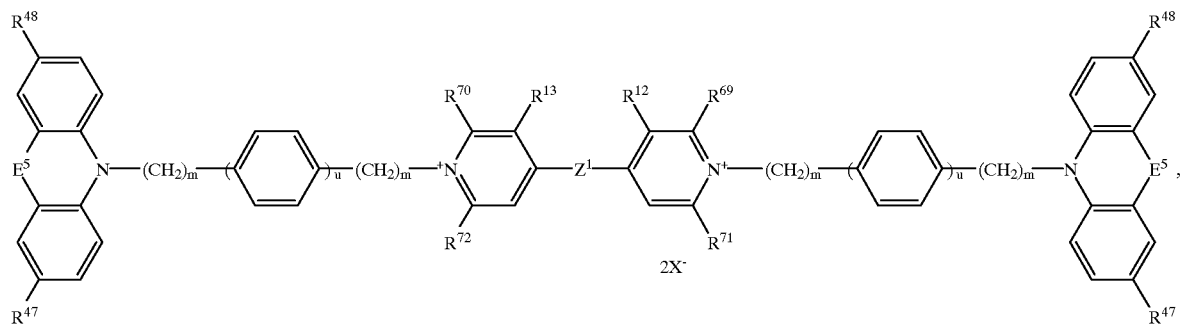

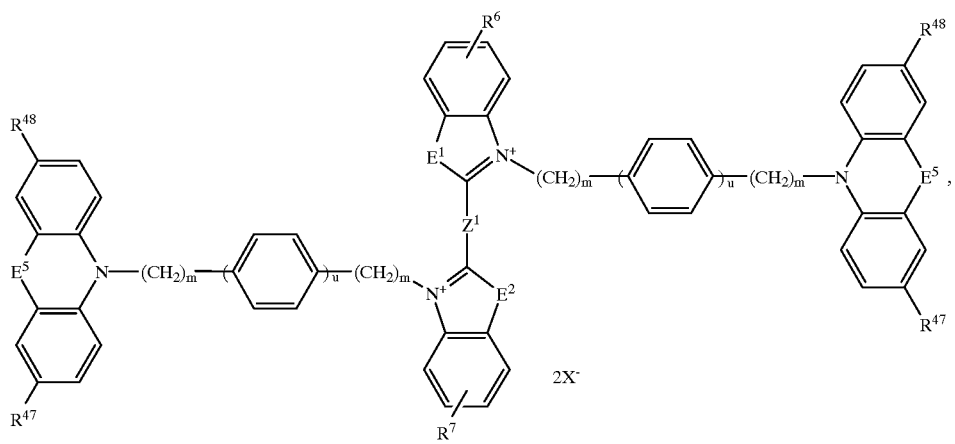
(XXXVIII)
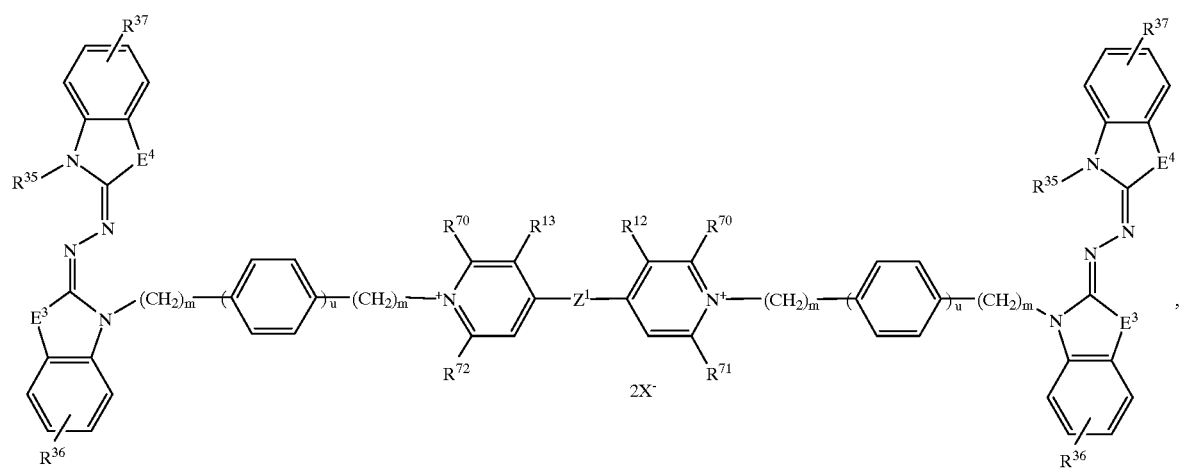
(XXXIX)
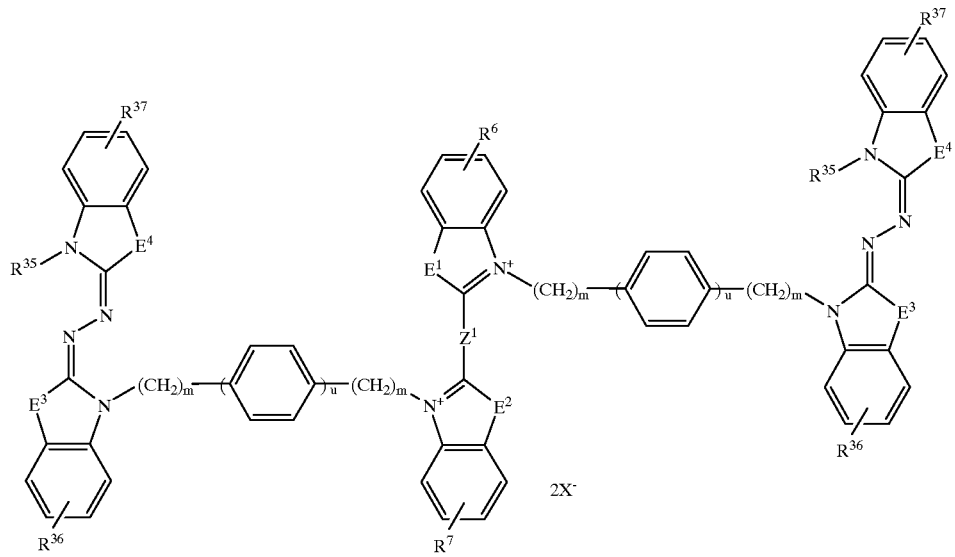
(XL)

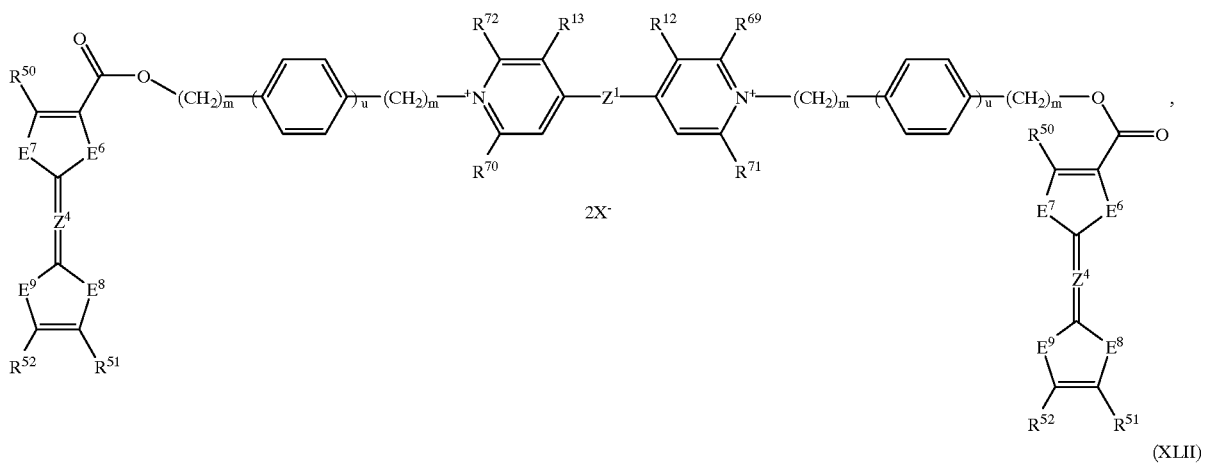

(XLI)

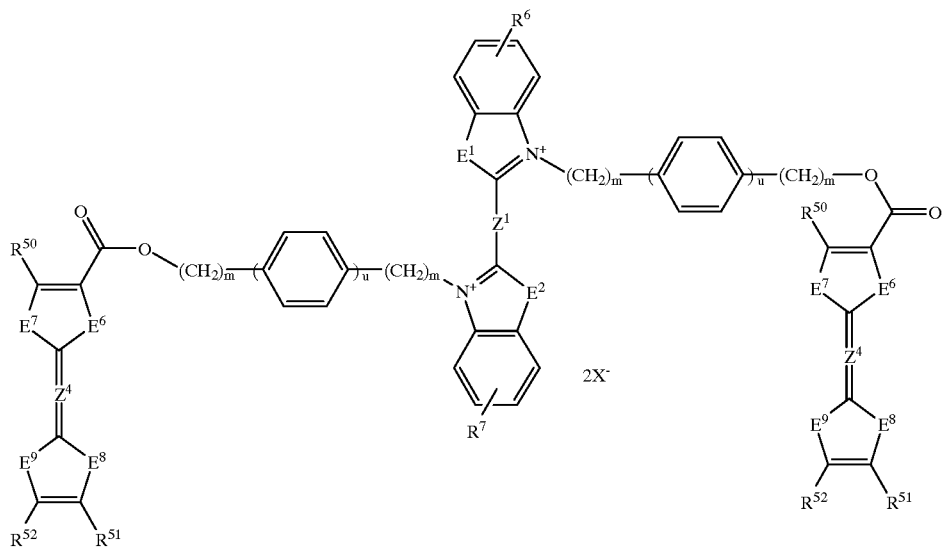

(XLII)

in which
- $R^3$, $R^5$, $R^{35}$ and $R^{39}$ independently of one another represent methyl, ethyl, propyl, butyl, pentyl, hexyl or benzyl,
- $R^6$, $R^7$ and $R^{36}$, $R^{37}$ in pairs are identical and represent hydrogen, methyl, methoxy, chlorine, cyano or methoxycarbonyl,
- $R^{12}$ and $R^{13}$ represent hydrogen or, if $Z^1$ denotes a direct bond, together represent a CH=CH bridge,
- $R^{69}$ to $R^{72}$ are identical and represent hydrogen or methyl,
- $E^1$ and $R^2$ are identical and represent O or S,
- $Z^1$ represents a direct bond or —CH=CH—,
- $R^{32}$, $R^{47}$ and $R^{48}$ represent hydrogen,
- $E^3$ to $E^5$ independently of one another represent O, S or $NR^{59}$, but where $E^3$ and $E^4$ are identical,
- $R^{29}$ to $R^{31}$ and $R^{59}$ independently of one another represent methyl, ethyl, propyl, butyl, pentyl, hexyl or benzyl, where $R^{29}$ to $R^{31}$ are preferably identical,
- $R^{40}$ and $R^{41}$ are identical and represent hydrogen, methyl, ethyl, propyl, butyl or phenyl,
- $Z^3$ represents a direct bond, —CH=CH— or —N=N—,
- $R^{50}$ to $R^{52}$ independently of one another represent hydrogen, methyl, methoxy, chlorine, cyano, methoxycarbonyl, ethoxycarbonyl or phenyl, but are preferably identical,
- $E^6$ to $E^9$ are identical to one another and represent S, Se or $NR^{59}$,
- $Z^4$ represents a direct double bond or a =CH—CH= or =N—N= bridge,
- m represents an integer from 1 to 5,
- u represents 0 or 1 and
- $X^-$ represents a colorless anion which is redox-inert under the conditions.

10. An electrochromic substance corresponding to the formula

(I)

in which
Y and Z independently of one another represent a radical $OX_2$ or $RED_1$ but in which at least one Y represents $OX_2$ and at least one Z represents $RED_1$,
in which
$OX_2$ represents the radical of a reversibly electrochemically reducible redox system and RED$_1$ represents the radical of a reversibly electronically oxidizable redox system, where the radical of the formula (XX)

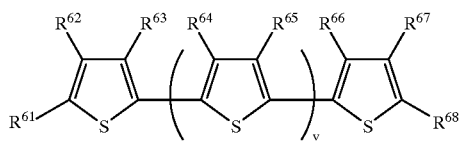

where

R$^{61}$ to R$^{68}$ independently of one another denote hydrogen, C$_1$- to C$_6$-alkyl, C$_1$- to C$_4$-alkoxy, cyano, C$_1$- to C$_4$-alkoxycarbonyl or C$_6$- to C$_{10}$-aryl, or R$^{61}$, R$^{62}$ and R$^{67}$; and R$^{68}$ independently of one another together form a —(CH$_2$)$_3$—, —(CH$_2$)$_4$— or —CH=CH—CH=CH— bridge, v denotes an integer between 0 and 10, is excluded, B represents a bridge member, c represents an integer from 0 to 5 and a and b independently of one another represent an integer from 0 to 5, with the exception of compounds of the formula

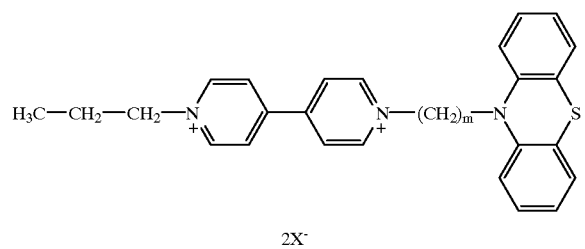

in which m represents an integer from 2 to 16 and

X$^-$ represents a colorless anion which is redox-inert under the conditions.

11. An electrochromic substance according to claim 10 corresponding to one of the formulae

| | |
|---|---|
| OX$_2$—B—RED$_1$ | (Ia), |
| OX$_2$—B—RED$_1$—B—OX$_2$ | (Ib), |
| RED$_1$—B—OX$_2$—B—RED$_1$ | (Ic), |
| or | |
| OX$_2$—(B—RED$_1$—B—OX$_2$)$_d$—B—RED$_1$ | (Id), | in which OX$_2$, RED$_1$ and B have the meanings given in claim 10 and d is an integer from 1 to 5.

12. An electrochromic substance as claimed in claim 10 of the formulae (XXI)

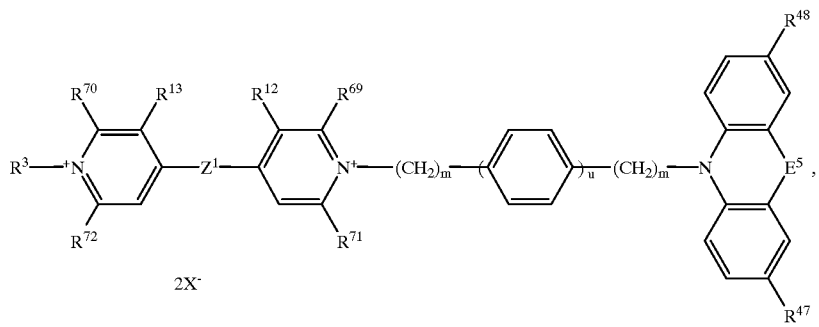

(XXII)

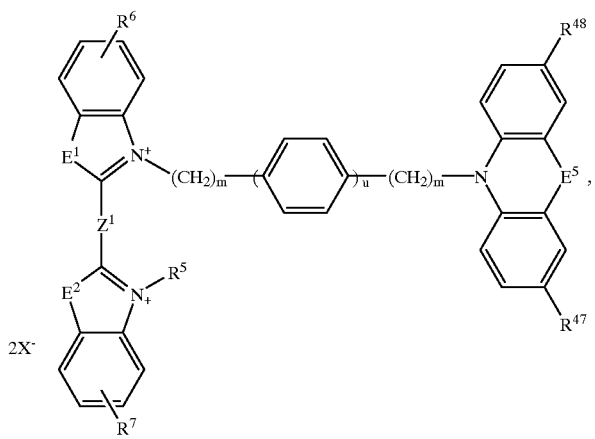

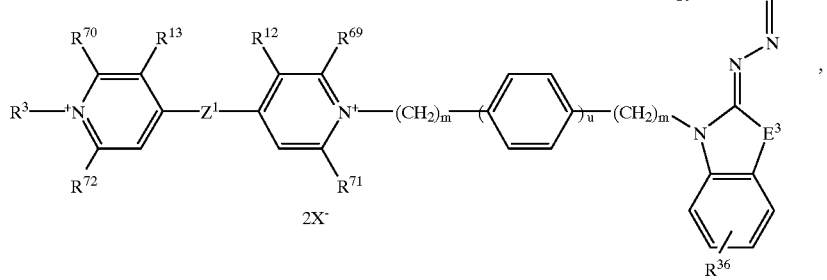
(XXIII)
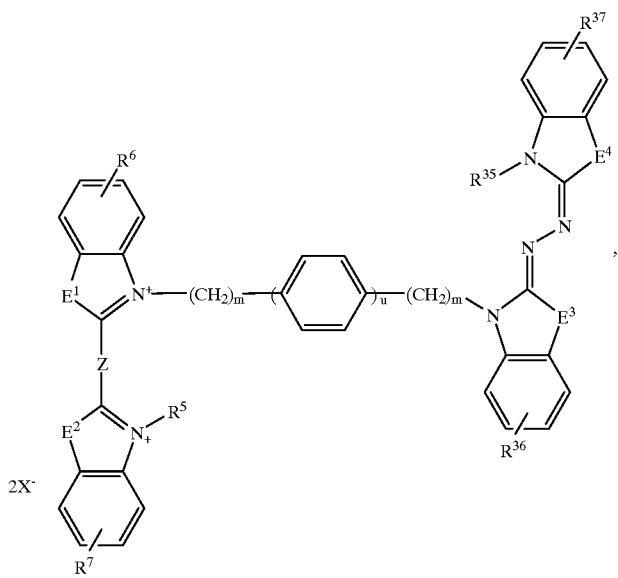
(XXIV)
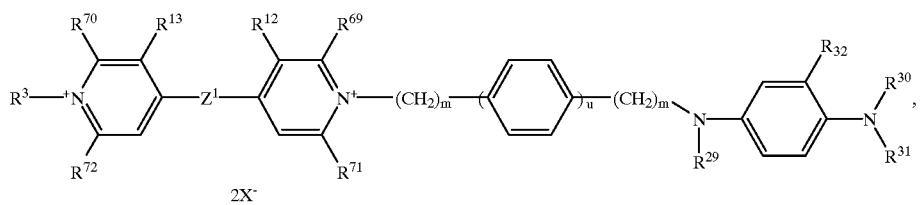
(XXV)

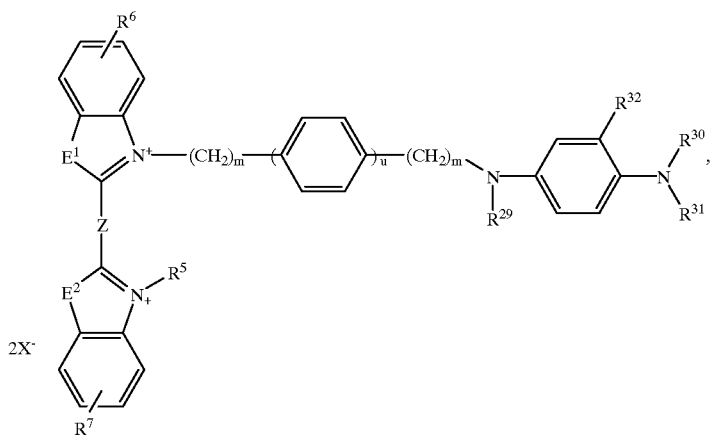
(XXVI)
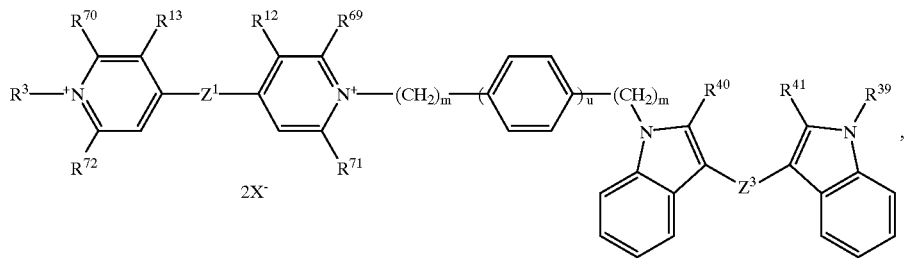
(XXVII)
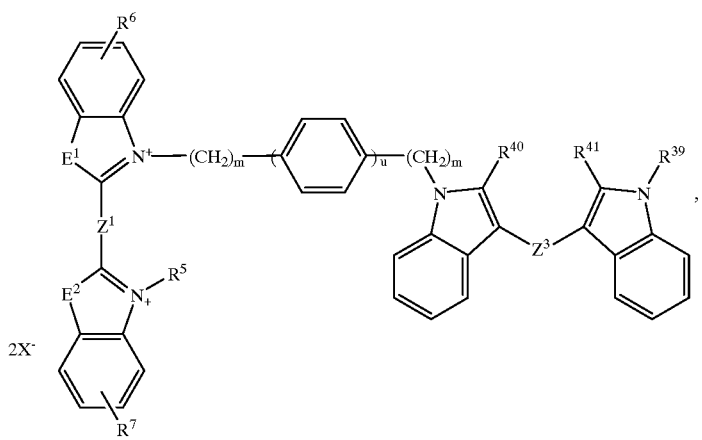
(XXVIII)
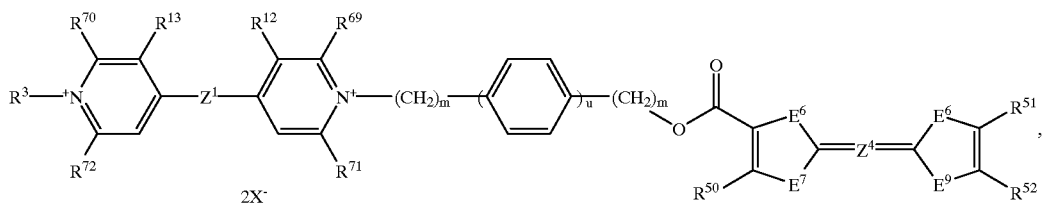
(XXIX)

(XXX)
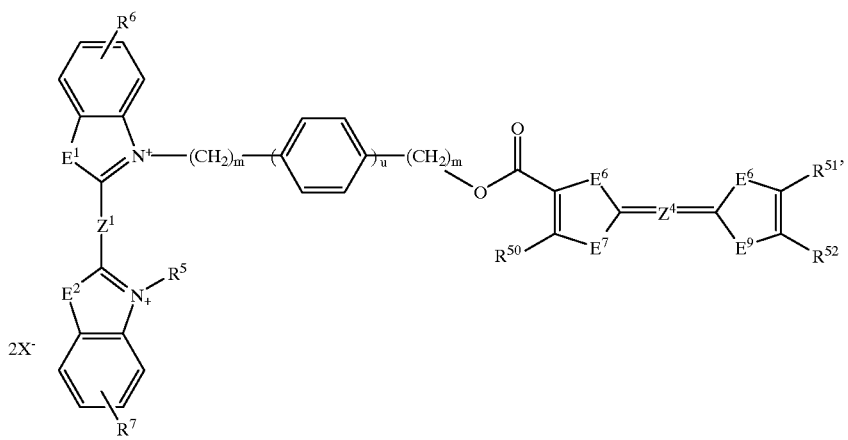
(XXXI)
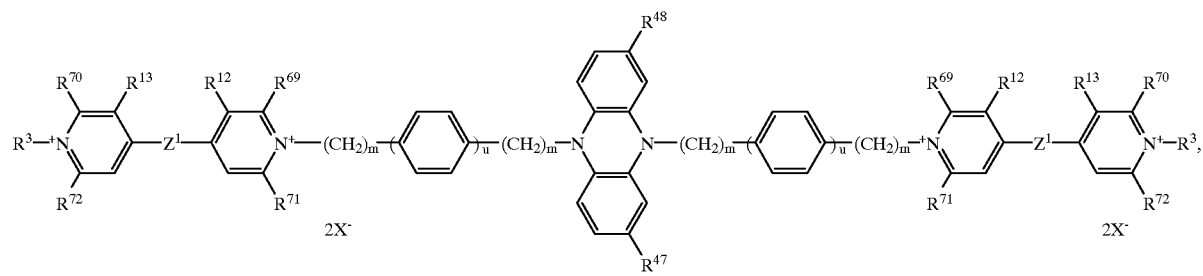
(XXXII)
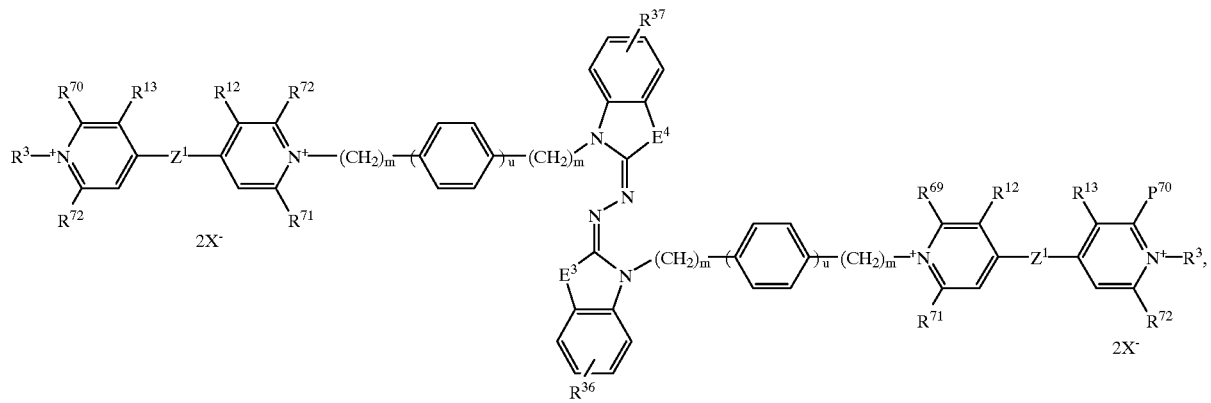
(XXXIII)
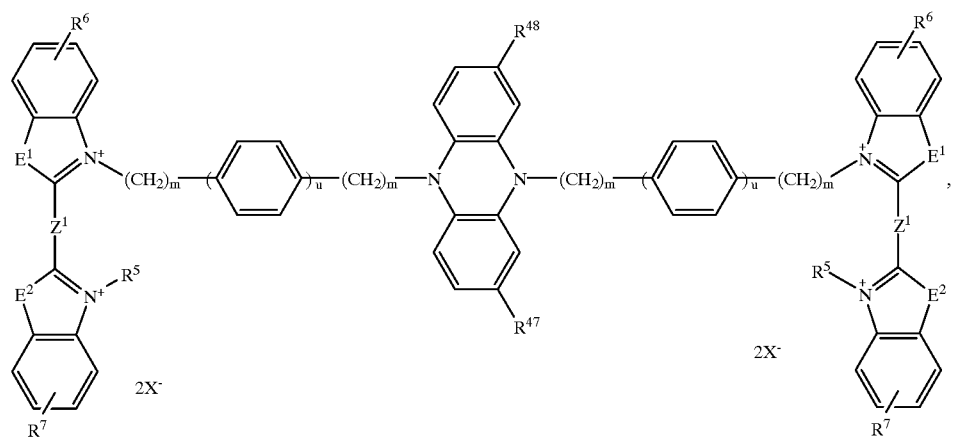

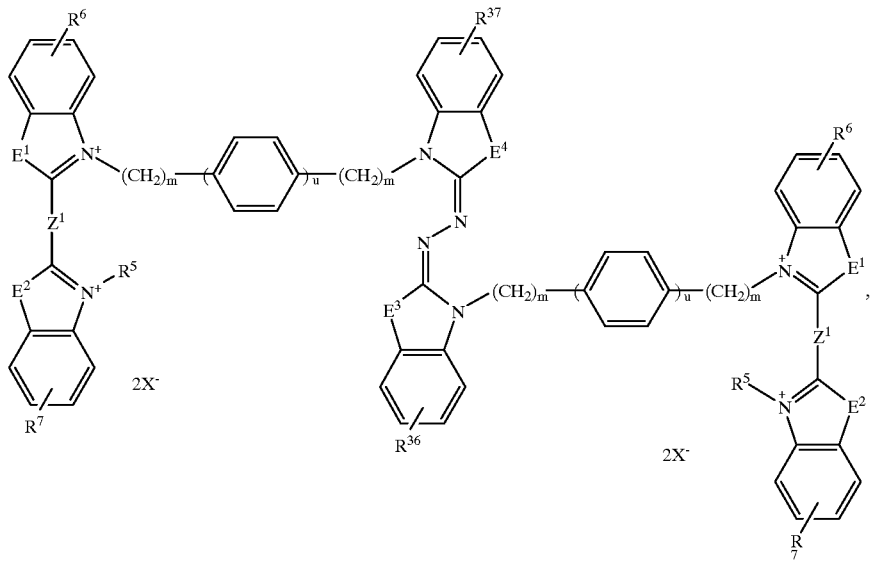
(XXXIV)
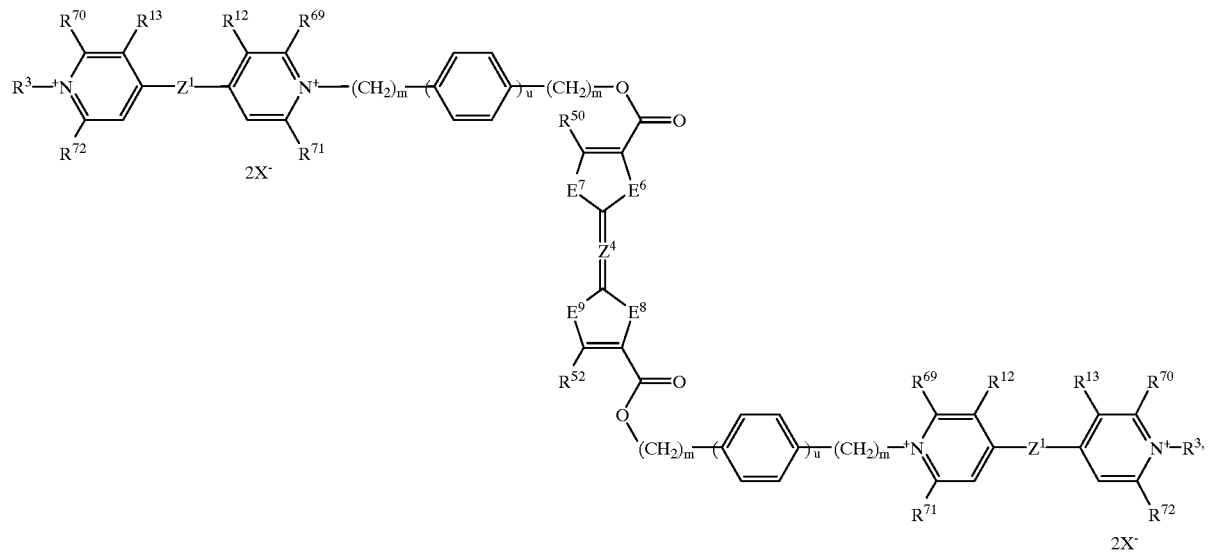
(XXXV)

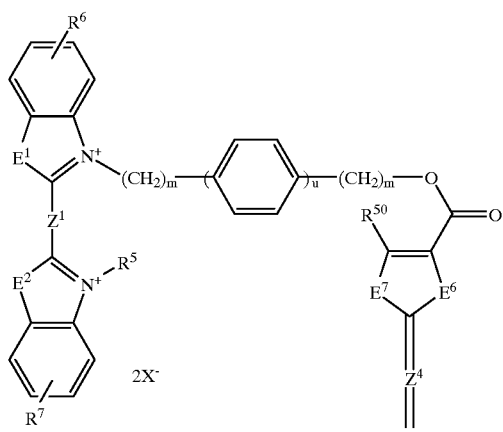
(XXXVI)
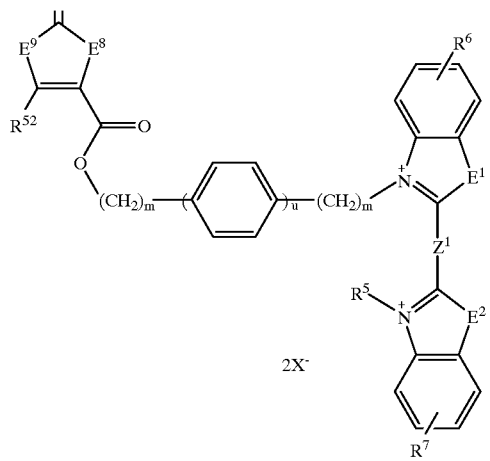
or at least one substance of the formula (Ic) corresponding to one of the formulae
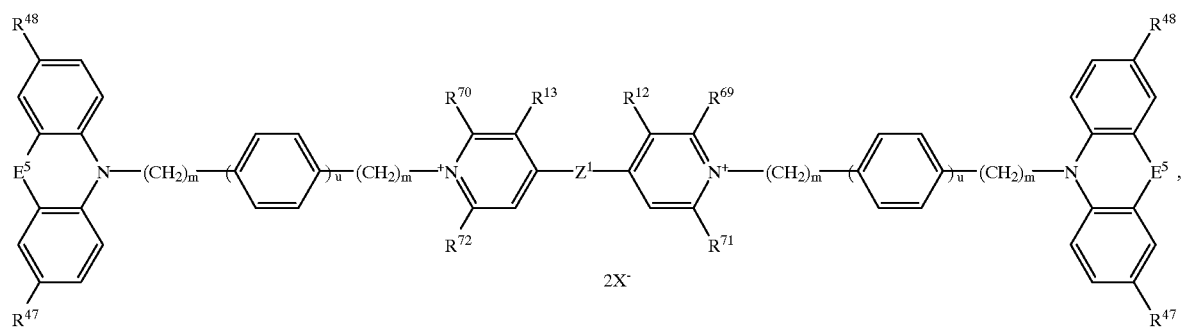
(XXXVII)

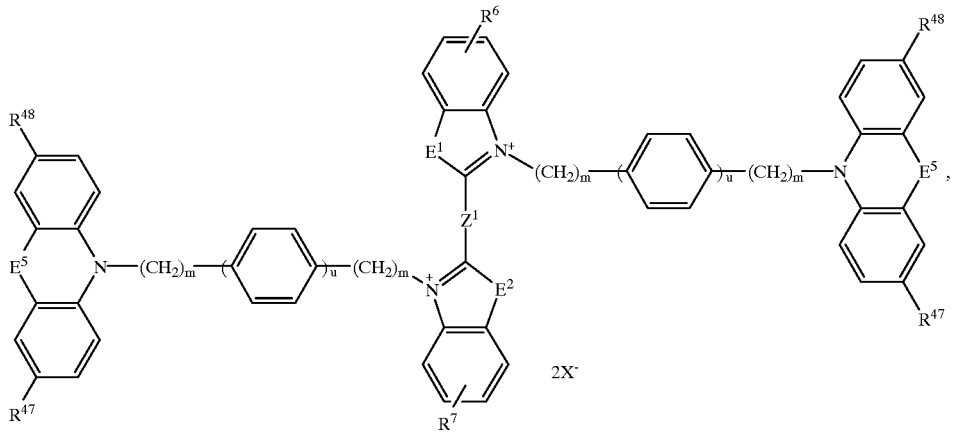
(XXXVIII)
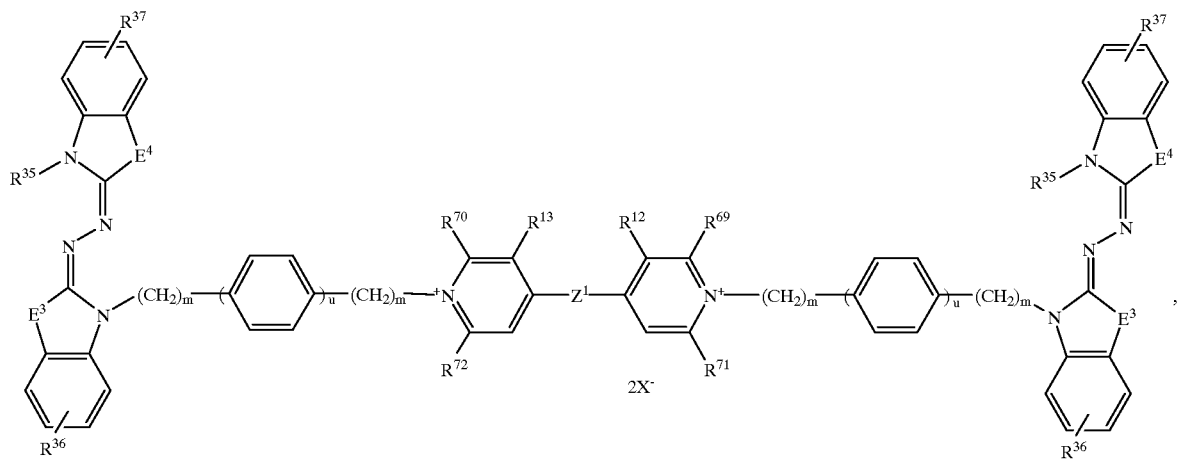
(XXXIX)

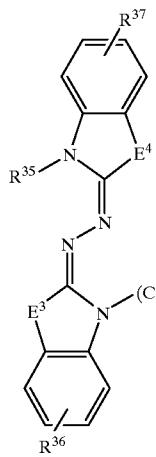
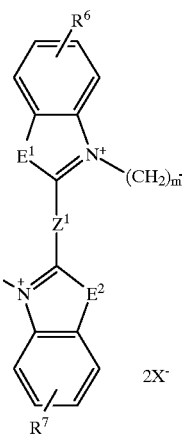
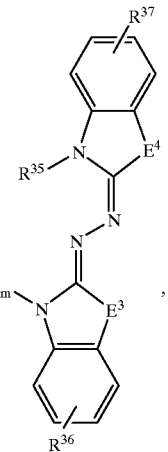
(XL)
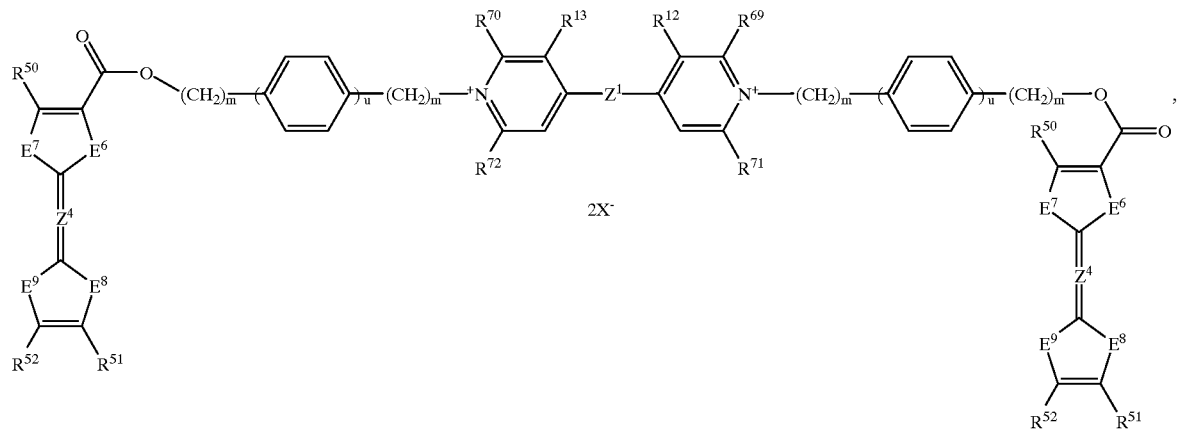
(XLI)

(XLII)

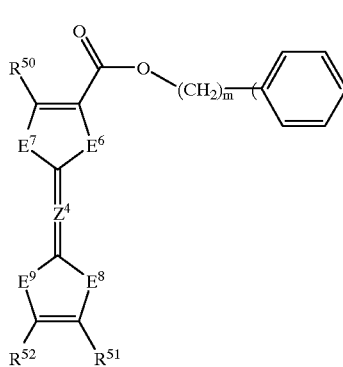
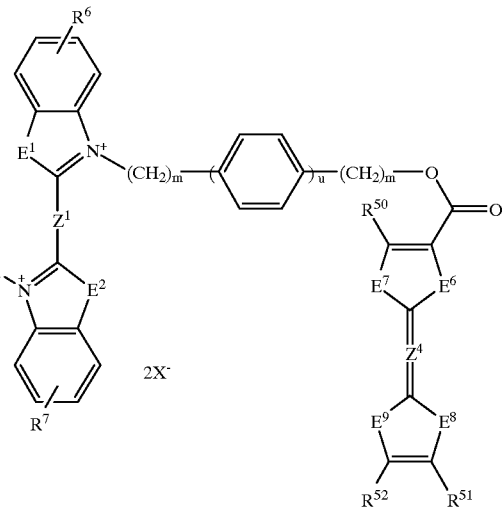

in which $R^3$, $R^5$, $R^{35}$ and $R^{39}$ independently of one another represent methyl, ethyl, propyl, butyl, pentyl, hexyl or benzyl, $R^6$, $R^7$ and $R^{36}$, $R^{37}$ in pairs are identical and represent hydrogen, methyl, methoxy, chlorine, cyano or methoxycarbonyl, $R^{12}$ and $R^{13}$ represent hydrogen or, if $Z^1$ denotes a direct bond, together represent a CH=CH bridge, $RE^{69}$ to $R^{72}$ are identical and represent hydrogen or methyl, $E^1$ and $R^2$ are identical and represent O or S, $Z^1$ represents a direct bond or —CH=CH—, $R^{32}$, $R^{47}$ and $R^{48}$ represent hydrogen, $E^3$ to $E^5$ independently of one another represent O, S or $NR^{59}$, but where $E^3$ and $E^4$ are identical, $R^{29}$ to $R^{31}$ and $R^{59}$ independently of one another represent methyl, ethyl, propyl, butyl, pentyl, hexyl or benzyl, where $R^{29}$ to $R^{31}$ are preferably identical, $R^{40}$ and $R^{41}$ are identical and represent hydrogen, methyl, ethyl, propyl, butyl or phenyl, $Z^3$ represents a direct bond, —CH=CH— or —N=N—, $R^{50}$ to $R^{52}$ independently of one another represent hydrogen, methyl, methoxy, chlorine, cyano, methoxycarbonyl, ethoxycarbonyl or phenyl, but are preferably identical, $E^6$ to $E^9$ are identical to one another and represent S, Se or $NR^{59}$, $Z^4$ represents a direct double bond or a =CH—CH=— or =N—N= bridge, m represents an integer from 1 to 5, u represents 0 or 1 and $X^-$ represents a colorless anion which is redox-inert under the conditions.

13. A process for the preparation of an electrochromic substance as claimed in claim 10, which comprises reacting a compound of the formula $$OX_2\text{—}B\text{—}A \qquad (XLIII)$$

with a compound of the formula $$RED_1 \qquad (XLIV)$$

or a compound of the formula $$OX_2 \qquad (LXV)$$

with a compound of the formula $$A\text{—}B\text{—}RED_1 \qquad (XLVI)$$

in which

A denotes a leaving group, such as chlorine, bromine, iodine, $OSO_2$-alkyl, $OSO_2$-perfluoroalkyl or $OSO_2$-aryl and $OX_2$, $RED_1$ and B have the meaning given in claim 10.

14. An electrochromic liquid comprising an electrochromic system as claimed in claim 1 and at least one inert solvent.

15. An electrochromic device comprising an electrochromic liquid as claimed in claim 14.

16. An electrochromic device as claimed in claim 15, which is constructed as a cell.

17. An electrochromic device as claimed in claim 15, which comprises two transparent panes of glass or plastic facing one another, one of which is optionally metallized and the sides of which facing one another are coated with an electrically conductive coating, the electrochromic liquid being contained between the two panes.

18. An electrochromic device as claimed in claim 16, wherein the cell is constructed as a solar cell, or as a window pane, mirror, sunroof or display.

19. An electrochromic substance as claimed in claim 10, wherein a and b independently represent an integer from 0 to 3.

* * * * *

UNITED STATES PATENT AND TRADEMARK OFFICE
CERTIFICATE OF CORRECTION

PATENT NO. : 6,241,916 B1
DATED : June 5, 2001
INVENTOR(S) : Uwe Claussen et al.

It is certified that error appears in the above-identified patent and that said Letters Patent is hereby corrected as shown below:

Column 5,
Line 6, after "$R^{70}$;" delete "and";

Column 7,
Line 25, replace "$R^{73}$" with -- $R^{75}$ --;
Line 27, replace "$R^{73}$ and $R^{74}$" with -- $R^{75}$ and $R^{76}$ --; replace "$NR^{73}R^{74}$" with -- $NR^{75}R^{76}$ --;

Column 9,
Line 7, replace "$R^{73}$" with -- $R^{75}$ --;
Line 9, replace "$R^{73}$ and $R^{74}$" with -- $R^{75}$ and $R^{76}$ --; replace "$NR^{73}R^{74}$" with -- $NR^{75}R^{76}$ --;
Line 27, replace "—$(CH)_m$—" with -- —$(CH_2)_m$— --;

Column 19,
Replace Chemical Compound (XXXVI) with the new Chemical Compound (XXXVI) as shown below:

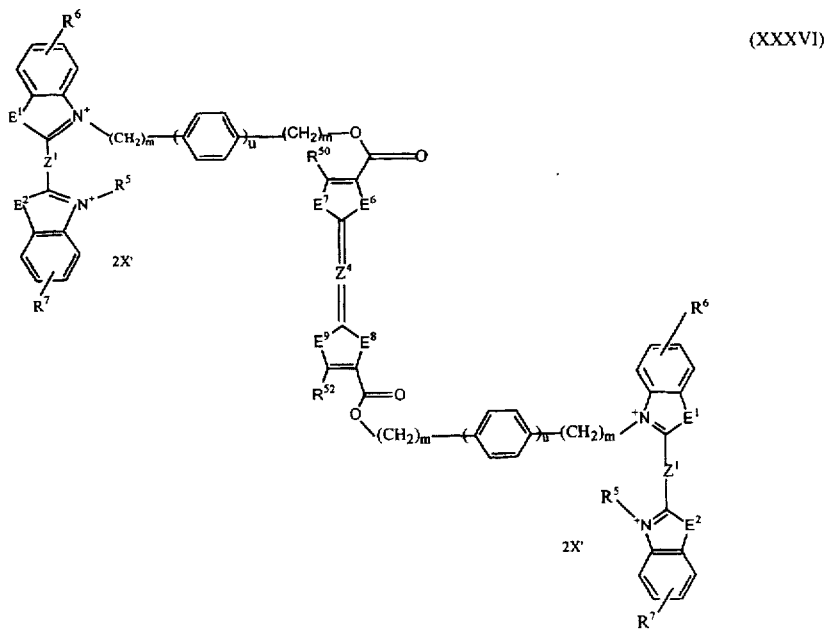

(XXXVI)

UNITED STATES PATENT AND TRADEMARK OFFICE
CERTIFICATE OF CORRECTION

PATENT NO. : 6,241,916 B1
DATED : June 5, 2001
INVENTOR(S) : Uwe Claussen et al.

It is certified that error appears in the above-identified patent and that said Letters Patent is hereby corrected as shown below:

Column 35,
Replace Chemical Compound (XXXVI) with the new Chemical Compound (XXXVI) as shown below:

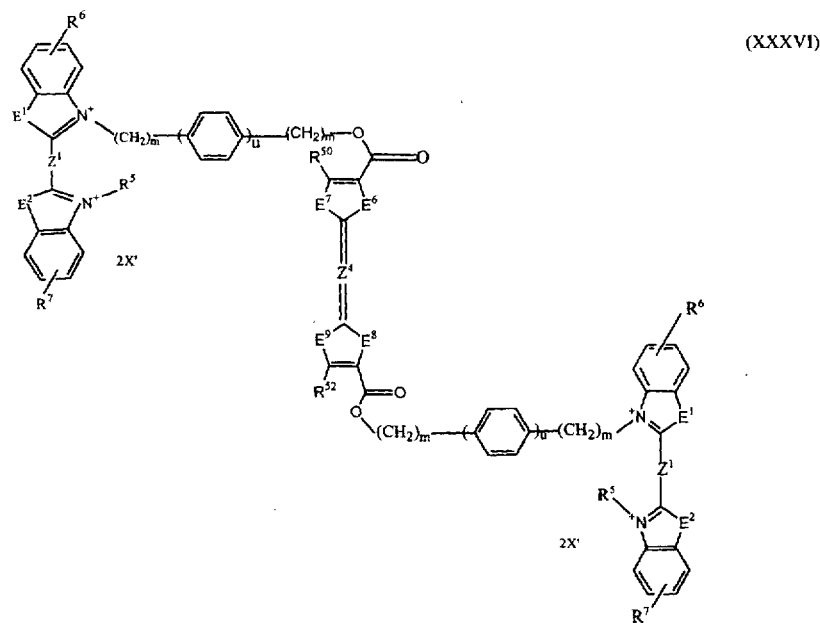

Column 63,
Line 27, replace chemical compound with the new chemical compound as shown below;

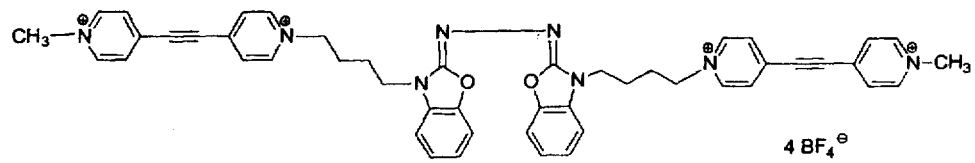

UNITED STATES PATENT AND TRADEMARK OFFICE
CERTIFICATE OF CORRECTION

PATENT NO. : 6,241,916 B1
DATED : June 5, 2001
INVENTOR(S) : Uwe Claussen et al.

It is certified that error appears in the above-identified patent and that said Letters Patent is hereby corrected as shown below:

Column 68,
Line 13, after "$R^{70}$" delete "and";
Line 41, replace "$R^2$-$R^{27}$" with -- $R^{22}$-$R^{27}$ --;

Column 70,
Line 29, replace "$R^{73}$" with -- $R^{75}$ --;
Line 31, replace "$R^{73}$ and $R^{75}$" with -- $R^{75}$ and $R^{76}$ --; replace "$NR^{73}R^{74}$" with -- $NR^{75}R^{76}$ --;
Line 66, replace "O $X_2$" with -- $OX_2$ --;

Column 72,
Line 3, replace "$R^{73}$" with -- $R^{75}$ --;
Line 5, replace "$R^{73}$ and $R^{74}$" with -- $R^{75}$ and $R^{76}$ --; replace "$NR^{73}R^{74}$" with -- $NR^{75}R^{76}$ --;
Line 21, replace "—$(CH)_m$—" with -- —$(CH_2)_m$— --;

Column 80,
Replace chemical compound "(XXX)" with the chemical compound as shown below;

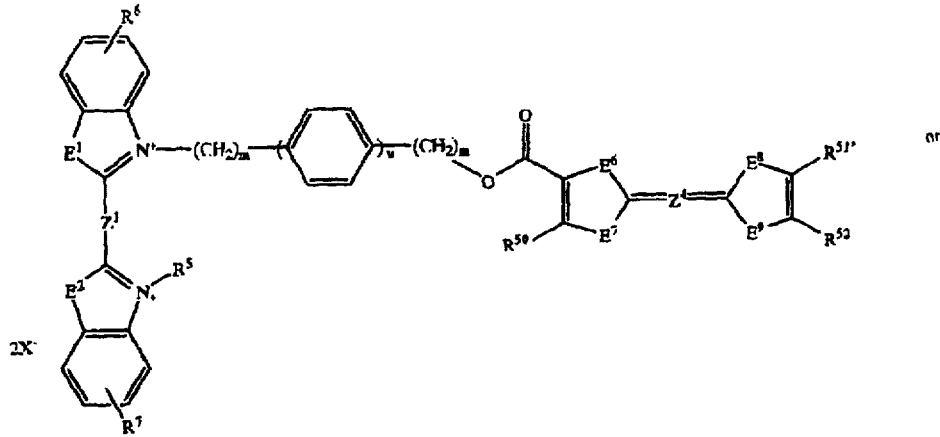

or at least one of the formula (Ic) corresponding to one of the formulae

UNITED STATES PATENT AND TRADEMARK OFFICE
CERTIFICATE OF CORRECTION

PATENT NO. : 6,241,916 B1
DATED : June 5, 2001
INVENTOR(S) : Uwe Claussen et al.

It is certified that error appears in the above-identified patent and that said Letters Patent is hereby corrected as shown below:

Column 99,
Line 40, et seq., delete "or at least one substance of the formula (Ic) corresponding to one of the formulae"

Signed and Sealed this

Thirtieth Day of April, 2002

Attest:

JAMES E. ROGAN
*Director of the United States Patent and Trademark Office*

*Attesting Officer*